United States Patent
Han et al.

(10) Patent No.: US 11,091,479 B2
(45) Date of Patent: Aug. 17, 2021

(54) TRIAZOLOPYRIDIN-3-ONES OR THEIR SALTS AND PHARMACEUTICAL COMPOSITIONS COMPRISING THE SAME

(71) Applicant: YUHAN CORPORATION, Seoul (KR)

(72) Inventors: Tae Dong Han, Yongin-si (KR); Hee Jae Tak, Yongin-si (KR); Eun Kyung Kim, Seongnam-si (KR); Dong Hoon Kim, Suwon-si (KR); Su Bin Choi, Yongin-si (KR); Sol Park, Yongin-si (KR); Hyun Ho Choi, Suwon-si (KR); Tae Wang Kim, Yongin-si (KR); Mi Kyeong Ju, Suwon-si (KR); Na Ry Ha, Seoul (KR)

(73) Assignee: YUHAN CORPORATION, Seoul (KR)

( * ) Notice: Subject to any disclaimer, the term of this patent is extended or adjusted under 35 U.S.C. 154(b) by 0 days.

(21) Appl. No.: 16/712,673

(22) Filed: Dec. 12, 2019

(65) Prior Publication Data

US 2020/0223844 A1 Jul. 16, 2020

(30) Foreign Application Priority Data

Dec. 14, 2018 (KR) .......................... 10-2018-0161732
Oct. 24, 2019 (KR) .......................... 10-2019-0133228

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .. C07D 403/10; C07D 249/12; C07D 401/04; C07D 401/10; C07D 401/14; C07D 403/04; C07D 403/14; C07D 405/10; C07D 405/14; C07D 409/06; C07D 409/14; C07D 413/14; C07D 471/04; C07D 519/00
See application file for complete search history.

(56) References Cited

U.S. PATENT DOCUMENTS

| | | | |
|---|---|---|---|
| 10,562,865 B2 | 2/2020 | Han et al. | |
| 10,899,719 B2 | 1/2021 | Han et al. | |
| 2005/0096360 A1* | 5/2005 | Salter-Cid | A61K 31/44 514/357 |
| 2007/0293548 A1* | 12/2007 | Wang | C07C 211/29 514/357 |
| 2008/0249151 A1 | 10/2008 | Sweeney et al. | |
| 2010/0029697 A1 | 2/2010 | Debenham et al. | |
| 2010/0298330 A1* | 11/2010 | McDonald | A61P 25/00 514/239.5 |
| 2012/0225878 A1 | 9/2012 | Bouillot et al. | |
| 2015/0158813 A1* | 6/2015 | Deodhar | A61P 43/00 514/603 |
| 2016/0009721 A1 | 1/2016 | Wu et al. | |
| 2017/0360756 A1 | 12/2017 | Brown et al. | |
| 2018/0104198 A1* | 4/2018 | Rippmann | A61P 27/02 |
| 2018/0297987 A1* | 10/2018 | Coates | C07D 401/04 |
| 2019/0308944 A1* | 10/2019 | Han | C07D 403/14 |
| 2019/0322655 A1 | 10/2019 | Han et al. | |
| 2020/0223808 A1 | 7/2020 | Han et al. | |
| 2020/0223827 A1 | 7/2020 | Han et al. | |

FOREIGN PATENT DOCUMENTS

| | | | |
|---|---|---|---|
| EP | 0000014 A1 | 12/1978 | |
| WO | WO-2005/014583 A1 | 2/2005 | |
| WO | WO-2006/138695 A1 | 12/2006 | |
| WO | WO-2008/119662 A1 | 10/2008 | |
| WO | WO-2009/066152 A2 | 5/2009 | |
| WO | WO-2010/096722 A1 | 8/2010 | |
| WO | WO-2013/134562 A1 | 9/2013 | |
| WO | WO-2013/163675 A1 | 11/2013 | |
| WO | WO-2016/106106 A2 | 6/2016 | |
| WO | WO-2017/046738 A1 | 3/2017 | |
| WO | WO-2017/136870 A1 | 8/2017 | |
| WO | WO-2017/191112 A1 | 11/2017 | |
| WO | WO-2018/073154 A1 | 4/2018 | |
| WO | WO-2018/157190 A1 | 9/2018 | |
| WO | WO-2018196677 A1 * | 11/2018 | ........... C07C 311/16 |
| WO | WO-2018233633 A1 * | 12/2018 | ......... A61K 31/4245 |
| WO | WO-2019101086 A1 * | 5/2019 | ........... A61K 31/395 |
| WO | WO-2019129213 A1 * | 7/2019 | ............. A61P 35/00 |
| WO | WO-2019/180644 A1 | 9/2019 | |
| WO | WO-2019/180646 A1 | 9/2019 | |
| WO | WO-2020/063854 A1 | 4/2020 | |
| WO | WO-2020/069330 A2 | 4/2020 | |

(Continued)

OTHER PUBLICATIONS

Salmi; Antioxidants & Redox Signalling 2019, 30, 314-332. (Year: 2019).*
Chemical Abstracts STN Registry Database record for RN 1700586-71-5, Entered into STN on May 7, 2015. (Year: 2015).*
International Search Report and Written Opinion on PCT/IB2019/060738 dated Apr. 6, 2020.
Dobosz, et al., "Synthesis of 1-(3-Amino-2-Hydroksypropyl)-4-Phenyl-1,2,4-Triazolin-5-One and 1-(3-Amino-2-Hydroksypropyl)-3,4-Diphenyl-1,2,4-Triazolin-5-One Derivatives", Acta Poloniae Pharmaceutica—Drug Research 57(5): 363-368 (2000).

(Continued)

*Primary Examiner* — Daniel R Carcanague
(74) *Attorney, Agent, or Firm* — Sheppard Mullin Richter & Hampton LLP

(57) ABSTRACT

The present technology provides triazolopyridin-3-ones or pharmaceutically acceptable salts thereof, preparation processes thereof, pharmaceutical compositions comprising the same, and uses thereof. The triazolopyridin-3-ones or their pharmaceutically acceptable salts exhibit inhibitory activity on VAP-1 and therefore can be usefully applied, e.g., for the treatment and prophylaxis of nonalcoholic hepatosteatosis (NASH).

38 Claims, No Drawings

(56) References Cited

FOREIGN PATENT DOCUMENTS

| WO | WO-2020/069335 A2 | 4/2020 | | |
|----|-------------------|--------|---|---|
| WO | WO-2020/083264 A1 | 4/2020 | | |
| WO | WO-2020/086747 A2 | 4/2020 | | |
| WO | WO-2020063696 A1 * | 4/2020 | .............. | A61P 27/02 |
| WO | WO-2020/121261 A1 | 6/2020 | | |
| WO | WO-2020/121263 A1 | 6/2020 | | |
| WO | WO-2020/143763 A1 | 7/2020 | | |

OTHER PUBLICATIONS

International Search Report and Written Opinion on PCT/IB2019/060736 dated Apr. 6, 2020.

International Search Report and Written Opinion, issued in Int'l. App. No. PCT/IB2019/052276, 13 pages (dated Aug. 1, 2019).

International Search Report and Written Opinion, issued in Int'l. App. No. PCT/IB2019/052278, 12 pages (dated Aug. 1, 2019).

Kirton, et al., "Function-blocking antibodies to human vascular adhesion protein-1: A potential anti-inflammatory therapy", Eur. J. Immunol. 35: 3119-3130 (2005).

McDonald, et al., "Semicarbazide Sensitive Amine Oxidase and Vascular Adhesion Protein-1: One Protein Being Validated as a Therapeutic Target for Inflammatory Diseases", Chapter 15, Annual Reports in Medicinal Chemistry 42: 229-243 (2007).

Noda, et al., "Inhibition of vascular adhesion protein-1 suppresses endotoxin-induced uveitis", The FASEB Journal 22(4): 1094-1103 (2008).

Salmi, et al., "VAP-1: an adhesin and an enzyme", Trends in Immunology 22(4): 211-216 (2001).

Salter-Cid, et al., "Anti-Inflammatory Effects of Inhibiting the Amine Oxidase Activity of Semicarbazide-Sensitive Amine Oxidase", J. Pharmacol. Exp. Ther. 315(2): 553-562 (2005).

Sheng, et al., "Design and synthesis of novel triazole antifungal derivatives by structure-based bioisosterism", Eur. J. Med. Chem. 46(11): 5276-5282 (2011).

Still, et al., "Rapid Chromatographic Technique for Preparative Separations with Moderate Resolution", J. Org. Chem. 43(14): 2923-2925 (1978).

Stolen, et al., "Absence of the Endothelial Oxidase AOC3 Leads to Abnormal Leukocyte Traffic In Vivo", Immunity 22: 105-115 (2005).

Sun, et al., "Discovery of triazolone derivatives as novel, potent stearoyl-CoA desaturase-1 (SCD1) inhibitors", Bioorganic & Medicinal Chemistry 23(3): 455-465 (2015).

Weston, et al., "Vascular adhesion protein-1 promotes liver inflammation and drives hepatic fibrosis", The Journal of Clinical Investigation 125(2): 501-520 (2015).

* cited by examiner

TRIAZOLOPYRIDIN-3-ONES OR THEIR SALTS AND PHARMACEUTICAL COMPOSITIONS COMPRISING THE SAME

CROSS-REFERENCE TO RELATED APPLICATIONS

This application claims the benefit of priority to Korean Patent Application No. 10-2018-0161732, filed Dec. 14, 2018, and Korean Patent Application No. 10-2019-0133228, filed Oct. 24, 2019, the entire contents of each of which are incorporated by reference herein in their entirety.

FIELD

The present technology relates to triazolopyridin-3-ones or pharmaceutically acceptable salts thereof having inhibitory activity on vascular adhesion protein (VAP-1), a process for the preparation thereof, a pharmaceutical composition comprising the same, and uses thereof.

BACKGROUND

Vascular adhesion protein-1 (VAP-1) is a semicarbazide-sensitive amine oxidase (SSAO), which is abundantly present in human plasma. VAP-1 is an ectoenzyme comprising a short cytoplasmic tail, a single transmembrane domain, and an extracellular domain with large and high glycosylation containing the center of activity. In addition, VAP-1 exists not only as a membrane-bound form in the endothelium, but also as a soluble form in serums (soluble VAP-1, sVAP-1). This form was shown to be a product cleaved from the membrane-bound VAP-1, and appears to have similar properties as the tissue-bound form. It has been also reported that VAP-1 is normally stored in intracellular granules within endothelial cells, but when an inflammatory response is evoked in response to inflammatory stimuli, it is translocated onto the cell membrane, and its expression is upregulated, and therefore, it is expressed more strongly in inflamed tissues than in normal tissues.

Substrates for VAP-1 include endogenous methylamine and aminoacetone as well as some xenobiotic amines such as tyramine and benzylamine.

VAP-1 has two physiological functions: the first is amine oxidase activity stated earlier in this section, and the second is cell adhesion activity. Due to these two activities, VAP-1 has been shown to play a key role in the leakage of inflammatory cells as it acts as an adhesion protein for leukocytes in inflamed sites [Trends Immunol. (2001) 22: 211]. VAP-1-deficient transgenic mice are healthy, develop normally, and fertile, and phenotypically normal, but exhibit a marked decrease in the inflammatory responses evoked in response to various inflammatory stimuli [Immunity. (2005) 22: 105].

In addition, inhibitory activity of VAP-1 in multiple animal models of human diseases (e.g., carrageenan-induced paw inflammation, oxazolone-induced colitis, lipopolysaccharide-induced lung inflammation, collagen-induced arthritis, endotoxin-induced uveitis) by the use of antibodies or small molecules has been shown to prevent leukocyte from rolling, adhering, and leaking, and reduce levels of inflammatory cytokines and chemokines, thereby reducing the severity of the disease [Eur J Immunol. (2005) 35: 3119; J Pharmacol Exp Ther. (2005) 315: 553; Annu Rep Med Chem. (2007) 42: 229; FASEB J. (2008) 22: 1094]. Inflammation is the first reaction of the immune system to infection or stimulus and in such a process, the movement of leukocytes into the tissue through circulation is an important step. The leukocytes are first bound to adhesion proteins and then adhered to the endothelium before they start to pass through blood vessel walls. VAP-1 is highly expressed in endothelial venules (HEV) such as high endothelial venules in lymphoid organs, as well as hepatic sinusoidal endothelial cells, (HSEC), smooth muscle cells, and adipocytes. The VAP-1 expression on the cell surface of endothelial cells is strictly regulated and is increased during inflammation. VAP-1 activates NF-κB when it is present in the substrate, and the NF-κB is activated within the HSEC while E-selectin and chemokine IL-8 that are other adhesion molecules are upregulated ex vivo. This suggests that VAP-1 may be a key factor for the regulation of the inflammatory response, and it seems therefore likely that VAP-1 inhibitors may be effective anti-inflammatory drugs in a wide range of human diseases.

Nonalcoholic fatty liver disease (NAFLD), histologically, encompasses simple steatosis, nonalcoholic hepatosteatosis (NASH), and liver cirrhosis. Among these, unlike simple steatosis (non-alcoholic fatty liver, NAFL), NASH potentially progresses to liver cirrhosis and hepatoma (hepatocellular carcinoma). In NASH, insulin resistance is known to play an important role in the progression of disease, along with oxidative stress, inflammatory cascade, and fibrosis. In patients with NAFLD, sVAP-1 levels were found to be elevated, and in VAP-1 knockout (K/O) mice, carbon tetrachloride-induced liver fibrosis was reduced compared with that in wild type animals. In addition, improvement of liver fibrosis by VAP-1 inhibition following administration of VAP-1 antibody was identified by histological changes [J Clin Invest (2015) 125: 501]. Thus, VAP-1 was found to be associated with NASH in clinical studies and animal models of diseases. Inhibitory activity of VAP-1 in the carbon tetrachloride-induced animal model appears to be due to a reduction in infiltration of leukocytes such as T cells, B cells, NKT cells, and NK cells observed in liver fibrosis, and VAP-1 inhibitors have the potential for treating fibrotic diseases.

Thus, a substance that inhibits VAP-1 may be applied to prevention and treatment of various inflammatory diseases and fibrotic diseases.

SUMMARY

The present inventors found that triazolopyridin-3-ones having 3-fluoroallylamine or 3,3-difluoroallylamine groups or their pharmaceutically acceptable salts exhibit inhibitory activity on VAP-1. Therefore, the triazolopyridin-3-ones or their salts can be usefully used in the treatment and prophylaxis of various VAP-1 mediated diseases, for example, nonalcoholic hepatosteatosis (NASH).

Therefore, the present technology provides the triazolopyridin-3-ones or their pharmaceutically acceptable salts, preparation processes thereof, pharmaceutical compositions comprising the same, and uses thereof.

In accordance with one aspect of the present technology, there is provided a triazolopyridin-3-one or a pharmaceutically acceptable salt thereof.

In accordance with one aspect of the present technology, there is provided a preparation process of the triazolopyridin-3-one or a pharmaceutically acceptable salt thereof.

In accordance with another aspect of the present technology, there is provided a pharmaceutical composition comprising the triazolopyridin-3-one or a pharmaceutically acceptable salt thereof as an active ingredient.

In accordance with another aspect of the present technology, there is provided a method of treatment comprising administering the triazolopyridin-3-one or a pharmaceutically acceptable salt thereof.

In accordance with another aspect of the present technology, there is provided the use of the triazolopyridin-3-one or a pharmaceutically acceptable salt thereof in the manufacture of a medicament for inhibition of vascular adhesion protein-1.

It was found by the present technology that triazolopyridin-3-ones having 3-fluoroallylamine or 3,3-difluoroallylamine groups or their pharmaceutically acceptable salts exhibit inhibitory activity on VAP-1. Therefore, the compounds according to the present technology or pharmaceutically acceptable salts thereof can be usefully applied for the treatment and prophylaxis of VAP-1 mediated various diseases, for example, nonalcoholic hepatosteatosis (NASH).

In one aspect, provided herein is a compound of Formula X

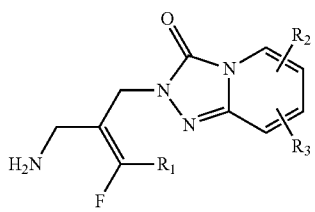

(Formula X)

or a stereoisomer thereof or a pharmaceutically acceptable salt thereof;
wherein
$R_1$ is hydrogen or fluoro; and
$R_2$ and $R_3$, each independently, are selected from the group consisting of hydrogen, halogen, $C_{1-6}$ alkyl, —R, and —C≡C—R;
wherein said R is substituted or unsubstituted cyclic ring, optionally containing 1 to 5 heteroatom ring members chosen from O, N, or S, and the cyclic ring is aromatic or non-aromatic.

In some embodiments, R is substituted or unsubstituted aryl. In some embodiments, R is substituted or unsubstituted phenyl. In some embodiments, R is substituted or unsubstituted heteroaryl. In some embodiments, R is substituted or unsubstituted non-aromatic heterocyclic. In some embodiments, the substituted or unsubstituted cyclic ring is selected from the group consisting of substituted or unsubstituted benzene, substituted or unsubstituted pyridine, substituted or unsubstituted tetrahydropyridine, substituted or unsubstituted pyrazole, substituted or unsubstituted benzodioxole, substituted or unsubstituted 2,3-dihydro benzodioxine, substituted or unsubstituted benzothiazole, substituted or unsubstituted benzoxadiazole, substituted or unsubstituted benzotriazole, substituted or unsubstituted indazole, substituted or unsubstituted pyrrolo[2,3-b]pyridine, substituted or unsubstituted 3,4-dihydroquinolin-2-one, substituted or unsubstituted 3,4-dihydro-1,4-benzoxazine, substituted or unsubstituted 1,4-benzoxazin-3-one, substituted or unsubstituted 1,3-dihydro-3,1-benzoxazin-2-one, substituted or unsubstituted 2,3-dihydro-pyrido[2,3-b][1,4]oxazine, substituted or unsubstituted pyrido[2,3-b][1,4]oxazin-2-one, substituted or unsubstituted 3,4-dihydro-pyrido[3,2-b][1,4]oxazine, and substituted or unsubstituted pyrido[3,2-b][1,4]oxazin-3-one.

In another aspect, provided herein is a compound of Formula 1

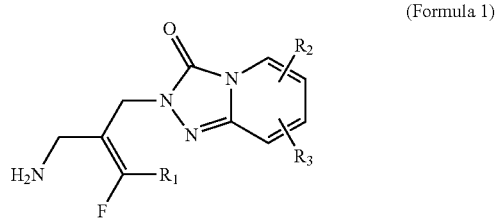

(Formula 1)

or a stereoisomer thereof or a pharmaceutically acceptable salt thereof;
wherein
$R_1$ is hydrogen or fluoro, and
$R_2$ and $R_3$, each independently, are selected from the group consisting of hydrogen, halogen, $C_{1-6}$ alkyl, —R, and —C≡C—R, wherein $R_2$ and $R_3$ cannot be simultaneously hydrogen, halogen, $C_{1-6}$ alkyl, —R, or —C≡C—R,
wherein said R is a cyclic ring selected from the group consisting of benzene, pyridine, tetrahydropyridine, pyrazole, benzodioxole, 2,3-dihydrobenzodioxine, benzothiazole, benzoxadiazole, benzotriazole, indazole, pyrrolo[2,3-b]pyridine, 3,4-dihydroquinolin-2-one, 3,4-dihydro-1,4-benzoxazine, 1,4-benzoxazin-3-one, 1,3-dihydro-3,1-benzoxazin-2-one, 2,3-dihydro-pyrido[2,3-b][1,4]oxazine, pyrido[2,3-b][1,4]oxazin-2-one, 3,4-dihydro-pyrido[3,2-b][1,4]oxazine, and pyrido[3,2-b][1,4]oxazin-3-one,
wherein said cyclic ring is optionally substituted with a substituent selected from the group consisting of $C_{1-6}$ alkyl, trifluoromethyl, $C_{1-6}$ alkoxy, amino, mono- or di-$C_{1-6}$ alkylamino, di-$C_{1-6}$ alkylaminomethyl, $C_{1-6}$ alkylcarbonylamino, $C_{1-6}$ alkylsulfonyl, morpholinylsulfonyl, morpholinylcarbonyl, piperazinyl, morpholinyl, triazolyl, pyrazolyl, oxazolyl, oxadiazolyl, and cyclopropyl-oxadiazolyl.

In some embodiments, said $R_1$ is fluoro. In some embodiments, said $R_1$ is hydrogen. In some embodiments, said $R_2$ is hydrogen and $R_3$ is halogen, —R, or —C≡C—R. In some embodiments, said $R_2$ is hydrogen and $R_3$ is halogen or —R. In some embodiments, said $R_2$ is hydrogen and $R_3$ is halogen or —C≡C—R. In some embodiments, said $R_2$ is hydrogen and $R_3$ is —R. In some embodiments, said $R_2$ is hydrogen and $R_3$ is —C≡C—R. In some embodiments, said R is a cyclic ring selected from the group consisting of benzene and pyrazole. In some embodiments, said cyclic ring is substituted with a substituent selected from the group consisting of $C_{1-6}$ alkyl, $C_{1-6}$ alkylsulfonyl, and piperazinyl. In some embodiments, $R_1$ is fluoro, $R_2$ is hydrogen, $R_3$ is halogen or —R, wherein said R is a cyclic ring selected from the group consisting of benzene and pyrazole, wherein said cyclic ring is substituted with a substituent selected from the group consisting of $C_{1-6}$ alkyl, $C_{1-6}$ alkylsulfonyl, and piperazinyl.

In another aspect, provided herein is a compound of Formula 11

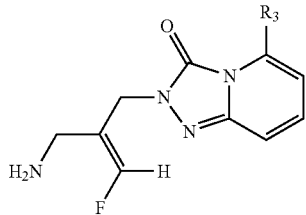

(Formula 11)

or a stereoisomer thereof or a pharmaceutically acceptable salt thereof;
wherein
R₃ is substituted or unsubstituted aryl, or substituted or unsubstituted heteroaryl.
In some embodiments, R₃ is substituted aryl. In some embodiments, R₃ is substituted phenyl. In some embodiments, R₃ is substituted or unsubstituted benzodioxole, substituted or unsubstituted benzoxadiazole, or phenyl, wherein the phenyl is substituted with $C_{1-6}$ alkylcarbonylamino or oxazolyl.

In another aspect, provided herein is a compound of Formula 12

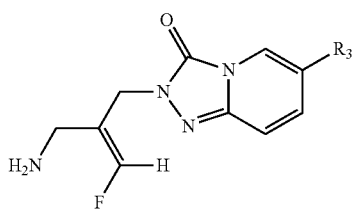

(Formula 12)

or a stereoisomer thereof or a pharmaceutically acceptable salt thereof;
wherein
R₃ is substituted or unsubstituted aryl, or substituted or unsubstituted heteroaryl.
In some embodiments, R₃ is substituted or unsubstituted benzodioxole, substituted or unsubstituted 2,3-dihydrobenzodioxine, substituted or unsubstituted 3,4-dihydroquinolin-2-one, substituted or unsubstituted benzothiazole, substituted or unsubstituted benzoxadiazole, substituted benzene, or substituted pyridine. In some embodiments, the benzene or the pyridine is substituted with trifluoromethyl, amino, $C_{1-6}$ alkylcarbonylamino, $C_{1-6}$ alkylsulfonyl, morpholinylsulfonyl, morpholinyl, triazolyl, and oxazolyl.

In another aspect, provided herein is a compound of Formula 13

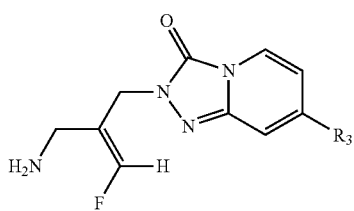

(Formula 13)

or a stereoisomer thereof or a pharmaceutically acceptable salt thereof;
wherein
R₃ is substituted or unsubstituted aryl, or a substituted or unsubstituted cyclic ring.

In some embodiments, R₃ is substituted or unsubstituted aryl. In some embodiments, R₃ is substituted or unsubstituted benzoxadiazole, substituted or unsubstituted 3,4-dihydroquinolin-2-one, substituted or unsubstituted benzodioxole, substituted or unsubstituted indazole, substituted or unsubstituted pyrazole, substituted or unsubstituted benzotriazole, substituted or unsubstituted 1,3-dihydro-3,1-benzoxazin-2-one, substituted or unsubstituted 1,4-benzoxazin-3-one, substituted or unsubstituted 3,4-dihydro-1,4-benzoxazine, or substituted phenyl. In some embodiments, R₃ is phenyl substituted with di-$C_{1-6}$ alkylaminomethyl, $C_{1-6}$ alkylsulfonyl, morpholinylcarbonyl, pyrazolyl, oxazolyl, oxadiazolyl, piperazinyl, and cyclopropyl-oxadiazolyl. In some embodiments, R₃ is a substituted or unsubstituted heterocyclic group. In some embodiments, R₃ is tetrahydropyridine. In some embodiments, R₃ is substituted or unsubstituted heteroaryl. In some embodiments, R₃ is pyrrolo[2,3-b]pyridine or substituted pyridine. In some embodiments, R₃ is a pyridine substituted with trifluoromethyl, $C_{1-6}$ alkoxy, mono- or di-$C_{1-6}$ alkylamino, or morpholinyl. In some embodiments, R₃ is a cyclic ring selected from the group consisting of benzene, pyridine, benzoxadiazole, 3,4-dihydroquinolin-2-one, benzodioxole, indazole, benzotriazole, 1,3-dihydro-3,1-benzoxazin-2-one, 1,4-benzoxazin-3-one, 3,4-dihydro-1,4-benzoxazine, or pyrrolo[2,3-b]pyridine; wherein said cyclic ring is optionally substituted with a substituent selected from the group consisting of $C_{1-6}$ alkyl, trifluoromethyl, $C_{1-6}$ alkoxy, mono- or di-$C_{1-6}$ alkylamino, di-$C_{1-6}$ alkylaminomethyl, $C_{1-6}$ alkylsulfonyl, morpholinylcarbonyl, morpholinyl, pyrazolyl, oxazolyl, oxadiazolyl, and cyclopropyl-oxadiazolyl.

In another aspect, provided herein is a compound of Formula 14

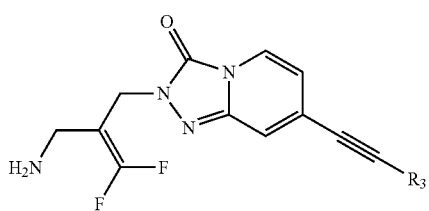

(Formula 14)

or a stereoisomer thereof or a pharmaceutically acceptable salt thereof;
wherein
R₃ is substituted or unsubstituted aryl, or substituted or unsubstituted heteroaryl.
In some embodiments, R₃ is substituted aryl. In some embodiments, R₃ is substituted or unsubstituted 3,4-dihydroquinolin-2-one, or substituted or unsubstituted 3,4-dihydro-1,4-benzoxazine. In some embodiments, R₃ is substituted or unsubstituted heteroaryl. In some embodiments, R₃ is substituted pyrazole, substituted pyridine, substituted or unsubstituted 2,3-dihydro-pyrido[2,3-b][1,4]oxazine, or substituted or unsubstituted 3,4-dihydro-pyrido[3,2-b][1,4]oxazine. In some embodiments, R₃ is pyridine substituted with mono- or di-$C_{1-6}$ alkylamino or morpholinyl.

In another aspect, provided herein is a compound of Table 1.

In another aspect, provided herein is a pharmaceutical composition comprising, consisting essentially of, or consisting of the compound disclosed herein, or a stereoisomer thereof, or a pharmaceutically acceptable salt thereof, and at least one pharmaceutically acceptable excipient.

In another aspect, provided herein is a method of inhibiting vascular adhesion protein (VAP-1), comprising, consisting essentially of, or consisting of administering to a mammal a therapeutically effective amount of the compound or a pharmaceutically acceptable salt thereof disclosed herein.

In another aspect, provided herein is a method of treating NASH in a subject in need thereof, the method comprising, consisting essentially of, or consisting of administering to the subject a therapeutically effective amount of the compound disclosed herein, or a stereoisomer thereof, or a pharmaceutically acceptable salt thereof, or a therapeutically effective amount of the pharmaceutical composition disclosed herein.

In another aspect, provided herein is a use of the compound disclosed herein, or a stereoisomer thereof, or a pharmaceutically acceptable salt thereof, for the manufacture of a medicament for the treatment of NASH.

In another aspect, provided herein is a compound disclosed herein, or a stereoisomer thereof, or a pharmaceutically acceptable salt thereof, for use in treating NASH.

In another aspect, provided herein is a composition disclosed herein for use in treating NASH.

In another aspect, provided herein is a compound disclosed herein, or a stereoisomer thereof, or a pharmaceutically acceptable salt thereof, for use in inhibiting VAP-1.

In another aspect, provided herein is a composition disclosed herein for use in inhibiting VAP-1.

In another aspect, provided herein is a method of treating a disease mediated by VAP-1 in a subject in need thereof, the method comprising, consisting essentially of, or consisting of administering to the subject a therapeutically effective amount of the compound disclosed herein, or a stereoisomer thereof, or a pharmaceutically acceptable salt thereof, or a therapeutically effective amount of the pharmaceutical composition disclosed herein.

In some embodiments, the disease mediated by VAP-1 is selected from the group consisting of lipid and lipoprotein disorders, conditions and diseases which result from chronic fatty and fibrotic degeneration of organs due to accumulated lipid and specifically triglyceride accumulation and subsequent activation of profibrotic pathways, Type I or Type II Diabetes and clinical complications of Type I and Type II Diabetes, chronic intrahepatic or some forms of extrahepatic cholestatic conditions, liver fibrosis, acute intraheptic cholestatic conditions, obstructive or chronic inflammatory disorders that arise out of improper bile composition, gastrointestinal conditions with a reduced uptake of dietary fat and fat-soluble dietary vitamins, inflammatory bowel diseases, obesity and metabolic syndrome (combined conditions of dyslipidemia, diabetes and abnormally high body-mass index), persistent infections by intracellular bacteria or parasitic protozoae, non-malignant hyperproliferative disorders, malignant hyperproliferative disorders, colon adenocarcinoma and hepatocellular carcinoma in particular, liver steatosis and associated syndromes, Hepatitis B infection, Hepatitis C infection and/or of cholestatic and fibrotic effects that are associated with alcohol-induced cirrhosis or with viral-borne forms of hepatitis, liver failure or liver malfunction as an outcome of chronic liver diseases or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

In another aspect, provided herein is a method of preparing a compound of Formula 1a, or a stereoisomer thereof, or a pharmaceutically acceptable salt thereof,

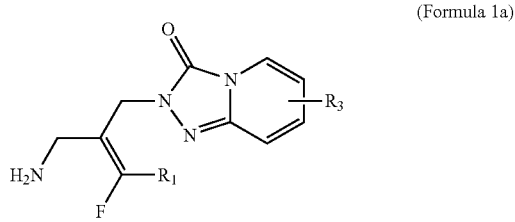

(Formula 1a)

the method comprising, consisting essentially of, or consisting of (a) reacting a compound of Formula 2 with a compound of Formula 3a or a compound of Formula 3b to obtain a compound of Formula 1aa:

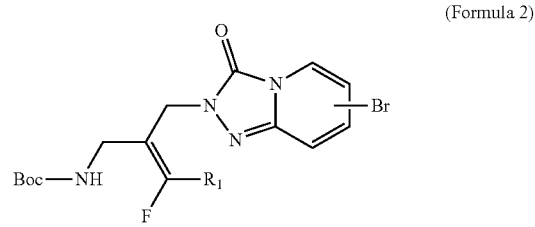

(Formula 2)

(Formula 3a)

(Formula 3b)

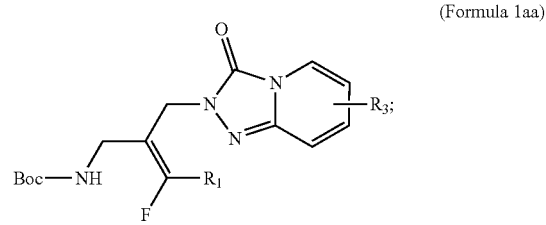

(Formula 1aa)

wherein

Boc is an amine protecting group;

$R_1$ is hydrogen or fluoro;

$R_3$ is selected from the group consisting of $C_{1-6}$ alkyl, —R, and —C≡C—R;

R is substituted or unsubstituted cyclic ring, optionally containing 1 to 5 heteroatom ring members chosen from O, N, or S, and the cyclic ring is aromatic or non-aromatic; and Z is is boronic acid (B(OH)$_2$) or boronic acid pinacol ester; and (b) removing Boc from the compound of Formula 1aa under reaction conditions to obtain the compound of Formula 1a, or the stereoisomer thereof, or the pharmaceutically acceptable salt thereof.

In some embodiments, the compound of Formula 2 is obtained by (a) reacting a compound of Formula 4 with hydrazine to obtain a compound of Formula 5:

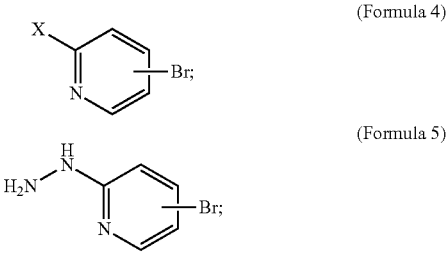

(Formula 4)

(Formula 5)

wherein X is F or Cl;

(b) reacting the compound of Formula 5 under cyclization conditions to obtain a compound of Formula 6:

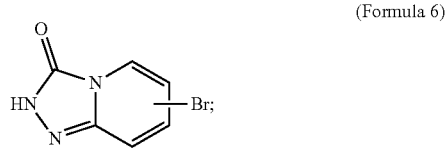

(Formula 6)

and (c) reacting the compound of Formula 6 with a compound of Formula 8 to obtain the compound of Formula 2:

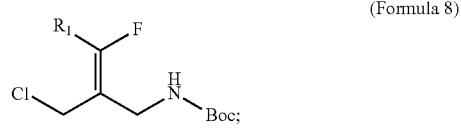

(Formula 8)

wherein $R_1$ is hydrogen or fluoro.

In some embodiments, the cyclization conditions comprise, consist essentially of, or consist of reacting the compound of Formula 5 with carbonyldiimidazole (CDI) in a polar solvent at a temperature ranging from room temperature to 90° C. In some embodiments, R is a cyclic ring selected from the group consisting of benzene, pyridine, tetrahydropyridine, pyrazole, benzodioxole, 2,3-dihydrobenzodioxine, benzothiazole, benzoxadiazole, benzotriazole, indazole, pyrrolo[2,3-b]pyridine, 3,4-dihydroquinolin-2-one, 3,4-dihydro-1,4-benzoxazine, 1,4-benzoxazin-3-one, 1,3-dihydro-3,1-benzoxazin-2-one, 2,3-dihydro-pyrido[2,3-b][1,4]oxazine, pyrido[2,3-b][1,4]oxazin-2-one, 3,4-dihydro-pyrido[3,2-b][1,4]oxazine, and pyrido[3,2-b][1,4]oxazin-3-one, wherein said cyclic ring is optionally substituted with a substituent selected from the group consisting of $C_{1-6}$ alkyl, trifluoromethyl, $C_{1-6}$ alkoxy, amino, mono- or di-$C_{1-6}$ alkylamino, di-$C_{1-6}$ alkylaminomethyl, $C_{1-6}$ alkylcarbonylamino, $C_{1-6}$ alkylsulfonyl, morpholinylsulfonyl, morpholinylcarbonyl, piperazinyl, morpholinyl, triazolyl, pyrazolyl, oxazolyl, oxadiazolyl, and cyclopropyl-oxadiazolyl.

DETAILED DESCRIPTION

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "comprising" or "comprises" is intended to mean that the compositions and methods include the recited elements, but not excluding others. A composition or method "consisting essentially" of the elements as defined herein would not exclude other materials or steps that do not materially affect the basic and novel characteristic(s) of the claimed technology. "Consisting of" shall mean excluding more than trace elements of other ingredients and substantial method steps. Embodiments defined by each of these transition terms are within the scope of this technology. When an embodiment is defined by one of these terms (e.g., "comprising") it should be understood that this disclosure also includes alternative embodiments, such as "consisting essentially of" and "consisting of" for said embodiment.

"Substantially" or "essentially" means nearly totally or completely, for instance, 95%, 96%, 97%, 98%, 99%, or greater of some given quantity.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Where a range of values is provided, it is understood that each intervening value, to the tenth of the unit of the lower limit unless the context clearly dictates otherwise, between the upper and lower limit of that range and any other stated or intervening value in that stated range, is encompassed within the present technology. The upper and lower limits of these smaller ranges may independently be included in the smaller ranges and are also encompassed within the present technology, subject to any specifically excluded limit in the stated range. Where the stated range includes one or both of the limits, ranges excluding either or both of those included limits are also included in the present technology.

In general, "substituted" refers to an organic group (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. The present disclosure is understood to include embodiments where, for instance a "substituted alkyl" optionally contains one or more alkene and/or alkyne. A substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I);

hydroxyls; alkoxy, alkenoxy, alkynoxy, aryloxy, aralkyloxy, heterocyclyloxy, and heterocyclylalkoxy groups; aryl groups; heteroaryl groups; cycloalkyl groups; heterocyclyl groups; carbonyls (oxo); carboxyls; esters; carbamates; urethanes; ureas; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. As used herein, an "optionally substituted" group refers to substituted or unsubstituted group. Accordingly, "optionally substituted" and "substituted or unsubstituted" may be used interchangeably.

Substituted ring groups such as substituted cyclic, substituted cycloalkyl, substituted aryl, substituted heterocyclic and substituted heteroaryl groups also include rings and fused ring systems in which a bond to a hydrogen atom is replaced with a bond to a carbon atom. Therefore, substituted cyclic, substituted cycloalkyl, substituted aryl, substituted heterocyclic and substituted heteroaryl groups may also be substituted with substituted or unsubstituted alkyl, alkenyl, and alkynyl groups as defined below.

As used herein, the term "cyclic ring" refers to an aromatic or non-aromatic ring, optionally containing one or more heteroatoms. Exemplary heteroatoms include, but are not limited to, N, O, S, or B. In some embodiments, the cyclic ring optionally contains 1 to 5 heteroatom ring members chosen from O, N, or S. In some embodiments, the cyclic ring optionally contains 1 to 4 heteroatom ring members chosen from O, N, or S. In some embodiments, the cyclic ring optionally contains 1 to 3 heteroatom ring members chosen from O, N, or S. Cyclic rings include aryl, cycloalkyl, and heterocyclic groups.

As used herein, an "aryl group" refers to a cyclic aromatic hydrocarbon that does not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., benzodioxole, indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

As used herein, the term "cycloalkyl group" refers to a cyclic alkyl group such as, but not limited to, cyclopropyl, cyclobutyl, cyclopentyl, cyclohexyl, cycloheptyl, and cyclooctyl groups. In some embodiments, the cycloalkyl group has 3 to 8 carbon ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-di-substituted cyclohexyl groups, which may be substituted with substituents such as those listed above. In some embodiments, a cycloalkyl group has one or more alkene bonds, but is not aromatic.

As used herein, the term "heterocyclic group" includes aromatic (also referred to as heteroaryl) and non-aromatic ring compounds containing 3 or more ring members, of which one or more is a heteroatom such as, but not limited to, N, O, S or B. In some embodiments, heterocyclic groups include 3 to 20 ring members, whereas other such groups have 3 to 6, 3 to 10, 3 to 12, or 3 to 15 ring members. The heterocyclic group may have 1 to 5 heteroatom ring members chosen from O, N, or S. Heterocyclic groups encompass unsaturated, partially saturated and saturated ring systems, such as, for example, imidazolyl, imidazolinyl and imidazolidinyl groups. The phrase "heterocyclic group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclic groups that have other groups, such as alkyl, oxo or halo groups, bonded to one of the ring members. Rather, these are referred to as "substituted heterocyclic groups". Heterocyclic groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclic groups may be mono-substituted or substituted more than once, such as, but not limited to, pyridyl or piperazinyl groups, which are 2-, 3-, 4-, 5-, or 6-substituted, or disubstituted with various substituents such as those listed above.

As used herein, the term "heteroaryl group" refers to an aromatic ring compound containing 5 or more ring members, of which, one or more is a heteroatom such as, but not limited to, N, O, S or B. In some embodiments, one or more heteroatoms are chosen from N, O, or S. In some embodiments, 1 to 4 heteroatoms are chosen from N, O, or S. In some embodiments, 1 to 5 heteroatoms are chosen from N, O, or S. In some embodiments, heteroaryl groups include 5 to 14 ring members, whereas other such groups have 5 to 6, 5 to 9, 5 to 10, 6 to 9, 6 to 10, or 6 to 14 ring members. For example, a 5-membered heteroaryl group has 5 ring members; a 6-membered heteroaryl group has 6 ring members; and a 9-membered heteroaryl group has 9 ring members (such as, but not limited to, benzothiophene). Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above. An azolyl group is a 5-membered heteroaryl group containing a nitrogen atom and at least one other atom selected from nitrogen, sulfur, and oxygen as part of the ring. Azolyl groups include imidazole, pyrazole, 1,2,3-triazole, 1,2,4-triazole, tetrazole, pentazole, oxazole, isoxazole, 1,2,4-oxadiazole, 1,2,5-oxadiazole, 1,3,4-oxadiazole, thiazole, isothiazole, 1,2,3-thiadiazole, 1,2,4-thiadiazole, 1,2,5-thiadiazole, and 1,3,4-thiadiazole.

As used herein, the term "alkyl" refers to an aliphatic hydrocarbon radical, which encompasses both straight and branched hydrocarbon radicals. In some embodiments, alkyl has from 1 to about 20 carbon atoms, from 1 to 12 carbons, from 1 to 8 carbons, 1 to 6 carbons, or 1 to 4 carbon atoms. For example, $C_{1-6}$ alkyl refers to an aliphatic hydrocarbon having 1 to 6 carbons, which includes methyl, ethyl, propyl, n-butyl, n-pentyl, n-hexyl, isopropyl, isobutyl, sec-butyl, tert-butyl, neopentyl, isopentyl, and the like.

As used herein, the term "hydroxy" is defined as —OH.

As used herein, the term "alkoxy," unless particularly defined herein, refers to a radical formed by substituting the hydrogen atom of a hydroxyl group with an alkyl. For example, $C_{1-6}$ alkoxy includes methoxy, ethoxy, propoxy, n-butoxy, n-pentyloxy, isopropoxy, sec-butoxy, tert-butoxy, neopentyloxy, isopentyloxy, and the like.

In addition, the term "halogen" refers to fluorine, bromine, chlorine, and iodine.

In addition, the term "amino" is defined as —NH$_2$, and the term "alkylamino" refers to a mono- or di-alkyl substituted amino. For example, $C_{1-6}$ alkylamino includes mono- or di-$C_{1-6}$ alkyl substituted amino.

In addition, the term "alkylthio" is defined as —SR (wherein R is alkyl), and the term "cyano" is defined as —CN.

Those of skill in the art will appreciate that compounds of the present technology may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the present technology encompasses any tautomeric, conformational isomeric, optical isomeric and/or geometric isomeric forms of the compounds having one or more of the utilities described herein, as well as mixtures of these various different forms. As used herein, "isomer" refers to a tautomer, conformation isomer, optical isomer, geometric isomer, or any combination thereof, of a compound. Structural isomers are not included in the meaning of "isomer" as used herein.

As readily understood by one skilled in the art, a wide variety of functional groups and other structures may exhibit tautomerism, and all tautomers of compounds as described herein are within the scope of the present technology.

Stereoisomers of compounds, also known as "optical isomers," include all chiral, diastereomeric, and racemic forms of a structure, unless the specific stereochemistry is expressly indicated. Thus, compounds used in the present technology include enriched or resolved optical isomers at any or all stereogenic atoms as are apparent from the depictions. Both racemic and diastereomeric mixtures, as well as the individual optical isomers can be isolated or synthesized so as to be substantially free of their enantiomeric or diastereomeric partners, and these are all within the scope of the present technology.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

Generally, reference to a certain moiety capable of being protected (such as hydroxy, amine, carbonyl, etc.) includes the protected groups in some embodiments of the disclosure. For example, in some embodiments, an —OH moiety as included herein also includes —OP, where P is a protecting group. Protecting groups, as referred to herein may be selected by one of ordinary skill in the art, and include the groups and strategies set forth in the art, for example, those such as described in R. Larock, *Comprehensive Organic Transformations*, VCH Publishers (1989); T. W. Greene and P. G. M. Wuts, *Greene's protective groups in organic synthesis*, John Wiley & Sons (2006); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

"Subject" refers to an animal, such as a mammal (including a human), that has been or will be the object of treatment, observation or experiment. "Subject" and "patient" may be used interchangeably, unless otherwise indicated. The methods described herein may be useful in human therapy and/or veterinary applications. In some embodiments, the subject is a mammal. In some embodiments, the subject is a human.

The terms "therapeutically effective amount" and "effective amount" are used interchangibly and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or care giver.

The term "treatment" or "treating" means administering a compound disclosed herein for the purpose of: (i) delaying the onset of a disease, that is, causing the clinical symptoms of the disease not to develop or delaying the development thereof, (ii) inhibiting the disease, that is, arresting the development of clinical symptoms; and/or (iii) relieving the disease, that is, causing the regression of clinical symptoms or the severity thereof.

Unless defined otherwise, all technical and scientific terms used herein have the same meaning as commonly understood by one of ordinary skill in the art to which this present technology belongs. Although any methods and materials similar or equivalent to those described herein can also be used in the practice or testing of the present technology, representative illustrative methods and materials are described herein.

The present technology provides a compound having inhibitory activity on VAP-1 or its salt, that is, a compound of Formula X

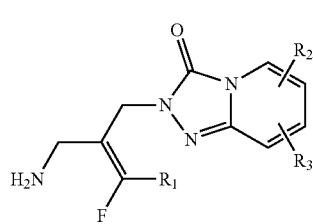

(Formula X)

or a stereoisomer thereof or a pharmaceutically acceptable salt thereof;
wherein
$R_1$ is hydrogen or fluoro; and
$R_2$ and $R_3$, each independently, are selected from the group consisting of hydrogen, halogen, $C_{1-6}$ alkyl, —R, and —C≡C—R;
wherein said R is substituted or unsubstituted cyclic ring, optionally containing 1 to 5 heteroatom ring members chosen from O, N, or S, and the cyclic ring is aromatic or non-aromatic.

In some embodiments of a compound of Formula X, R is substituted or unsubstituted aryl. In some embodiments of a compound of Formula X, R is substituted or unsubstituted phenyl. In some embodiments of a compound of Formula X, R is substituted or unsubstituted heteroaryl. In some embodiments of a compound of Formula X, R is substituted or unsubstituted non-aromatic heterocyclic.

In some embodiments of a compound of Formula X, the substituted or unsubstituted cyclic ring is selected from the group consisting of substituted or unsubstituted benzene, substituted or unsubstituted pyridine, substituted or unsubstituted tetrahydropyridine, substituted or unsubstituted pyrazole, substituted or unsubstituted benzodioxole, substituted or unsubstituted 2,3-dihydro benzodioxine, substituted or unsubstituted benzothiazole, substituted or unsubstituted benzoxadiazole, substituted or unsubstituted benzotriazole, substituted or unsubstituted indazole, substituted or unsubstituted pyrrolo[2,3-b]pyridine, substituted or unsubstituted 3,4-dihydroquinolin-2-one, substituted or unsubstituted 3,4-dihydro-1,4-benzoxazine, substituted or unsubstituted 1,4-benzoxazin-3-one, substituted or unsubstituted 1,3-dihydro-3,1-benzoxazin-2-one, substituted or unsubstituted 2,3-dihydro-pyrido[2,3-b][1,4]oxazine, substituted or unsubstituted pyrido[2,3-b][1,4]oxazin-2-one, substituted or unsubstituted 3,4-dihydro-pyrido[3,2-b][1,4]oxazine, and substituted or unsubstituted pyrido[3,2-b][1,4]oxazin-3-one.

In some embodiments of a compound of Formula X, $R_2$ and $R_3$ cannot be simultaneously hydrogen, halogen, $C_{1-6}$ alkyl, —R, or —C≡C—R. In some embodiments of a compound of Formula X, $R_2$ and $R_3$ cannot be simultaneously hydrogen, halogen, or $C_{1-6}$ alkyl. In some embodiments of a compound of Formula X, $R_2$ and $R_3$ cannot be simultaneously hydrogen. In some embodiments of a compound of Formula X, $R_2$ and $R_3$ cannot be simultaneously halogen. In some embodiments of a compound of Formula X, $R_2$ and $R_3$ cannot be simultaneously $C_{1-6}$ alkyl. In some embodiments of a compound of Formula X, $R_2$ and $R_3$ cannot be simultaneously —R or —C≡C—R. In some embodiments of a compound of Formula X, $R_2$ and $R_3$ cannot be simultaneously —R. In some embodiments of a compound of Formula X, $R_2$ and $R_3$ cannot be simultaneously —C≡C—R.

In another aspect, provided herein is a compound of Formula 1 below, or a stereoisomer thereof, or a pharmaceutically acceptable salt thereof:

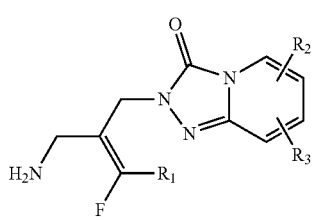

(Formula 1)

wherein
$R_1$ is hydrogen or fluoro,
$R_2$ and $R_3$, each independently, are selected from the group consisting of hydrogen, halogen, $C_{1-6}$ alkyl, —R, and —C≡C—R;
wherein $R_2$ and $R_3$ cannot be simultaneously hydrogen, halogen, $C_{1-6}$ alkyl, —R, or —C≡C—R;
wherein said R is a cyclic ring selected from the group consisting of benzene, pyridine, tetrahydropyridine, pyrazole, benzodioxole, 2,3-dihydrobenzodioxine, benzothiazole, benzoxadiazole, benzotriazole, indazole, pyrrolo[2,3-b]pyridine, 3,4-dihydroquinolin-2-one, 3,4-dihydro-1,4-benzoxazine, 1,4-benzoxazin-3-one, 1,3-dihydro-3,1-benzoxazin-2-one, 2,3-dihydro-pyrido[2,3-b][1,4]oxazine, pyrido[2,3-b][1,4]oxazin-2-one, 3,4-dihydro-pyrido[3,2-b][1,4]oxazine, and pyrido[3,2-b][1,4]oxazin-3-one;
wherein said cyclic ring is optionally substituted with a substituent selected from the group consisting of $C_{1-6}$ alkyl, trifluoromethyl, $C_{1-6}$ alkoxy, amino, mono- or di-$C_{1-6}$ alkylamino, di-$C_{1-6}$ alkylaminomethyl, $C_{1-6}$ alkylcarbonylamino, $C_{1-6}$ alkylsulfonyl, morpholinylsulfonyl, morpholinylcarbonyl, piperazinyl, morpholinyl, triazolyl, pyrazolyl, oxazolyl, oxadiazolyl, and cyclopropyl-oxadiazolyl.

In the compound of Formula 1 or, the stereoisomer thereof, or its pharmaceutically acceptable salt thereof according to the present technology, $R_1$ may preferably be fluoro. In some embodiments of a compound of Formula 1, $R_1$ is hydrogen.

In some embodiments of a compound of Formula 1, $R_2$ is hydrogen and $R_3$ is halogen, —R, or —C≡C—R.

Further, in the compound of Formula 1 or, the stereoisomer thereof, or its pharmaceutically acceptable salt thereof according to the present technology, $R_2$ and $R_3$, each independently, are selected from the group consisting of hydrogen, halogen, and —R, wherein $R_2$ and $R_3$ cannot be simultaneously hydrogen, halogen, or —R. In some embodiments, $R_2$ may be hydrogen and $R_3$ be halogen or —R. In some embodiments, $R_2$ is hydrogen and $R_3$ is halogen or —C≡C—R. In some embodiments, $R_2$ is hydrogen and $R_3$ is —R. In some embodiments, $R_2$ is hydrogen and $R_3$ is —C≡C—R In some embodiments of a compound of Formula 1, R is a cyclic ring selected from the group consisting of benzene and pyrazole. In some embodiments, said cyclic ring is substituted with a substituent selected from the group consisting of $C_{1-6}$ alkyl, $C_{1-6}$ alkylsulfonyl, and piperazinyl.

In some embodiments of a compound of Formula 1, $R_1$ is fluoro, $R_2$ is hydrogen, $R_3$ is halogen or —R, wherein said R is a cyclic ring selected from the group consisting of benzene and pyrazole, wherein said cyclic ring is substituted with a substituent selected from the group consisting of $C_{1-6}$ alkyl, $C_{1-6}$ alkylsulfonyl, and piperazinyl.

In the compound of Formula 1 or, the stereoisomer thereof, or its pharmaceutically acceptable salt thereof according to the present technology, R may preferably be selected from the group consisting of benzene, pyridine, tetrahydropyridine, pyrazole, benzodioxole, 2,3-dihydrobenzodioxine, benzothiazole, benzoxadiazole, benzotriazole, indazole, pyrrolo[2,3-b]pyridine, 3,4-dihydroquinolin-2-one, 3,4-dihydro-1,4-benzoxazine, 1,4-benzoxazin-3-one, and 1,3-dihydro-3,1-benzoxazin-2-one. More preferably, R may be a cyclic ring selected from the group consisting of benzene and pyrazole. Said cyclic ring may be substituted with a substituent selected from the group consisting of $C_{1-6}$ alkyl, $C_{1-6}$ alkylsulfonyl, and piperazinyl.

In some embodiments of a compound of Formula 1, $R_1$ is fluoro, $R_2$ is hydrogen, $R_3$ is halogen or —R, wherein R is a cyclic ring selected from the group consisting of benzene and pyrazole, wherein said cyclic ring is substituted with a substituent selected from the group consisting of $C_{1-6}$ alkyl, $C_{1-6}$ alkylsulfonyl, and piperazinyl, or a pharmaceutically acceptable salt thereof.

In another aspect, provided herein is a compound of Formula 11

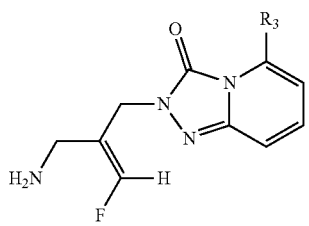

(Formula 11)

or a stereoisomer thereof or a pharmaceutically acceptable salt thereof; wherein $R_3$ is substituted or unsubstituted aryl, or substituted or unsubstituted heteroaryl.

In some embodiments of a compound of Formula 11, $R_3$ is substituted aryl. In some embodiments of a compound of Formula 11, $R_3$ is substituted phenyl. In some embodiments of a compound of Formula 11, $R_3$ is substituted or unsubstituted benzodioxole, substituted or unsubstituted benzoxadiazole, or phenyl, wherein the phenyl is substituted with $C_{1-6}$ alkylcarbonylamino or oxazolyl.

In another aspect, provided herein is a compound of Formula 12

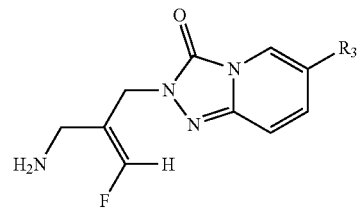

(Formula 12)

or a stereoisomer thereof or a pharmaceutically acceptable salt thereof; wherein $R_3$ is substituted or unsubstituted aryl, or substituted or unsubstituted heteroaryl. In some embodiments of a compound of Formula 12, $R_3$ is substituted or unsubstituted aryl. In some embodiments of a compound of Formula 12, $R_3$ is substituted or unsubstituted heteroaryl.

In some embodiments of a compound of Formula 12, $R_3$ is substituted or unsubstituted benzodioxole, substituted or unsubstituted 2,3-dihydrobenzodioxine, substituted or unsubstituted 3,4-dihydroquinolin-2-one, substituted or unsubstituted benzothiazole, substituted or unsubstituted benzoxadiazole, substituted benzene, or substituted pyridine. In some embodiments of a compound of Formula 12, the benzene or the pyridine is substituted with trifluoromethyl, amino, $C_{1-6}$ alkylcarbonylamino, $C_{1-6}$ alkylsulfonyl, morpholinylsulfonyl, morpholinyl, triazolyl, and oxazolyl.

In another aspect, provided herein is a compound of Formula 13

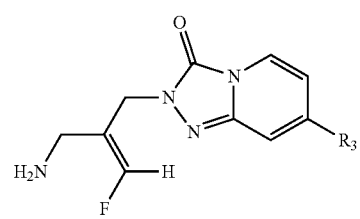

(Formula 13)

or a stereoisomer thereof or a pharmaceutically acceptable salt thereof; wherein $R_3$ is substituted or unsubstituted aryl, or a substituted or unsubstituted cyclic ring.

In some embodiments of a compound of Formula 13, $R_3$ is substituted or unsubstituted aryl. In some embodiments of a compound of Formula 13, $R_3$ is substituted or unsubstituted benzoxadiazole, substituted or unsubstituted 3,4-dihydroquinolin-2-one, substituted or unsubstituted benzodioxole, substituted or unsubstituted indazole, substituted or unsubstituted pyrazole, substituted or unsubstituted benzotriazole, substituted or unsubstituted 1,3-dihydro-3,1-benzoxazin-2-one, substituted or unsubstituted 1,4-benzoxazin-3-one, substituted or unsubstituted 3,4-dihydro-1,4-benzoxazine, or substituted phenyl.

In some embodiments of a compound of Formula 13, $R_3$ is phenyl substituted with di-$C_{1-6}$ alkylaminomethyl, $C_{1-6}$ alkylsulfonyl, morpholinylcarbonyl, pyrazolyl, oxazolyl, oxadiazolyl, piperazinyl, and cyclopropyl-oxadiazolyl In some embodiments of a compound of Formula 13, $R_3$ is a substituted or unsubstituted heterocyclic group. In some embodiments of a compound of Formula 13, $R_3$ is tetrahydropyridine.

In some embodiments of a compound of Formula 13, $R_3$ is substituted or unsubstituted heteroaryl. In some embodiments of a compound of Formula 13, $R_3$ is pyrrolo[2,3-b]pyridine or substituted pyridine. In some embodiments of a compound of Formula 13, $R_3$ is a pyridine substituted with trifluoromethyl, $C_{1-6}$ alkoxy, mono- or di-$C_{1-6}$ alkylamino, or morpholinyl.

In some embodiments of a compound of Formula 13, $R_3$ is a cyclic ring selected from the group consisting of benzene, pyridine, benzoxadiazole, 3,4-dihydroquinolin-2-one, benzodioxole, indazole, benzotriazole, 1,3-dihydro-3,1-benzoxazin-2-one, 1,4-benzoxazin-3-one, 3,4-dihydro-1,4-benzoxazine, or pyrrolo[2,3-b]pyridine; wherein said cyclic ring is optionally substituted with a substituent selected from the group consisting of $C_{1-6}$ alkyl, trifluoromethyl, $C_{1-6}$ alkoxy, mono- or di-$C_{1-6}$ alkylamino, di-$C_{1-6}$ alkylaminomethyl, $C_{1-6}$ alkylsulfonyl, morpholinylcarbonyl, morpholinyl, pyrazolyl, oxazolyl, oxadiazolyl, and cyclopropyl-oxadiazolyl.

In another aspect, provided herein is a compound of Formula 14

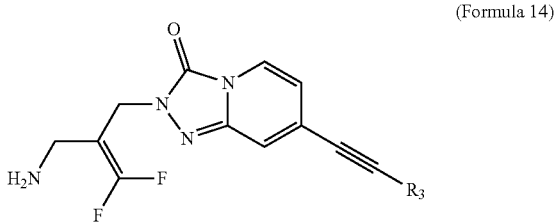

(Formula 14)

or a stereoisomer thereof or a pharmaceutically acceptable salt thereof; wherein $R_3$ is substituted or unsubstituted aryl, or substituted or unsubstituted heteroaryl.

In some embodiments of a compound of Formula 14, $R_3$ is substituted aryl.

In some embodiments of a compound of Formula 14, $R_3$ is substituted or unsubstituted 3,4-dihydroquinolin-2-one, or substituted or unsubstituted 3,4-dihydro-1,4-benzoxazine.

In some embodiments of a compound of Formula 14, $R_3$ is substituted or unsubstituted heteroaryl. In some embodiments of a compound of Formula 14, $R_3$ is substituted pyrazole, substituted pyridine, substituted or unsubstituted 2,3-dihydro-pyrido[2,3-b][1,4]oxazine, or substituted or unsubstituted 3,4-dihydro-pyrido[3,2-b][1,4]oxazine. In some embodiments of a compound of Formula 14, $R_3$ is pyridine substituted with mono- or di-$C_{1-6}$ alkylamino or morpholinyl.

The compounds provided in the description are inhibitors of VAP-1. VAP-1 inhibition may be measured, for example, by determining the half maximal inhibitory concentration ($IC_{50}$). One method for determining an $IC_{50}$ for VAP-1 is provided herein.

In one embodiment, the compounds are inhibitors of VAP-1. Selectivity may be determined, for example, by comparing inhibition of VAP-1 to inhibition of other aminooxidases such as MAO-A (monoamine oxidase-A), MAO-B (monoamine oxidase-B), and DAO (diamine oxidase). In one embodiment, said "significantly high inhibitory activity" means $IC_{50}$ for VAP-1 obtained from the in vitro enzyme analysis (in vitro enzyme assay) test is at least 3000 times lower than $IC_{50}$ of MAO-A, at least 100 times lower than $IC_{50}$ of MAO-B, or at least 100 times lower than $IC_{50}$ of DAO. In an alternative embodiment, "significantly high inhibitory activity" means the $IC_{50}$ for VAP-1 obtained from the in vitro enzyme analysis (in vitro enzyme assay) test is at least 3000 times lower than $IC_{50}$ of MAO-A, at least 100 times lower than $IC_{50}$ of MAO-B, and at least 100 times lower than $IC_{50}$ of DAO.

In another aspect, a compound of Formula X or Formula 1, or a stereoisomer thereof or a pharmaceutically acceptable salt thereof is selected from the following compounds or a pharmaceutically acceptable salt thereof:

2-[(2E)-2-(aminomethyl)-3-fluoroprop-2-en-1-yl]-6-bromo[1,2,4]triazolo[4,3-a]pyridin-3(2H)-one hydrochloride;

N-[4-[2-[(2E)-2-(aminomethyl)-3-fluoroprop-2-en-1-yl]-3-oxo-2,3-dihydro[1,2,4]triazolo[4,3-a]pyridin-6-yl]phenyl]acetamide;

2-[(2E)-2-(aminomethyl)-3-fluoroprop-2-en-1-yl]-6-[4-(methylsulfonyl)phenyl][1,2,4]triazolo[4,3-a]pyridin-3(2H)-one;

2-[(2E)-2-(aminomethyl)-3-fluoroprop-2-en-1-yl]-6-[4-(morpholin-4-ylsulfonyl)phenyl][1,2,4]triazolo[4,3-a]pyridin-3(2H)-one;

2-[(2E)-2-(aminomethyl)-3-fluoroprop-2-en-1-yl]-6-[4-(1H-1,2,4-triazol-3-yl)phenyl][1,2,4]triazolo[4,3-a]pyridin-3(2H)-one;

2-[(2E)-2-(aminomethyl)-3-fluoroprop-2-en-1-yl]-6-[3-(1H-1,2,4-triazol-3-yl)phenyl][1,2,4]triazolo[4,3-a]pyridin-3(2H)-one;

2-[(2E)-2-(aminomethyl)-3-fluoroprop-2-en-1-yl]-6-[4-(1,2-oxazol-3-yl)phenyl][1,2,4]triazolo[4,3-a]pyridin-3(2H)-one hydrochloride;

N-[4-[2-[(2E)-2-(aminomethyl)-3-fluoroprop-2-en-1-yl]-3-oxo-2,3-dihydro[1,2,4]triazolo[4,3-a]pyridin-6-yl]pyridin-2-yl]acetamide;

2-[(2E)-2-(aminomethyl)-3-fluoroprop-2-en-1-yl]-6-[6-(trifluoromethyl)pyridin-3-yl][1,2,4]triazolo[4,3-a]pyridin-3(2H)-one hydrochloride;

2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one;

2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one hydrochloride;

2-[(2E)-2-(aminomethyl)-3-fluoroprop-2-en-1-yl]-6-(1,3-benzodioxol-5-yl)[1,2,4]triazolo[4,3-a]pyridin-3(2H)-one hydrochloride;

2-[(2E)-2-(aminomethyl)-3-fluoroprop-2-en-1-yl]-6-(2,3-dihydro-1,4-benzodioxin-6-yl)[1,2,4]triazolo[4,3-a]pyridin-3(2H)-one;

6-(2-amino-1,3-benzothiazol-5-yl)-2-[(2E)-2-(aminomethyl)-3-fluoroprop-2-en-1-yl][1,2,4]triazolo[4,3-a]pyridin-3(2H)-one;

N-[5-[2-[(2E)-2-(aminomethyl)-3-fluoroprop-2-en-1-yl]-3-oxo-2,3-dihydro[1,2,4]triazolo[4,3-a]pyridin-6-yl]-1,3-benzothiazol-2-yl]acetamide;

2-[(2E)-2-(aminomethyl)-3-fluoroprop-2-en-1-yl]-6-(2,1,3-benzoxadiazol-5-yl)[1,2,4]triazolo[4,3-a]pyridin-3(2H)-one;

6-[2-[(2E)-2-(aminomethyl)-3-fluoroprop-2-en-1-yl]-3-oxo-2,3-dihydro[1,2,4]triazolo[4,3-a]pyridin-6-yl]-8-methyl-3,4-dihydroquinolin-2(1H)-one hydrochloride;

N-[4-[2-[(2E)-2-(aminomethyl)-3-fluoroprop-2-en-1-yl]-3-oxo-2,3-dihydro[1,2,4]triazolo[4,3-a]pyridin-5-yl]phenyl]acetamide;

2-[(2E)-2-(aminomethyl)-3-fluoroprop-2-en-1-yl]-5-[4-(1,2-oxazol-3-yl)phenyl][1,2,4]triazolo[4,3-a]pyridin-3(2H)-one;

2-[(2E)-2-(aminomethyl)-3-fluoroprop-2-en-1-yl]-5-(1,3-benzodioxol-5-yl)[1,2,4]triazolo[4,3-a]pyridin-3(2H)-one;

2-[(2E)-2-(aminomethyl)-3-fluoroprop-2-en-1-yl]-5-(2,1,3-benzoxadiazol-5-yl)[1,2,4]triazolo[4,3-a]pyridin-3(2H)-one;

2-[(2E)-2-(aminomethyl)-3-fluoroprop-2-en-1-yl]-7-[3-(methylsulfonyl)phenyl][1,2,4]triazolo[4,3-a]pyridin-3(2H)-one hydrochloride;

2-[(2E)-2-(aminomethyl)-3-fluoroprop-2-en-1-yl]-7-2-[(dimethylamino)methyl]phenyl[1,2,4]triazolo[4,3-a]pyridin-3(2H)-one hydrochloride;

2-[(2E)-2-(aminomethyl)-3-fluoroprop-2-en-1-yl]-7-[4-(morpholin-4-ylcarbonyl)phenyl][1,2,4]triazolo[4,3-a]pyridin-3(2H)-one hydrochloride;

2-[(2E)-2-(aminomethyl)-3-fluoroprop-2-en-1-yl]-7-[4-(1,2-oxazol-3-yl)phenyl][1,2,4]triazolo[4,3-a]pyridin-3(2H)-one hydrochloride;

2-[(2E)-2-(aminomethyl)-3-fluoroprop-2-en-1-yl]-7-[3-(1H-pyrazol-3-yl)phenyl][1,2,4]triazolo[4,3-a]pyridin-3(2H)-one hydrochloride;

2-[(2E)-2-(aminomethyl)-3-fluoroprop-2-en-1-yl]-7-[4-(1,2,5-oxadiazol-3-yl)phenyl][1,2,4]triazolo[4,3-a]pyridin-3(2H)-one hydrochloride;

2-[(2E)-2-(aminomethyl)-3-fluoroprop-2-en-1-yl]-7-[3-(5-cyclopropyl-1,2,4-oxadiazol-3-yl)phenyl][1,2,4]triazolo[4,3-a]pyridin-3(2H)-one hydrochloride;

2-[(2E)-2-(aminomethyl)-3-fluoroprop-2-en-1-yl]-7-[4-(5-cyclopropyl-1,2,4-oxadiazol-3-yl)phenyl][1,2,4]triazolo[4,3-a]pyridin-3(2H)-one hydrochloride;

2-[(2E)-2-(aminomethyl)-3-fluoroprop-2-en-1-yl]-7-[6-(trifluoromethyl)pyridin-3-yl][1,2,4]triazolo[4,3-a]pyridin-3(2H)-one hydrochloride;

2-[(2E)-2-(aminomethyl)-3-fluoroprop-2-en-1-yl]-7-(6-methoxypyridin-3-yl)[1,2,4]triazolo[4,3-a]pyridin-3(2H)-one hydrochloride;

2-[(2E)-2-(aminomethyl)-3-fluoroprop-2-en-1-yl]-7-[6-(dimethylamino)pyridin-3-yl][1,2,4]triazolo[4,3-a]pyridin-3(2H)-one hydrochloride;

2-[(2E)-2-(aminomethyl)-3-fluoroprop-2-en-1-yl]-7-[6-(morpholin-4-yl)pyridin-3-yl][1,2,4]triazolo[4,3-a]pyridin-3(2H)-one hydrochloride;

2-[(2E)-2-(aminomethyl)-3-fluoroprop-2-en-1-yl]-7-(1,2,3,6-tetrahydropyridin-4-yl)[1,2,4]triazolo[4,3-a]pyridin-3(2H)-one hydrochloride;

2-[(2E)-2-(aminomethyl)-3-fluoroprop-2-en-1-yl]-7-(1H-pyrrolo[2,3-b]pyridin-3-yl)[1,2,4]triazolo[4,3-a]pyridin-3(2H)-one hydrochloride;

2-[(2E)-2-(aminomethyl)-3-fluoroprop-2-en-1-yl]-7-(1,3-benzodioxol-5-yl)[1,2,4]triazolo[4,3-a]pyridin-3(2H)-one hydrochloride;

2-[(2E)-2-(aminomethyl)-3-fluoroprop-2-en-1-yl]-7-(1H-indazol-6-yl)[1,2,4]triazolo[4,a]pyridin-3(2H)-one hydrochloride;

2-[(2E)-2-(aminomethyl)-3-fluoroprop-2-en-1-yl]-7-(2,1,3-benzoxadiazol-5-yl)[1,2,4]triazolo[4,3-a]pyridin-3(2H)-one hydrochloride;

2-[(2E)-2-(aminomethyl)-3-fluoroprop-2-en-1-yl]-7-(1H-benzotriazol-6-yl)[1,2,4]triazolo[4,3-a]pyridin-3(2H)-one hydrochloride;

2-[(2E)-2-(aminomethyl)-3-fluoroprop-2-en-1-yl]-7-(1H-pyrrolo[2,3-b]pyridin-4-yl)[1,2,4]triazolo[4,3-a]pyridin-3(2H)-one hydrochloride;

7-[2-[(2E)-2-(aminomethyl)-3-fluoroprop-2-en-1-yl]-3-oxo-2,3-dihydro[1,2,4]triazolo[4,3-a]pyridin-7-yl]-1,4-dihydro-2H-3,1-benzoxazin-2-one hydrochloride;

6-[2-[(2E)-2-(aminomethyl)-3-fluoroprop-2-en-1-yl]-3-oxo-2,3-dihydro[1,2,4]triazolo[4,3-a]pyridin-7-yl]-2H-1,4-benzoxazine-3(4H)-one hydrochloride;

6-[2-[(2E)-2-(aminomethyl)-3-fluoroprop-2-en-1-yl]-3-oxo-2,3-dihydro[1,2,4]triazolo[4,3-a]pyridin-7-yl]-8-methyl-3,4-dihydroquinolin-2(1H)-one hydrochloride;

2-[(2E)-2-(aminomethyl)-3-fluoroprop-2-en-1-yl]-7-(4-methyl-3,4-dihydro-2H-1,4-benzoxazin-7-yl)[1,2,4]triazolo[4,3-a]pyridin-3(2H)-one hydrochloride;

2-[2-(aminomethyl)-3,3-difluoro-allyl]-5-bromo-[1,2,4]triazolo[4,3-a]pyridin-3-one;

2-[2-(aminomethyl)-3,3-difluoro-allyl]-6-bromo-[1,2,4]triazolo[4,3-a]pyridin-3-one;

2-[2-(aminomethyl)-3,3-difluoro-allyl]-7-bromo-[1,2,4]triazolo[4,3-a]pyridin-3-one;

2-[2-(aminomethyl)-3,3-difluoro-allyl]-7-(4-methylsulfonylphenyl)-[1,2,4]triazolo[4,3-a]pyridin-3-one;

2-[2-(aminomethyl)-3,3-difluoro-allyl]-7-(4-piperazin-1-ylphenyl)-[1,2,4]triazolo[4,3-a]pyridin-3-one;

2-[2-(aminomethyl)-3,3-difluoro-allyl]-7-[6-(trifluoromethyl)-3-pyridyl]-[1,2,4]triazolo[4,3-a]pyridin-3-one;

2-[2-(aminomethyl)-3,3-difluoro-allyl]-7-[6-(dimethylamino)-3-pyridyl]-[1,2,4]triazolo[4,3-a]pyridin-3-one;

2-[2-(aminomethyl)-3,3-difluoro-allyl]-7-(1,3-benzodioxol-5-yl)-[1,2,4]triazolo[4,3-a]pyridin-3-one;

6-[2-[2-(aminomethyl)-3,3-difluoro-allyl]-3-oxo-[1,2,4]triazolo[4,3-a]pyridin-7-yl]-8-methyl-3,4-dihydro-1H-quinolin-2-one;

6-[2-[2-(aminomethyl)-3,3-difluoro-allyl]-3-oxo-[1,2,4]triazolo[4,3-a]pyridin-7-yl]-1-methyl-3,4-dihydroquinolin-2-one;

2-[2-(aminomethyl)-3,3-difluoro-allyl]-7-(1-ethylpyrazol-4-yl)-[1,2,4]triazolo[4,3-a]pyridin-3-one;

2-[2-(aminomethyl)-3,3-difluoro-allyl]-7-[2-(1-methylpyrazol-4-yl)ethynyl]-[1,2,4]triazolo[4,3-a]pyridin-3-one;

2-[2-(aminomethyl)-3,3-difluoro-allyl]-7-[2-[6-(dimethylamino)-3-pyridyl]ethynyl]-[1,2,4]triazolo[4,3-a]pyridin-3-one;

2-[2-(aminomethyl)-3,3-difluoro-allyl]-7-[2-(6-morpholino-3-pyridyl)ethynyl]-[1,2,4]triazolo[4,3-a]pyridin-3-one;

2-[2-(aminomethyl)-3,3-difluoro-allyl]-7-[2-(3,4-dihydro-2H-1,4-benzoxazin-6-yl)ethynyl]-[1,2,4]triazolo[4,3-a]pyridin-3-one;

2-[2-(aminomethyl)-3,3-difluoro-allyl]-7-[2-(2,3-dihydro-1H-pyrido[2,3-b][1,4]oxazin-7-yl)ethynyl]-[1,2,4]triazolo[4,3-a]pyridin-3-one;

2-[2-(aminomethyl)-3,3-difluoro-allyl]-7-[2-(3,4-dihydro-2H-pyrido[3,2-b][1,4]oxazin-7-yl)ethynyl]-[1,2,4]triazolo[4,3-a]pyridin-3-one;

6-[2-[2-[2-(aminomethyl)-3,3-difluoro-allyl]-3-oxo-[1,2,4]triazolo[4,3-a]pyridin-7-yl]ethynyl]-3,4-dihydro-1H-quinolin-2-one; and 2-[2-(aminomethyl)-3,3-difluoro-allyl]-7-[2-(4-methyl-2,3-dihydro-1,4-benzoxazin-7-yl)ethynyl]-[1,2,4]triazolo[4,3-a]pyridin-3-one.

As for the compound of Formula 1 or the stereoisomer thereof or its pharmaceutically acceptable salt, the more preferred compound may be a compound selected from the group consisting of the following compounds or a pharmaceutically acceptable salt thereof:

2-[2-(aminomethyl)-3,3-difluoro-allyl]-7-bromo-[1,2,4]triazolo[4,3-a]pyridin-3-one; and 2-[2-(aminomethyl)-3,3-difluoro-allyl]-7-(1-ethylpyrazol-4-yl)-[1,2,4]triazolo[4,3-a]pyridin-3-one.

The compound of Formula 1 or a pharmaceutically acceptable salt thereof may exist as the geometric isomer of a cis or trans structure. Thus, unless indicated otherwise, the compound of Formula 1 or salts thereof comprise both geometric isomers of cis and trans structures.

The compound of Formula 1 of the present technology can be in the form of a pharmaceutically acceptable salt. The term "pharmaceutically acceptable salt," as used herein, represents salts or zwitterionic forms of the compounds of the present technology which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by, for example, reacting the appropriate compound in the form of the free base with a suitable acid. Such salts include conventional acid addition salts, e.g., a salt derived from inorganic acid such as hydrochloric acid, bromic acid, sulfuric acid, sulfamic acid, phosphoric acid, or nitric acid and a salt derived from organic acid such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, p-toluenesulfonic acid, oxalic acid or trifluoroacetic acid. Further, said salts include conventional metal salt types, e.g., a salt derived from a metal such as lithium, sodium, potassium, magnesium, or calcium. Said acid addition salt or metal salt can be prepared according to conventional methods.

The compound of Formula 1 or a stereoisomer thereof or a salt thereof according to the present technology may be prepared by various methods. For example, the compound of Formula 1a or a stereoisomer thereof or a pharmaceutically acceptable salt thereof according to the present technology can be prepared by a preparation process comprising the step of reacting a compound of Formula 2 with a compound of Formula 3a or a compound of Formula 3b to obtain a compound of Formula 1 aa and the step of deprotecting said compound of Formula 1 aa.

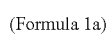
(Formula 1a)
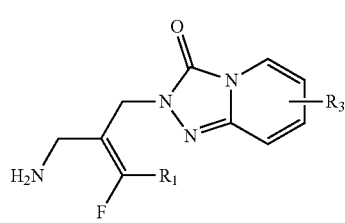

(Formula 1aa)
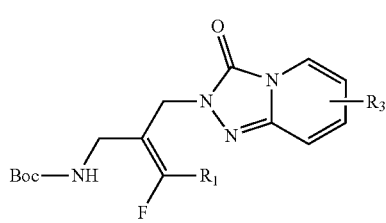

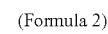
(Formula 2)
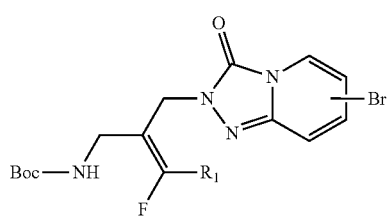

$$Z-R_3 \quad \text{(Formula 3a)}$$
$$HC\equiv CR \quad \text{(Formula 3b)}$$

In said Formulae 1a, 1aa, 2, 3a, and 3b, Boc is an amine protecting group (e.g., tert-butoxycarbonyl, 9-fluorenylmethyloxycarbonyl (FMOC), benzyloxycarbonyl(CBZ), triphenylmethyl(trityl), etc.) and Z is boronic acid ($B(OH)_2$) or boronic acid pinacol ester, and R, $R_1$, and $R_3$ are the same as defined above.

The reaction of the compound of Formula 2 above with a commercially available compound of Formula 3a may be carried out via Suzuki reaction. Said reaction can be carried out by using a palladium catalyst. The palladium catalyst includes palladium diacetate ($Pd(OAc)_2$), tris(dibenzylideneacetone)dipalladium ($Pd_2(dba)_3$), tetrakis(triphenylphosphine)palladium ($Pd(PPh_3)_4$) or palladiumdi[1,1'-bis(diphenylphosphino)ferrocene]dichloride ($PdCl_2(dppf)_2$), etc. In the reaction carried out under a palladium catalyst, a ligand and a base can be added in addition to the palladium catalyst. Said ligand includes (S)-2,2-bis(diphenylphospino)-1,1-binaphthyl (BINAP), 1,1'-bis(diphenylphospino)ferrocene (dppf), (tri-O-tolyl)phosphine ($P(O-Tol)_3$), or the like and said base includes an inorganic base such as cesium carbonate ($Cs_2CO_3$), sodium carbonate ($Na_2CO_3$), potassium carbonate ($K_2CO_3$), potassium fluoride (KF), cesium fluoride (CsF), sodium hydroxide (NaOH), potassium phosphonate ($K_3PO_4$), sodium tert-butoxide (tert-BuONa), potassium tert-butoxide (tert-BuOK), or the like.

The reaction may be carried out in a non-polar organic solvent such as benzene or toluene, or a polar solvent such as dioxane, tetrahydrofuran, acetonitrile, 1,2-dimethoxyethane, N,N-dimethylformamide, or the like, at a temperature ranging from 50° C. to 150° C., preferably from 80° C. to 110° C. Other reaction conditions, including e.g., reaction time, may be determined from the reaction conditions for conventional Suzuki reaction (Barbara Czako and Laszlo Kurti, *STRATEGIC APPLICATIONS of NAMED REACTIONS in ORGANIC SYNTHESIS*, 2005).

Further, the reaction of the compound of Formula 2 and the commercially available compound of Formula 3b (i.e., an ethyne derivative) can be carried out via Sonogashira coupling reaction using a palladium reagent such as bis(triphenylphosphine)palladium(II) dichloride, tetrakis(triphenylphosphine)palladium(0), etc., and a copper iodide. The coupling reaction may be carried out at room temperature or at a heated temperature, e.g., a temperature ranging from 20° C. to 60° C. In addition, in order to improve reaction rate and reaction yield, said coupling reaction can be carried out in the presence of a base such as a diisopropylamine, a triethylamine, etc., and a ligand such as triphenylphosphine or the like.

Deprotection of the compound of Formula 1aa can be carried out by conventional methods of removing an amine protecting group. For example, said deprotection can be carried out by removing the amine protecting group in the form of a free amine or by removing it in the form of a hydrochloride salt by using hydrogen chloride dissolved in an organic solvent, such as diethyl ether, 1,4-dioxane, etc.

The compound of Formula 2 can be prepared according to the following Reaction Scheme 1.

Reaction Scheme 1.

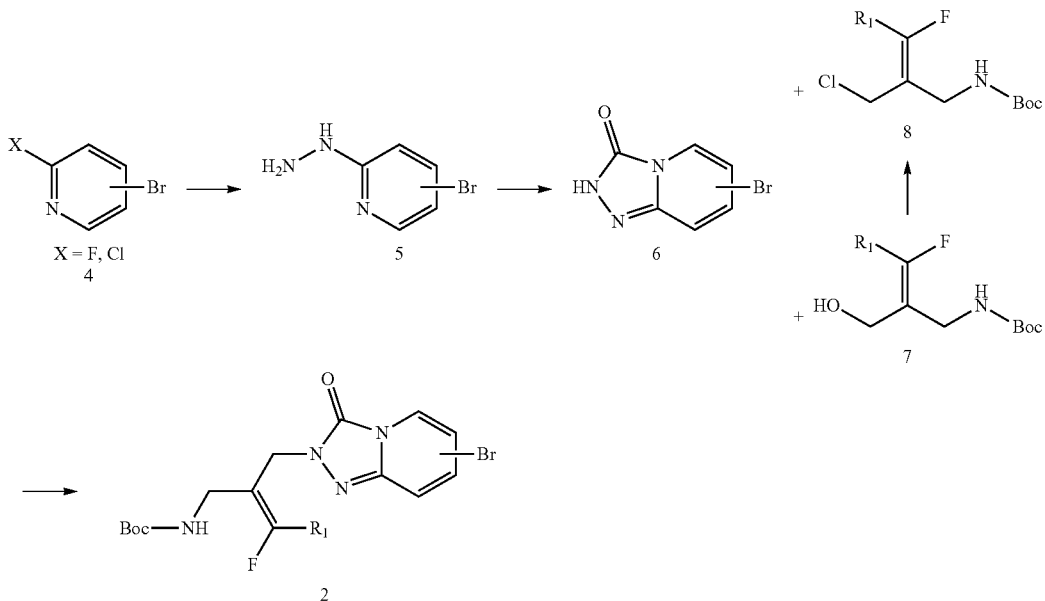

In Reaction Scheme 1, R₁ and Boc are the same as defined above.

A compound of Formula 4 is commercially available. The compound of Formula 4 can be converted to a compound of Formula 5 via reaction with hydrazine. Said hydrazine introduction reaction can be carried out in a solvent such as tetrahydrofuran, etc., at about 70° C. (e.g., WO2015/014283, etc.).

The compound of Formula 5 can be converted to a compound of Formula 6 via cyclization reaction. Said cyclization reaction can be carried out by using carbonyldiimidazole (CDI) in a polar solvent such as tetrahydrofuran or acetonitrile, etc. at a temperature ranging from room temperature to 90° C. (e.g., WO 2015/014283, etc.).

The compound of Formula 6 can be converted to a compound of Formula 2 via Mitsunobu reaction with a compound of Formula 7 or via coupling reaction with a compound of Formula 8.

The reaction of the compound of Formula 6 above with the compound of Formula 7 can be carried out via Mitsunobu reaction. For example, said reaction can be carried out in the presence of triphenylphosphine or trin-butylphosphine using diethyl azodicarboxylate (DEAD) or diisopropyl azodicarboxylate (DIAD). The reaction solvent may be a polar organic solvent such as dichloromethane, dioxane, tetrahydrofuran, dimethylformamide, etc. The reaction may be carried out at 0° C. to room temperature, and can be carried out at a higher temperature on occasion. Other reaction conditions including reaction time may be determined from the reaction conditions for conventional Mitsunobu reaction (Barbara Czako and Laszlo Kurti, STRATEGIC APPLICATIONS of NAMED REACTIONS in ORGANIC SYNTHESIS, 2005).

The coupling reaction of the compound of Formula 6 with the compound of Formula 8 can be carried out in the presence of a base and a solvent. Said base may be cesium carbonate, potassium carbonate, sodium carbonate, etc. and said solvent may be an organic solvent such as N,N-dimethylformamide, dioxane, tetrahydrofuran, etc. Further, said reaction can be carried out at room temperature to 100° C.

The compound of Formula 8 can be obtained from the chlorination reaction of the compound of Formula 7. Said chlorination reaction can be carried out in the presence of conventional inorganic bases and organic solvents.

A compound of Formula 7, wherein R₁ is hydrogen, (the compound of Formula 7a) is commercially available and a compound of Formula 7, wherein R₁ is fluoro (the compound of Formula 7b) can be prepared according to Reaction Scheme 2 below.

Reaction Scheme 2.

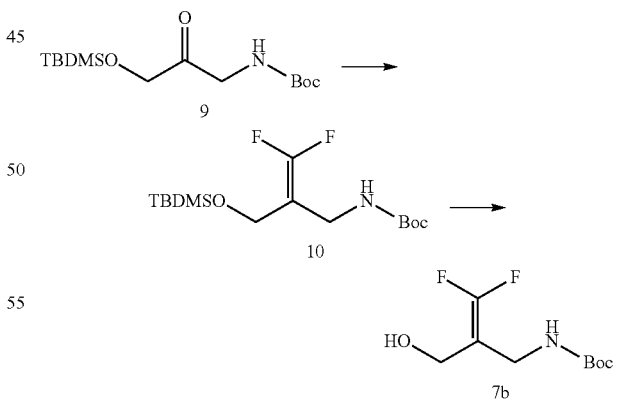

In Reaction Scheme 2, TBDMS is tert-butyldimethylsilyl, which is a hydroxyl protecting group and Boc is the same as defined in the above.

A compound of Formula 9 is commercially available and can be prepared according to known methods (e.g., WO 2013/163675, etc.). The compound of Formula 9 can be converted to a compound of Formula 10 via gem-difluoroolefination reaction. The gem-difluoroolefination reaction can be carried out in the presence of a base such as potassium tert-butoxide (tert-BuOK), lithium bis(trimethylsilyl)amide (LiHMDS), or the like using a fluorinated sulfone such as difluoromethyl2-pyridyl sulfone. The reaction solvent may be an organic solvent such as N,N-dimethylformamide, tetrahydrofuran, or the like and the reaction can be carried out at a temperature between −40° C.-0° C. (Yanchuan Zhao; Weizhou Huang; Lingui Zhu; Jinbo Hu, *Organic Letters*, 12, pp. 1444-1447, 2010).

The compound of Formula 10 can be converted to the compound of Formula 7b via deprotection reaction of a hydroxyl protecting group (TBDMS). The deprotection reaction of a hydroxyl protecting group can be carried out according to known methods (Theodora W. Greene and Peter G. M. Wuts, *Protective groups in organic synthesis*, 3rd Ed., 1999). For example, the deprotection reaction of a hydroxyl protecting group (TBDMS) can be carried out at room temperature in a solvent such as dichloromethane, tetrahydrofuran, or the like, using an organic salt such as tetrabutylamoniumfluoride (TBAF), etc. W. Green; P. G. M. Wuts, *Protective Groups in Organic Synthesis*, 127-141, 708-711, 1999).

The triazolopyridin-3-ones according to the present technology, i.e., a compound of Formula 1, or a stereoisomer thereof, or a pharmaceutically acceptable salt thereof, have a inhibitory activity on VAP-1, and thus can be usefully applied in the prevention or treatment of a VAP-1 mediated disease. Preferably, the compound of Formula 1 according to the present technology, or a stereoisomer thereof, or a pharmaceutically acceptable salt thereof can be usefully applied for the prevention of treatment of nonalcoholic steatohepatitis (NASH).

In some embodiments, provided herein is the use of the triazolopyridin-3-ones according to the present technology, i.e., the compound of Formula 1, or a stereoisomer thereof, or a pharmaceutically acceptable salt thereof, in the preparation of a medicament for the prophylaxis and/or treatment of lipid and lipoprotein disorders (such as, but not limited to, hypercholesterolemia, hypertriglyceridemia, and atherosclerosis), of conditions and diseases which result from chronic fatty and fibrotic degeneration of organs due to accumulated lipid and specifically triglyceride accumulation and subsequent activation of profibrotic pathways (such as, but not limited to, NASH and chronic cholestatic conditions in the liver, Glomerulosclerosis and Diabetic Nephropathy in the kidney, Macular Degeneration and Diabetic Retinopathy in the eye and neurodegenerative diseases, such as Alzheimer's Disease in the brain, or Diabetic Neuropathies in the peripheral nervous system), of Type I or Type II Diabetes and clinical complications of Type I and Type II Diabetes (such as, but not limited to, Diabetic Nephropathy, Diabetic Retinopathy, Diabetic Neuropathies, or Peripheral Arterial Occlusive Disease (PAOD)), of chronic intrahepatic or some forms of extrahepatic cholestatic conditions, of liver fibrosis, of acute intraheptic cholestatic conditions, of obstructive or chronic inflammatory disorders that arise out of improper bile composition (such as, but not limited to, cholelithiasis also known as cholesterol gallstones), of gastrointestinal conditions with a reduced uptake of dietary fat and fat-soluble dietary vitamins, of inflammatory bowel diseases, of obesity and metabolic syndrome (combined conditions of dyslipidemia, diabetes and abnormally high body-mass index), of persistent infections by intracellular bacteria or parasitic protozoae, of non-malignant hyperproliferative disorders, of malignant hyperproliferative disorders (such as, but not limited to, different forms of cancer, specifically certain forms of breast, liver or colon cancer, or a disorder selected from the group consisting of hepatocellular carcinoma, colon adenoma, and polyposis), of colon adenocarcinoma and hepatocellular carcinoma in particular, of liver steatosis and associated syndromes, of Hepatitis B infection, of Hepatitis C infection and/or of cholestatic and fibrotic effects that are associated with alcohol-induced cirrhosis or with viral-borne forms of hepatitis, of liver failure or liver malfunction as an outcome of chronic liver diseases or of surgical liver resection, of acute myocardial infarction, of acute stroke, of thrombosis which occurs as an endpoint of chronic obstructive atherosclerosis, of osteoarthritis, of rheumatoid arthritis, of psoriasis, or of cerebral infarction, individually or of any combination thereof.

In some embodiments, the compounds and/or pharmaceutical compositions disclosed herein are used for prophylaxis and/or treatment of chronic intrahepatic conditions, such as Primary Biliary Cirrhosis (PBC), Primary Sclerosing Cholangitis (PSC), progressive familiar cholestasis (PFIC), alcohol-induced cirrhosis and associated cholestasis, and some forms of extrahepatic cholestatic conditions, or liver fibrosis.

In some embodiments, provided herein is a method to treat chronic intrahepatic conditions and/or some forms of extrahepatic cholestatic conditions in a patient in need thereof, the method comprising, consisting essentially of, or consisting of administering to the patient a therapeutically effective amount of a compound or a composition disclosed herein. In some embodiments, the chronic intrahepatic conditions are selected from PBC, PSC, PFIC, and alcohol-induced cirrhosis and associated cholestasis.

In some embodiments, provided herein is a method to treat liver fibrosis in a patient in need thereof, the method comprising, consisting essentially of, or consisting of administering to the patient a therapeutically effective amount of a compound or a composition disclosed herein.

In some embodiments, provided herein is a method to treat a lipid and lipoprotein disorder in a patient in need thereof, the method comprising, consisting essentially of, or consisting of administering to the patient a therapeutically effective amount of a compound or a composition disclosed herein. In some embodiments, the lipid and lipoprotein disorder is selected from hypercholesterolemia, hypertriglyceridemia, and atherosclerosis.

In some embodiments, provided herein is a method to treat a condition or disease which results from chronic fatty and fibrotic degeneration of organs due to accumulated lipid and specifically triglyceride accumulation and subsequent activation of profibrotic pathways in a patient in need thereof, the method comprising, consisting essentially of, or consisting of administering to the patient a therapeutically effective amount of a compound or a composition disclosed herein. In some embodiments, the condition or disease which results from chronic fatty and fibrotic degeneration of organs due to accumulated lipid and specifically triglyceride accumulation and subsequent activation of profibrotic pathways is selected from NASH and chronic cholestatic conditions in the liver, Glomerulosclerosis and Diabetic Nephropathy in the kidney, Macular Degeneration and Diabetic Retinopathy in the eye, and neurodegenerative diseases. In some further embodiments, neurodegenerative diseases are selected from Alzheimer's Disease in the brain, and Diabetic Neuropathies in the peripheral nervous system.

In some embodiments, provided herein is a method to treat Type I or Type II Diabetes and clinical complications of Type I and Type II Diabetes in a patient in need thereof, the method comprising, consisting essentially of, or consisting of administering to the patient a therapeutically effective amount of a compound or a composition disclosed herein. In some embodiments, provided herein is a method to treat Type I Diabetes in a patient in need thereof, the method comprising, consisting essentially of, or consisting of administering to the patient a therapeutically effective amount of a compound or a composition disclosed herein. In some embodiments, provided herein is a method to treat Type II Diabetes in a patient in need thereof, the method comprising, consisting essentially of, or consisting of administering to the patient a therapeutically effective amount of a compound or a composition disclosed herein. In some embodiments, provided herein is a method to treat one or more clinical complications of Type I and Type II Diabetes in a patient in need thereof, the method comprising, consisting essentially of, or consisting of administering to the patient a therapeutically effective amount of a compound or a composition disclosed herein. In some embodiments, the clinical complications of Type I and Type II Diabetes are selected from Diabetic Nephropathy, Diabetic Retinopathy, Diabetic Neuropathies, and Peripheral Arterial Occlusive Disease (PAOD), or any combination thereof.

In some embodiments, provided herein is a method to treat acute intraheptic cholestatic conditions in a patient in need thereof, the method comprising, consisting essentially of, or consisting of administering to the patient a therapeutically effective amount of a compound or a composition disclosed herein.

In some embodiments, provided herein is a method to treat obstructive or chronic inflammatory disorders that arise out of improper bile composition in a patient in need thereof, the method comprising, consisting essentially of, or consisting of administering to the patient a therapeutically effective amount of a compound or a composition disclosed herein. In some embodiments, the obstructive or chronic inflammatory disorders that arise out of improper bile composition is cholelithiasis also known as cholesterol gallstones.

In some embodiments, provided herein is a method to treat gastrointestinal conditions with a reduced uptake of dietary fat and fat-soluble dietary vitamins in a patient in need thereof, the method comprising, consisting essentially of, or consisting of administering to the patient a therapeutically effective amount of a compound or a composition disclosed herein.

In some embodiments, provided herein is a method to treat inflammatory bowel diseases in a patient in need thereof, the method comprising, consisting essentially of, or consisting of administering to the patient a therapeutically effective amount of a compound or a composition disclosed herein.

In some embodiments, provided herein is a method to treat obesity and metabolic syndrome in a patient in need thereof, the method comprising, consisting essentially of, or consisting of administering to the patient a therapeutically effective amount of a compound or a composition disclosed herein.

In some embodiments, provided herein is a method to treat persistent infections by intracellular bacteria or parasitic protozoae in a patient in need thereof, the method comprising, consisting essentially of, or consisting of administering to the patient a therapeutically effective amount of a compound or a composition disclosed herein.

In some embodiments, provided herein is a method to treat non-malignant hyperproliferative disorders in a patient in need thereof, the method comprising, consisting essentially of, or consisting of administering to the patient a therapeutically effective amount of a compound or a composition disclosed herein.

In some embodiments, provided herein is a method to treat malignant hyperproliferative disorders in a patient in need thereof, the method comprising, consisting essentially of, or consisting of administering to the patient a therapeutically effective amount of a compound or a composition disclosed herein. In some embodiments, malignant hyperproliferative disorders are selected from different forms of cancer, specifically certain forms of breast, liver or colon cancer, or a disorder selected from the group consisting of hepatocellular carcinoma, colon adenoma, and polyposis.

In some embodiments, provided herein is a method to treat colon adenocarcinoma in a patient in need thereof, the method comprising, consisting essentially of, or consisting of administering to the patient a therapeutically effective amount of a compound or a composition disclosed herein.

In some embodiments, provided herein is a method to treat hepatocellular carcinoma in a patient in need thereof, the method comprising, consisting essentially of, or consisting of administering to the patient a therapeutically effective amount of a compound or a composition disclosed herein.

In some embodiments, provided herein is a method to treat liver steatosis and associated syndromes in a patient in need thereof, the method comprising, consisting essentially of, or consisting of administering to the patient a therapeutically effective amount of a compound or a composition disclosed herein.

In some embodiments, provided herein is a method to treat Hepatitis B infection in a patient in need thereof, the method comprising, consisting essentially of, or consisting of administering to the patient a therapeutically effective amount of a compound or a composition disclosed herein.

In some embodiments, provided herein is a method to treat Hepatitis C infection in a patient in need thereof, the method comprising, consisting essentially of, or consisting of administering to the patient a therapeutically effective amount of a compound or a composition disclosed herein.

In some embodiments, provided herein is a method to treat cholestatic and fibrotic effects that are associated with alcohol-induced cirrhosis or with viral-borne forms of hepatitis in a patient in need thereof, the method comprising, consisting essentially of, or consisting of administering to the patient a therapeutically effective amount of a compound or a composition disclosed herein.

In some embodiments, provided herein is a method to treat liver failure or liver malfunction as an outcome of chronic liver diseases or of surgical liver resection in a patient in need thereof, the method comprising, consisting essentially of, or consisting of administering to the patient a therapeutically effective amount of a compound or a composition disclosed herein.

In some embodiments, provided herein is a method to treat acute myocardial infarction in a patient in need thereof, the method comprising, consisting essentially of, or consisting of administering to the patient a therapeutically effective amount of a compound or a composition disclosed herein.

In some embodiments, provided herein is a method to treat acute stroke in a patient in need thereof, the method comprising, consisting essentially of, or consisting of administering to the patient a therapeutically effective amount of a compound or a composition disclosed herein.

In some embodiments, provided herein is a method to treat thrombosis which occurs as an endpoint of chronic obstructive atherosclerosis in a patient in need thereof, the method comprising, consisting essentially of, or consisting of administering to the patient a therapeutically effective amount of a compound or a composition disclosed herein.

In some embodiments, provided herein is a method to treat osteoarthritis in a patient in need thereof, the method comprising, consisting essentially of, or consisting of administering to the patient a therapeutically effective amount of a compound or a composition disclosed herein.

In some embodiments, provided herein is a method to treat rheumatoid arthritis in a patient in need thereof, the method comprising, consisting essentially of, or consisting of administering to the patient a therapeutically effective amount of a compound or a composition disclosed herein.

In some embodiments, provided herein is a method to treat psoriasis in a patient in need thereof, the method comprising, consisting essentially of, or consisting of administering to the patient a therapeutically effective amount of a compound or a composition disclosed herein.

In some embodiments, provided herein is a method to treat cerebral infarction in a patient in need thereof, the method comprising, consisting essentially of, or consisting of administering to the patient a therapeutically effective amount of a compound or a composition disclosed herein.

Thus, the present technology includes a pharmaceutical composition for inhibiting vascular adhesion protein-1 (VAP-1), comprising a therapeutically effective amount of a compound of Formula 1 or a stereoisomer thereof or a pharmaceutically acceptable salt thereof as an active ingredient. In one embodiment, the present technology provides a pharmaceutical composition for preventing or treating nonalcoholic steatohepatitis (NASH), comprising a therapeutically effective amount of a compound of Formula 1, or a stereoisomer thereof, or a pharmaceutically acceptable salt thereof as an active ingredient. In some embodiments, provided herein is a pharmaceutical composition for preventing or treating NASH comprising, consisting essentially of, or consisting of a therapeutically effective amount of a compound of Formula 1, or a stereoisomer thereof, or a pharmaceutically acceptable salt thereof, and at least one pharmaceutically acceptable carrier or excipient.

In another aspect, the present technology provides a pharmaceutical composition for preventing or treating diabetic nephropathy comprising, consisting essentially of, or consisting of a therapeutically effective amount of a compound of Formula 1, or a stereoisomer thereof, or a pharmaceutically acceptable salt thereof, and at least one pharmaceutically acceptable carrier or excipient.

In another aspect, the present technology provides a pharmaceutical composition for preventing or treating primary sclerosing cholangitis comprising, consisting essentially of, or consisting of a therapeutically effective amount of a compound of Formula 1, or a stereoisomer thereof, or a pharmaceutically acceptable salt thereof, and at least one pharmaceutically acceptable carrier or excipient.

In some embodiments, the compounds of the present disclosure may be combined with one or more additional therapies for the prevention or treatment of a disease or condition amenable to treatment by inhibition of VAP-1.

In some embodiments, the compositions disclosed herein contain at least one additional active agent.

Exemplary additional active agents include, but are not limited, one or more of a(n) ACE inhibitor, Acetyl CoA carboxylase inhibitor, Adenosine A3 receptor agonist, Adiponectin receptor agonist, AKT protein kinase inhibitor, AMP-activated protein kinases (AMPK), Amylin receptor agonist, Angiotensin II AT-1 receptor antagonist, Apoptosis Signaling Kinase 1 inhibitor, Autotaxin inhibitors, Bioactive lipid, Calcitonin agonist, Caspase inhibitor, Caspase-3 stimulator, Cathepsin inhibitor, Caveolin 1 inhibitor, CCR2 chemokine antagonist, CCR3 chemokine antagonist, CCR5 chemokine antagonist, Chloride channel stimulator, CNR1 inhibitor, Cyclin D1 inhibitor, Cytochrome P450 7A1 inhibitor, DGAT1/2 inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF 1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, Hedgehog (Hh) modulator, Hepatitis C virus NS3 protease inhibitor, Hepatocyte nuclear factor 4 alpha modulator (HNF4A), Hepatocyte growth factor modulator, HMG CoA reductase inhibitor, IL-10 agonist, IL-17 antagonist, Ileal sodium bile acid cotransporter inhibitor, Insulin sensitizer, integrin modulator, intereukin-1 receptor-associated kinase 4 (IRAK4) inhibitor, Jak2 tyrosine kinase inhibitor, ketohexokinase inhibitors, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Matrix metalloproteinases (MMPs) inhibitor, MEKK-5 protein kinase inhibitor, Membrane copper amine oxidase (VAP-1) inhibitor, Methionine aminopeptidase-2 inhibitor, Methyl CpG binding protein 2 modulator, MicroRNA-21 (miR-21) inhibitor, Mitochondrial uncoupler, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, PDE 3 inhibitor, PDE 4 inhibitor, PDE 5 inhibitor, PDGF receptor beta modulator, Phospholipase C inhibitor, PPAR alpha agonist, PPAR delta agonist, PPAR gamma agonist, PPAR gamma modulator, Protease-activated receptor-2 antagonist, Protein kinase modulator, Rho associated protein kinase inhibitor, Sodium glucose transporter-2 inhibitor, SREBP transcription factor inhibitor, STAT-1 inhibitor, Stearoyl CoA desaturase-1 inhibitor, Suppressor of cytokine signalling-1 stimulator, Suppressor of cytokine signalling-3 stimulator, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, and YAP/TAZ modulator. Examples of JAK inhibitors include, but are not limited to, filgotonib and tofacitinib. A non-limiting example of an apoptosis signal kinase inhibitor is selonsertib.

The compound of Formula 1, or the stereoisomer thereof, or the pharmaceutically acceptable salt thereof, and at least one additional active agent may be administered in any order or even simultaneously. The multiple active agents may be provided in a single, unified form, or in multiple forms (by way of example only, either as a single pill or as two separate pills). One of the active agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

The pharmaceutical composition of the present technology may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition of the present technology may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition.

Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The composition of the present technology can be administered orally or parenterally, including inhalation, intravenous, intraperitoneal, subcutaneous, rectal and topical routes of administration. Therefore, the composition of the present technology can be formulated into various forms such as tablets, capsules, aqueous solutions, suspensions, or the like. In the case of tablets for oral administration, carriers such as lactose, corn starch, and lubricating agents, e.g., magnesium stearate, can be conventionally added thereto. In the case of capsules for oral administration, lactose and/or dried corn starch can be used as a diluent. When an aqueous suspension is required for oral administration, the active ingredient can be combined with emulsifying and/or suspending agents. If desired, certain sweetening agents and/or flavoring agents can be added thereto. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present technology may be in the form of an aqueous solution containing pharmaceutically acceptable carriers, e.g., saline having a pH level of 7.4. The solutions may be introduced into a patient's intramuscular blood-stream by local bolus injection.

Said triazolopyridin-3-ones, i.e., the compound of Formula 1, or a stereoisomer thereof, or a pharmaceutically acceptable salt thereof, can be administered to a patient in an effective amount ranging from about 0.001 mg/kg to about 100 mg/kg per day. This includes 0.001, 0.0025, 0.005, 0.0075, 0.01, 0.025, 0.05, 0.075, 0.1, 0.25, 0.5, 0.75, 1, 2, 3, 4, 5, 6, 7, 8, 9, 10, 15, 20, 25, 30, 35, 40, 45, 50, 55, 60, 65, 70, 75, 80, 85, 90, 95, or 100 mg/kg.

Generally, a therapeutically effective amount of the compound of Formula 1, or a stereoisomer thereof, or a pharmaceutically acceptable salt thereof, will range from a total daily dosage of about 0.1 mg/day to 1000 mg/day, about 30-720 mg/day, about 60-600 mg/day, or about 100-480 mg/day, or more. In some embodiments, a therapeutically effective amount of the compound of Formula 1, or a stereoisomer thereof, or a pharmaceutically acceptable salt thereof, will range from about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, multiple dosages include two, three, or four doses per day.

In some embodiments, the therapeutically effective amount of the compound of Formula 1, or a stereoisomer thereof, or a pharmaceutically acceptable salt thereof, is at least 0.1 mg/day, at least 0.5 mg/day, at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, at least 725 mg/day, at least 750 mg/day, at least 775 mg/day, at least 800 mg/day, at least 825 mg/day, at least 850 mg/day, at least 875 mg/day, at least 900 mg/day, at least 925 mg/day, at least 950 mg/day, at least 975 mg/day, or at least 1000 mg/day.

Of course, the dosage may be changed according to the patient's age, weight, susceptibility, symptom, or the efficacy of the compound.

In one embodiment, the present technology provides a method of inhibiting vascular adhesion protein (VAP)-1 in a mammal, comprising administering to the mammal a therapeutically effective amount of the compound of Formula 1 or a stereoisomer thereof or a pharmaceutically acceptable salt thereof. In another embodiment, the present technology provides a method for treating nonalcoholic hepatosteatosis (NASH), comprising administering to a mammal a therapeutically effective amount of the compound of Formula 1 or a stereoisomer thereof or a pharmaceutically acceptable salt thereof. In some embodiments, provided herein is a method for treating NASH in a subject in need thereof, the method comprising, consisting essentially of, or consisting of administering to the subject a therapeutically effective amount of a compound of Formula 1, or a stereoisomer thereof, or a pharmaceutically acceptable salt thereof. Mammals include, but are not limited to, mice, rodents, rats, simians, humans, farm animals, dogs, cats, sport animals, and pets.

In some embodiments, the present technology provides a use of the compound of Formula 1 above or a stereoisomer thereof or a pharmaceutically acceptable salt thereof for use in the preparation of a medicament for inhibiting a vascular adhesion protein-1 (VAP-1) in mammals.

In one embodiment, the present technology provides a use of the compound of Formula 1 above or a stereoisomer thereof or a pharmaceutically acceptable salt thereof for use in the preparation of a medicament for treating or preventing nonalcoholic hepatosteatosis (NASH).

Hereinafter, the present technology is further elaborated through examples and experimental examples. However, the following examples and experimental examples are provided for illustration purposes only, and are not intended to limit the scope of the invention.

As will be apparent to those of skill in the art upon reading this disclosure, each of the individual embodiments described and illustrated herein has discrete components and features which may be readily separated from or combined with the features of any of the other several embodiments without departing from the scope or spirit of the present technology. Any recited method can be carried out in the order of events recited or in any other order which is logically possible.

EXAMPLES

The analyses of the compounds prepared in the following examples were carried out as follows: Nuclear magnetic resonance (NMR) spectrum analysis was carried out using Bruker 400 MHz spectrometer and Agilent 600 MHz spectrometer and chemical shifts thereof were analyzed in ppm. Further, the indicated molecular weights were measured by using liquid chromatography/mass selective detector (MSD) of Agilent 1260 Infinity series equipped with an electrostatic spray interface (by using Single Quadrupole, it indicates a value of m/z in ESI+ (ESI-MS (cation), which is represented by the [M+H]+peak). Column chromatography was carried out on silica gel (Merck, 70-230 mesh). (W. C. Still, *J. Org. Chem.*, 43, 2923, 1978). Further, the abbreviations used in the following examples are as follows: 'methyl' is abbreviated to 'Me'; 'ethyl' is abbreviated to 'Et'; 'phenyl' is abbreviated to 'Ph, tert-butyloxycarbonyl is abbreviated to 'Boc'; and tert-butyl dimethylsilyl is abbreviated to TBDMS. Further, the starting materials in each example are known compounds, which were synthesized according to literatures or obtained from Sigma-Aldrich.

Reference Example 1. tert-butyl (E)-(2-(chloromethyl)-3-fluoroallyl)carbamate 1.0 g of tert-butyl (E)-(3-fluoro-2-(hydroxymethyl)allyl) carbamate, 1.2 g of p-toluenesulfonyl chloride, and 0.88 mL of triethylamine were dissolved in 10.0 mL of dichloromethane and then the resulting solution was stirred at room temperature for 24 hours. To the resulting reaction mixture, dichloromethane was added. The reaction mixture was washed with distilled water, dried over anhydrous magnesium sulfate, and then concentrated under reduced pressure to give a yellow liquid residue. The residue was purified with silica gel column chromatography (developing solvent: n-hexane/ethyl acetate=2/1) to give 924 mg of the title compound as a white solid (yield: 84.8%). $^1$H-NMR (CDCl$_3$, 400 MHz) δ 7.61 (s, 1H), 7.51 (t, 1H), 7.16 (s, 1H), 4.69 (s, 2H), 4.65-4.60 (m, 1H), 3.90 (s, 3H), 3.61-3.48 (m, 2H), 3.41 (s, 3H), 1.31 (d, 3H)

Reference Example 2. tert-butyl N-[3,3-difluoro-2-(hydroxymethyl)allyl]carbamate Step 1: tert-butyl N-[2-[[tert-butyl(dimethyl)silyl] oxymethyl]-3,3-difluoro-allyl]carbamate Under nitrogen condition, 2.4 g of tert-butyl N-[3-[tert-butyl(dimethyl)silyl]oxy-2-oxo-propyl]carbamate and 1.0 g of 2-(difluoromethylsulfonyl)pyridine were dissolved in 34.5 mL of N,N-dimethylformamide and then cooled to −70° C. To the reaction mixture, 10.4 mL of a tetrahydrofuran solution of 1.0 M lithium bis(trimethylsilyl)amide was slowly added dropwise. The resulting solution was stirred at −70° C. for 30 minutes and then stirred again by slowly increasing the temperature to −10° C. 20 mL of an ammonium chloride solution was added to the reaction mixture, followed by the addition of 20 mL of a 3 N hydrogen chloride solution. The reaction mixture was extracted with ethyl acetate three times. The extracted organic layer was washed with brine, dried over anhydrous magnesium sulfate, and concentrated under reduced pressure to give a yellow liquid residue. The residue was purified with silica gel column chromatography (developing solvent: n-hexane/ ethyl acetate=20/1) to give 446 mg of the title compound as a yellow liquid (yield: 25.5%). $^1$H-NMR (CDCl$_3$, 400 MHz) δ 4.98 (s, 1H), 4.20 (s, 2H), 3.83 (s, 2H), 1.42 (s, 9H), 0.89 (s, 9H), 0.07 (s, 6H)

Step 2: tert-butyl N-[3,3-difluoro-2-(hydroxymethyl)allyl]carbamate 426 mg of tert-butyl N-[2-[[tert-butyl(dimethyl)silyl] oxymethyl]-3,3-difluoro-allyl]carbamate was dissolved in 2.0 mL of tetrahydrofuran, followed by the addition of 1.5 mL of a tetrahydrofuran solution of 1.0 M tetrabutylamonium fluoride (TBAF), and then the resulting solution was stirred at room temperature for 2 hours. The reaction mixture thus obtained was added with ethyl acetate and water to separate an organic layer. The aqueous layer of the reaction mixture was added with ethyl acetate to separate an organic layer again. The organic layers thus obtained were combined and washed with an ammonium chloride solution and brine, dried over anhydrous magnesium sulfate, and then concentrated under reduced pressure to give a yellow residue. The residue was purified with silica gel column chromatography (developing solvent: n-hexane/ethyl acetate=2/1) to give 285 mg of the title compound as a colorless liquid (yield: 100%). $^1$H-NMR (CDCl$_3$, 400 MHz) δ 4.91 (s, 1H), 4.14 (s, 2H), 3.86 (d, 2H), 3.72 (s, 1H), 1.45 (s, 9H)

Reference Example 3. 6-bromo-2H-[1,2,4]triazolo[4,3-a]pyridin-3-one

Step 1: 5-bromo-2-hydrazinylpyridine 5.0 g of 5-bromo-2-fluoropyridine was dissolved in 50.0 mL of tetrahydrofuran, and to the resulting solution, 5.0 mL of hydrazine hydrate was added dropwise. The reaction mixture was stirred at 70° C. for 2 hours. The reaction mixture was cooled to room temperature, followed by the addition of ethyl acetate, and then the reaction mixture was washed with distilled water. The organic layer thus obtained was dried over anhydrous magnesium sulfate and concentrated under reduced pressure to give 4.0 g of the title compound as a white solid (74.9%).

Step 2: 6-bromo-2H-[1,2,4]triazolo[4,3-a]pyridin-3-one 4.0 g of 5-bromo-2-hydrazinylpyridine prepared in Step 1 was dissolved in 50.0 mL of acetonitrile, followed by the addition of 4.1 g of carbonyldiimidazole. The resulting solution was stirred at 90° C. for 2 hours. The reaction mixture was cooled to room temperature. Additionally, the reaction mixture was further stirred at room temperature for 1 hour. The reaction mixture was added with 20.0 mL of water and then extracted with ethyl acetate. The organic layer thus obtained was washed with brine, dried over anhydrous magnesium sulfate, and concentrated under reduced pressure to give a solid residue. The solid residue was suspended in dichloromethane and then washed with hexane and filtered and dried to give 1.4 g of the title compound as a white solid (yield: 30.7%). MS (ESI) m/z=215.1 (M+H)+

Reference Example 4. 5-bromo-2H-[1,2,4]triazolo[4,3-a]pyridin-3-one 1.1 g of the title compound as a white solid (yield: 99.5%) was prepared in the same fashion as Steps 1 and 2 of Reference Example 3 except that 1.0 g of 2-bromo-6-fluoropyridine was used instead of 5-bromo-2-fluoropyridine. $^1$H-NMR (DMSO-d$_6$, 400 MHz) δ 12.57 (s, 1H), 7.13 (d, 1H), 6.92 (t, 1H), 6.71 (d, 1H)

Reference Example 5. 7-bromo-2H-[1,2,4]triazolo[4,3-a]pyridin-3-one 1.0 g of the title compound as a white solid (yield: 82.3%) was prepared in the same fashion as Steps 1 and 2 of Reference Example 3 except that 1.0 g of 4-bromo-2-fluoropyridine was used instead of 5-bromo-2-fluoropyridine. $^1$H-NMR (DMSO-d$_6$, 400 MHz) δ 12.55 (s, 1H), 7.76 (d, 1H), 7.62 (s, 1H), 6.65 (d, 1H)

Reference Example 6. tert-butyl N-[(E)-2-[(6-bromo-3-oxo-[1,2,4]triazolo[4,3-a]pyridin-2-yl)methyl]-3-fluoro-allyl]carbamate 150 mg of 6-bromo-2H-[1,2,4]triazolo[4,3-a]pyridin-3-one prepared in Reference Example 3 and 291 mg of potassium carbonate were dissolved in 2.0 mL of N,N-dimethylformamide, followed by the addition of 236 mg of tert-butyl (E)-(2-(chloromethyl)-3-fluoroallyl)carbamate prepared in Reference Example 1. The resulting solution thus obtained was stirred at 90° C. for 3 hours. The resulting reaction mixture was concentrated, followed by the addition of dichloromethane. The concentrated reaction mixture was washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 151 mg of the title compound as a white solid (yield: 53.8%). $^1$H-NMR (CDCl$_3$, 400 MHz) δ 7.92 (s, 1H), 7.13 (d, 1H), 7.01 (d, 1H), 6.76 (d, 1H), 5.20 (bs, 1H), 4.52 (s, 2H), 3.86 (s, 2H), 1.41 (s, 9H)

Reference Example 7. tert-butyl N-[(E)-2-[(5-bromo-3-oxo-[1,2,4]triazolo[4,3-a]pyridin-2-yl)methyl]-3-fluoro-allyl]carbamate 212 mg of the title compound as a white solid (yield: 86.9%) was prepared in the same fashion as Reference Example 6 except that 131 mg of 5-bromo-2H-[1,2,4]triazolo[4,3-a]pyridin-3-one prepared in Reference Example 4 was used instead of 6-bromo-2H-[1,2,4]triazolo[4,3-a]pyridin-3-one prepared in Reference Example 3. MS (ESI) m/z=302.2 (M+H)+

Reference Example 8. tert-butyl N-[(E)-2-[(7-bromo-3-oxo-[1,2,4]triazolo[4,3-a]pyridin-2-yl)methyl]-3-fluoro-allyl]carbamate 305 mg of the title compound as a white solid (yield: 81.7%) was prepared in the same fashion as Reference Example 6 except that 200 mg of 7-bromo-2H-[1,2,4]triazolo[4,3-a]pyridin-3-one prepared in Reference Example 5 was used instead of 6-bromo-2H-[1,2,4]triazolo[4,3-a]pyridin-3-one prepared in Reference Example 3. $^1$H-NMR (CDCl$_3$, 400 MHz) δ 7.63 (d, 1H), 7.31 (s, 1H), 6.76 (d, 1H), 6.59 (d, 1H), 5.19 (bs, 1H), 4.49 (s, 2H), 3.86 (s, 2H), 1.41 (s, 9H)

Reference Example 9. tert-butyl N-[2-[(5-bromo-3-oxo-[1,2,4]triazolo[4,3-a]pyridin-2-yl)methyl]-3,3-difluoro-allyl]carbamate 96 mg of 5-bromo-2H-[1,2,4]triazolo[4,3-a]pyridin-3-one prepared in Reference Example 4, 100 mg of tert-butyl N-[3,3-difluoro-2-(hydroxymethyl)allyl]carbamate prepared in Step 2 of Reference Example 2, and 235 mg of triphenylphosphine were dissolved in 2.0 mL of tetrahydrofuran and the resulting solution was stirred and cooled to 0° C. To the reaction mixture, 176 uL of diisopropyl azodicarboxylate (DIAD) was slowly added dropwise and stirred at room temperature for 6 hours. The reaction mixture was concentrated under reduced pressure to give a yellow liquid residue. The residue was purified with silica gel column chromatography (developing solvent: n-hexane/ethyl acetate=2/1) to give 206 mg of the title compound as a yellow liquid (yield: 87.1%). MS (ESI) m/z=320.0 (M+H)+

Reference Example 10. tert-butyl N-[2-[(6-bromo-3-oxo-[1,2,4]triazolo[4,3-a]pyridin-2-yl)methyl]-3,3-difluoro-allyl]carbamate 212 mg of the title compound as a white solid (yield: 100%) was prepared in the same fashion as Reference Example 6 except that 96 mg of 6-bromo-2H-[1,2,4]triazolo[4,3-a]pyridin-3-one prepared in Reference Example 3 was used instead of 5-bromo-2H-[1,2,4]triazolo[4,3-a]pyridin-3-one prepared in Reference Example 4. MS (ESI) m/z=320.0 (M+H)+

Reference Example 11. tert-butyl N-[2-[(7-bromo-3-oxo-[1,2,4]triazolo[4,3-a]pyridin-2-yl)methyl]-3,3-difluoro-allyl]carbamate 196 mg of the title compound as a white solid (yield: 93.0%) was prepared in the same fashion as Reference Example 6 except that 96 mg of 7-bromo-2H-[1,2,4]triazolo[4,3-a]pyridin-3-one prepared in Reference Example 5 was used instead of 5-bromo-2H-[1,2,4]triazolo[4,3-a]pyridin-3-one prepared in Reference Example 4. MS (ESI) m/z=320.0 (M+H)+

Example 1. 2-[(2E)-2-(aminomethyl)-3-fluoroprop-2-en-1-yl]-6-bromo[1,2,4]triazolo[4,3-a]pyridin-3(2H)-one hydrochloride 20 mg of tert-butyl N-[(E)-2-[(6-bromo-3-oxo-[1,2,4]triazolo[4,3-a]pyridin-2-yl)methyl]-3-fluoro-allyl]carbamate prepared in Reference Example 6 was dissolved in 1.0 mL of dichloromethane, followed by the addition of 2.0 mL of 4M HCl in dioxane solution. The resulting solution was stirred overnight at room temperature. The reaction mixture was filtered and dried to give 17 mg of the title compound as a white solid (yield: 100%). $^1$H-NMR (MeOD, 400 MHz) δ 8.01 (s, 1H), 7.29-7.15 (m, 2H), 7.12-7.05 (m, 1H), 4.63 (m, 2H), 3.68 (m, 2H)

Example 2. N-[4-[2-[(2E)-2-(aminomethyl)-3-fluoroprop-2-en-1-yl]-3-oxo-2,3-dihydro[1,2,4]triazolo[4,3-a]pyridin-6-yl]phenyl]acetamide trifluoroacetate Step 1: tert-butyl (E)-(2-((6-(4-acetamidophenyl)-3-oxo-[1,2,4]triazolo[4,3-a]pyridine-2(3H)-yl)methyl)-3-fluoroallyl)carbamate 30 mg of tert-butyl N-[(E)-2-[(6-bromo-3-oxo-[1,2,4]triazolo[4,3-a]pyridin-2-yl)methyl]-3-fluoro-allyl]carbamate prepared in Reference Example 6 and 34 mg of 4-acetamidobenzeneboronicacid were dissolved in 1.0 mL of 1,4-dioxane 1.0 mL, followed by the addition of 0.4 mL of 2 M sodium carbonate and 3 mg of palladiumdi[1,1'-bis(diphenylphospino)ferrocene]dichloride (PdCl$_2$(dppf)). The resulting solution was stirred overnight at 90° C. The resulting reaction mixture was filtered through a celite pad and concentrated under reduced pressure to give a residue. The residue thus obtained was dissolved in ethylacetate, washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 29 mg of the title compound (yield: 84.9%). MS (ESI) m/z=356.0 (M+H)+

Step 2: N-[4-[2-[(2E)-2-(aminomethyl)-3-fluoroprop-2-en-1-yl]-3-oxo-2,3-dihydro[1,2,4]triazolo[4,3-a]pyridin-6-yl]phenyl]acetamide trifluoroacetate 29 mg of tert-butyl (E)-(2-((6-(4-acetamidophenyl)-3-oxo-[1,2,4]triazolo[4,3-a]pyridine-2(3H)-yl)methyl)-3-fluoroallyl)carbamate prepared in Step 1 was dissolved in 1.0 mL of dichloromethane, followed by the addition of 0.5 mL of trifluoroacetic acid. The resulting solution was stirred overnight at room temperature. The reaction mixture thus obtained was concentrated, followed by the addition of dichloromethane. The solution was concentrated under reduced pressure and then dried in vacuo to obtain a yellow liquid residue. The residue was purified with silica gel column chromatography (developing solvent: dichloromethane/methanol=10/1) to give 11 mg of the title compound as a white solid (yield: 48.4%). $^1$H-NMR (MeOD, 400 MHz) δ 7.98 (s, 1H), 7.66 (m, 2H), 7.60 (m, 1H), 7.55 (m, 2H), 7.28 (m 1H), 7.26-7.09 (m, 1H), 4.67 (m, 2H), 3.72 (m, 2H), 2.12 (s, 3H)

Example 3. 2-[(2E)-2-(aminomethyl)-3-fluoroprop-2-en-1-yl]-6-[4-(methyl sulfonyl)phenyl][1,2,4]triazolo[4,3-a]pyridin-3(2H)-one trifluoroacetate 20 mg of the title compound (yield: 70.8%) was prepared in the same fashion as Example 2 except that, in Step 1, 38 mg of 4-(methanesulfonyl)phenylboronic acid was used instead of 4-acetamidobenzeneboronicacid. $^1$H-NMR (MeOD, 400 MHz) δ 8.19 (s, 1H), 8.04 (m, 2H), 7.89 (m, 2H), 7.67 (d, 1H), 7.34 (m, 1H), 7.31-7.11 (d, 1H), 4.70 (m, 2H), 3.74 (m, 2H), 3.39 (s, 3H)

Example 4. 2-[(2E)-2-(aminomethyl)-3-fluoroprop-2-en-1-yl]-6-[4-(morpholin-4-ylsulfonyl)phenyl][1,2,4]triazolo[4,3-a]pyridin-3(2H)-one trifluoroacetate 9 mg of the title compound (yield: 26.8%) was prepared in the same fashion as Example 2 except that in Step 1, 66 mg of 4-((4-(4,4,5,5-tetramethyl-1,3,2-dioxaborolan-2-yl)phenyl)sulfonyl)morpholine was used instead of 4-acetamidobenzeneboronicacid. $^1$H-NMR (MeOD, 400 MHz) δ 8.21 (s, 1H), 7.89 (m, 4H), 7.70 (m, 1H), 7.36 (m, 1H), 7.32-7.11 (m, 1H), 4.70 (m, 2H), 3.75 (m, 2H), 3.71 (m, 4H), 2.99 (m, 4H)

Example 5. 2-[(2E)-2-(aminomethyl)-3-fluoroprop-2-en-1-yl]-6-[4-(1H-1,2,4-triazol-3-yl)phenyl][1,2,4]triazolo[4,3-a]pyridin-3(2H)-one trifluoroacetate 13 mg of the title compound (yield: 48.5%) was prepared in the same fashion as Example 2 except that in Step 1, 76 mg of 3-(4-(4,4,5,5-tetramethyl-1,3,2-dioxaborolan-2-yl)phenyl)-1-((2-(trimethylsilyl)ethoxy)methyl)-1H-1,2,4-triazol was used instead of 4-acetamidobenzeneboronicacid. $^1$H-NMR (MeOD, 400 MHz) δ 8.43 (brs, 1H), 8.18 (s, 1H), 8.14 (m, 2H), 7.78 (d, 2H), 7.72 (d, 1H), 7.34 (s, 1H), 7.32-7.13 (m, 1H), 4.71 (m, 2H), 3.76 (m, 2H)

Example 6. 2-[(2E)-2-(aminomethyl)-3-fluoroprop-2-en-1-yl]-6-[3-(1H-1,2,4-triazol-3-yl)phenyl][1,2,4]triazolo[4,3-a]pyridin-3(2H)-one 14 mg of the title compound (yield: 51.8%) was prepared in the same fashion as Example 2 except that in Step 1, 76 mg of 3-(3-(4,4,5,5-tetramethyl-1,3,2-dioxaborolan-2-yl)phenyl)-1-((2-(trimethylsilyl)ethoxy)methyl)-1H-1,2,4-triazol was used instead of 4-acetamidobenzeneboronicacid. $^1$H-NMR (MeOD, 400 MHz) δ 8.45 (brs, 1H), 8.31 (m, 1H), 8.15 (m, 1H), 8.05 (m, 1H), 7.70 (m, 2H), 7.61 (m, 1H), 7.35-7.13 (m, 2H), 4.71 (m, 2H), 3.76 (m, 2H)

Example 7. 2-[(2E)-2-(aminomethyl)-3-fluoroprop-2-en-1-yl]-6-[4-(1,2-oxazol-3-yl)phenyl][1,2,4]triazolo[4,3-a]pyridin-3(2H)-one hydrochloride Step 1: tert-butyl N-[(E)-3-fluoro-2-[[6-(4-isoxazol-3-yl)phenyl)-3-oxo-[1,2,4]triazolo[4,3-a]pyridin-2-yl]methyl]allyl]carbamate 30 mg of tert-butyl N-[(E)-2-[(6-bromo-3-oxo-[1,2,4]triazolo[4,3-a]pyridin-2-yl)methyl]-3-fluoro-allyl]carbamate prepared in Reference Example 6 and 30 mg of 3-[4-(4,4,5,5-tetramethyl-1,3,2-dioxaborolan-2-yl)phenyl]isoxazol were dissolved in 1.0 mL of 1,4-dioxane, followed by the addition of 0.4 mL of 1 M Calcium carbonate and 2 mg of palladiumdi[1,1'-bis(diphenylphospino)ferrocene]dichloride (PdCl$_2$(dppf)). The resulting solution was stirred overnight at 90° C. The resulting reaction mixture was filtered through a celite pad and concentrated under reduced pressure to give a residue. The residue thus obtained was dissolved in ethylacetate, washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 28 mg of the title compound (yield: 78.8%). MS (ESI) m/z=366.1 (M+H)+

Step 2: 2-[(2E)-2-(aminomethyl)-3-fluoroprop-2-en-1-yl]-6-[4-(1,2-oxazol-3-yl)phenyl][1,2,4]triazolo[4,3-a]pyridin-3(2H)-one hydrochloride 28 mg of tert-butyl N-[(E)-3-fluoro-2-[[6-(4-isoxazol-3-ylphenyl)-3-oxo-[1,2,4]triazolo[4,3-a]pyridin-2-yl]methyl]allyl]carbamate prepared in Step 1 was dissolved in 0.5 mL of ethyl acetate, followed by the addition of 0.3 mL of 4M HCl in dioxane solution. The resulting solution was stirred overnight at room temperature. The reaction mixture was filtered and dried to give 25 mg of the title compound as a colorless solid (yield: 100%). $^1$H-NMR (DMSO-d$_6$, 400 MHz) δ 9.04 (s, 1H), 8.22 (s, 1H), 7.99 (d, 2H), 7.89 (d, 2H), 7.73 (d, 1H), 7.40 (d, 1H), 7.24 (s, 1H), 7.23 (d, 1H), 4.68 (s, 2H), 3.53 (s, 2H)

Example 8. N-[4-[2-[(2E)-2-(aminomethyl)-3-fluoroprop-2-en-1-yl]-3-oxo-2,3-dihydro[1,2,4]triazolo[4,3-a]pyridin-6-yl]pyridin-2-yl]acetamide trifluoroacetate 8 mg of the title compound (yield: 29.9%) was prepared in the same fashion as Example 2 except that in Step 1, 50 mg of N-(4-(4,4,5,5-tetramethyl-1,3,2-dioxaborolan-2-yl)pyridin-2-yl)acetamide was used instead of 4-acetamidobenzeneboronicacid. $^1$H-NMR (MeOD, 400 MHz) δ 8.37 (s, 1H), 8.36 (m, 1H), 7.66 (m, 1H), 7.38 (m, 1H), 7.36-7.12 (m, 1H), 7.33 (m, 1H), 4.70 (m, 2H), 3.75 (m, 2H), 2.21 (s, 3H)

Example 9. 2-[(2E)-2-(aminomethyl)-3-fluoroprop-2-en-1-yl]-6-[6-(trifluoromethyl)pyridin-3-yl][1,2,4]triazolo[4,3-a]pyridin-3(2H)-one hydrochloride 10 mg of the title compound as a colorless solid (yield: 33.0%) was prepared in the same fashion as Example 7 except that in Step 1, 21 mg of 2-(trifluoromethyl)pyridine-5-boronic acid was used instead of 3-[4-(4,4,5,5-tetramethyl-1,3,2-dioxaborolan-2-yl)phenyl]isoxazol. $^1$H-NMR (DMSO-d$_6$, 400 MHz) δ 9.15 (s, 1H), 8.46 (s, 2H), 7.99 (d, 1H), 7.75 (d, 1H), 7.44 (d, 1H), 7.24 (d, 1H), 4.68 (s, 2H), 3.56 (s, 2H)

Example 10. 2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one trifluoroacetate 11 mg of the title compound as a white solid (yield: 37.8%) was prepared in the same fashion as Example 2 except that in Step 1, 55 mg of 6-(morpholin-4-yl)pyridine-3-boronic acid pinacol ester was used instead of 4-acetamidobenzeneboronicacid. $^1$H-NMR (MeOD, 400 MHz) δ 8.33 (m, 1H), 7.96 (s, 1H), 7.84 (m, 1H), 7.56 (m, 1H), 7.27 (s, 1H), 7.24-7.07 (m, 1H), 6.92 (d, 1H), 4.64 (m, 1H), 3.77 (m, 4H), 3.70 (m, 2H), 3.25 (m, 4H)

Example 11. 2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one hydrochloride 12 mg of the title compound as a colorless solid (yield: 38.0%) was prepared in the same fashion as Example 7 except that in Step 1, 33 mg of 6-(morpholin-4-yl)pyridine-3-boronic acid pinacol ester was used instead of 3-[4-(4,4,5,5-tetramethyl-1,3,2-dioxaborolan-2-yl)phenyl]isoxazol. $^1$H-NMR (DMSO-d$_6$, 400 MHz) δ 8.44 (s, 1H), 8.12 (s, 1H), 8.06 (d, 1H), 7.64 (d, 1H), 7.35 (d, 1H), 7.23 (d, 1H), 7.06 (d, 1H), 4.66 (s, 2H), 3.72 (s, 4H), 3.56-3.55 (m, 6H)

Example 12. 2-[(2E)-2-(aminomethyl)-3-fluoroprop-2-en-1-yl]-6-(1,3-benzodioxol-5-yl)[1,2,4]triazolo[4,3-a]pyridin-3(2H)-one hydrochloride 15 mg of the title compound as a grey solid (yield: 52.8%) was prepared in the same fashion as Example 7 except that in Step 1, 19 mg of 3,4-(methylenedioxy)phenyl boronic acid was used instead of 3-[4-(4,4,5,5-tetramethyl-1,3,2-dioxaborolan-2-yl)phenyl]isoxazol. $^1$H-NMR (DMSO-d$_6$, 400 MHz) δ 8.01 (s, 1H), 7.61 (d, 1H), 7.36 (d, 1H), 7.34 (s, 2H), 7.18 (d, 1H), 7.00 (d, 1H), 6.07 (s, 2H), 4.65 (s, 2H), 3.51 (s, 2H)

Example 13. 2-[(2E)-2-(aminomethyl)-3-fluoroprop-2-en-1-yl]-6-(2,3-dihydro-1,4-benzodioxin-6-yl)[1,2,4]triazolo[4,3-a]pyridin-3(2H)-one trifluoroacetate 9 mg of the title compound as a white solid (yield: 33.3%) was prepared in the same fashion as Example 2 except that in Step 1, 34 mg of (2,3-dihydrobenzo[b][1,4]dioxin-6-yl)boronic acid was used instead of 4-acetamidobenzeneboronicacid $^1$H-NMR (MeOD, 400 MHz) δ 7.96 (s, 1H), 7.62 (m, 1H), 7.34 (m, 1H), 7.28-7.09 (m, 3H), 6.95 (m, 1H), 4.71 (m, 2H), 4.30 (s, 4H), 3.71 (m, 2H)

Example 14. 6-(2-amino-1,3-benzothiazol-5-yl)-2-[(2E)-2-(aminomethyl)-3-fluoroprop-2-en-1-yl][1,2,4]triazolo[4,3-a]pyridin-3(2H)-one trifluoroacetate 10 mg of the title compound as a white solid (yield: 36.0%) was prepared in the same fashion as Example 2 except that in Step 1, 52 mg of 5-(4,4,5,5-tetramethyl-1,3,2-dioxaborolan-2-yl)benzo[d]thiazol-2-amine was used instead of 4-acetamidobenzeneboronicacid. $^1$H-NMR (MeOD, 400 MHz) δ 8.07 (s, 1H), 7.73 (d, 1H), 7.68 (d, 1H), 7.62 (m, 1H), 7.38 (d, 1H), 7.33 (s, 1H), 7.31-7.13 (m, 1H), 4.71 (m, 2H), 3.75 (m, 2H)

Example 15. N-[5-[2-[(2E)-2-(aminomethyl)-3-fluoroprop-2-en-1-yl]-3-oxo-2,3-dihydro[1,2,4]triazolo[4,3-a]pyridin-6-yl]-1,3-benzothiazol-2-yl]acetamide trifluoroacetate 9 mg of the title compound as a white solid (yield: 29.1%) was prepared in the same fashion as Example 2 except that in Step 1, 60 mg of N-5-(4,4,5,5-tetramethyl-1,3,2-dioxaborolan-2-yl)benzo[d]thiazol-2-yl)acetamide was used instead of 4-acetamidobenzeneboronicacid. $^1$H-NMR (MeOD, 400 MHz) δ 8.06 (s, 1H), 7.95-7.70 (m, 2H), 7.67 (d, 1H), 7.54 (d, 1H), 7.33 (s, 1H), 7.31-7.13 (m, 1H), 4.71 (m, 2H), 3.77 (m, 2H), 2.28 (s, 3H)

Example 16. 2-[(2E)-2-(aminomethyl)-3-fluoroprop-2-en-1-yl]-6-(2,1,3-benzoxadiazol-5-yl)[1,2,4]triazolo[4,3-a]pyridin-3(2H)-one trifluoroacetate 13 mg of the title compound as a white solid (yield: 52.5%) was prepared in the same fashion as Example 2 except that in Step 1, 47 mg of benzo[c][1,2,5]oxadiazole-5-boronic acid pinacol ester was used instead of 4-acetamidobenzeneboronicacid. $^1$H-NMR (MeOD, 400 MHz) δ 8.30 (s, 1H), 8.18 (s, 1H), 8.02 (m, 1H), 7.86 (m, 1H), 7.76 (m, 1H), 7.36 (m, 1H), 7.32-7.11 (m, 1H), 4.70 (m, 2H), 3.74 (m, 2H)

Example 17. 6-[2-[(2E)-2-(aminomethyl)-3-fluoroprop-2-en-1-yl]-3-oxo-2,3-dihydro[1,2,4]triazolo[4,3-a]pyridin-6-yl]-8-methyl-3,4-dihydroquinolin-2(1H)-one hydrochloride 11 mg of the title compound as a grey solid (yield: 35.1%) was prepared in the same fashion as Example 7 except that in Step 1, 32 mg of 8-methyl-2-oxo-1,2,3,4-tetrahydroquinoline-6-boronic acid pinacol ester was used instead of 3-[4-(4,4,5,5-tetramethyl-1,3,2-dioxaborolan-2-yl)phenyl]isoxazol. $^1$H-NMR (DMSO-d$_6$, 400 MHz) δ 9.55 (s, 1H), 7.97 (s, 1H), 7.61 (d, 1H), 7.40 (d, 2H), 7.31 (d, 1H), 7.18 (d, 1H), 6.84 (s, 1H), 4.45 (s, 2H), 3.64 (s, 2H), 2.92 (t, 2H), 2.48 (t, 2H), 2.27 (s, 3H)

Example 18. N-[4-[2-[(2E)-2-(aminomethyl)-3-fluoroprop-2-en-1-yl]-3-oxo-2,3-dihydro[1,2,4]triazolo[4,3-a]pyridin-5-yl]phenyl]acetamide trifluoroacetate 8 mg of the title compound as a white solid (yield: 31.1%) was prepared in the same fashion as Example 2 except that in Step 1, 30 mg of tert-butyl N-[(E)-2-[(5-bromo-3-oxo-[1,2,4]triazolo[4,3-a]pyridin-2-yl)methyl]-3-fluoro-allyl]carbamate prepared in Reference Example 7 was used instead of tert-butyl N-[(E)-2-[(6-bromo-3-oxo-[1,2,4]triazolo[4,3-a]pyridin-2-yl)methyl]-3-fluoro-allyl]carbamate. $^1$H-NMR (MeOD, 400 MHz) δ 7.63 (m, 2H), 7.44 (m, 2H), 7.26 (m, 1H), 7.16 (m, 1H), 7.13-7.05 (m, 1H), 6.47 (d, 1H), 4.59 (m, 2H), 3.69 (m, 2H), 2.14 (s, 3H)

Example 19. 2-[(2E)-2-(aminomethyl)-3-fluoroprop-2-en-1-yl]-5-[4-(1,2-oxazol-3-yl)phenyl][1,2,4]triazolo[4,3-a]pyridin-3(2H)-one trifluoroacetate 13 mg of the title compound as a white solid (yield: 47.4%) was prepared in the same fashion as Example 2 except that in Step 1, 30 mg of tert-butyl N-[(E)-2-[(5-bromo-3-oxo-[1,2,4]triazolo[4,3-a]pyridin-2-yl)methyl]-3-fluoro-allyl]carbamate prepared in Reference Example 7 was used instead of tert-butyl N-[(E)-2-[(6-bromo-3-oxo-[1,2,4]triazolo[4,3-a]pyridin-2-yl)methyl]-3-fluoro-allyl]carbamate and 52 mg of 3-[4-(4,4,5,5-tetramethyl-1,3,2-dioxaborolan-2-yl)phenyl]isoxazol was used instead of 4-acetamidobenzeneboronicacid. $^1$H-NMR (MeOD, 400 MHz) δ 8.76 (s, 1H), 8.05 (m, 1H), 7.94 (d, 2H), 7.65 (m, 2H), 7.31-7.18 (m, 3H), 6.99 (s, 1H), 6.58 (m, 1H), 4.60 (m, 2H), 3.59 (m, 2H)

Example 20. 2-[(2E)-2-(aminomethyl)-3-fluoroprop-2-en-1-yl]-5-(1,3-benzodioxol-5-yl)[1,2,4]triazolo[4,3-a]pyridin-3(2H)-one trifluoroacetate 17 mg of the title compound as a white solid (yield: 66.2%) was prepared in the same fashion as Example 2 except that in Step 1, 30 mg of tert-butyl N-[(E)-2-[(5-bromo-3-oxo-[1,2,4]triazolo[4,3-a]pyridin-2-yl)methyl]-3-fluoro-allyl]carbamate prepared in Reference Example 7 was used instead of tert-butyl N-[(E)-2-[(6-bromo-3-oxo-[1,2,4]triazolo[4,3-a]pyridin-2-yl)methyl]-3-fluoro-allyl]carbamate and 32 mg of 3,4-(methylenedioxy)phenylboronic acid was used instead of 4-acetamidobenzeneboronicacid. $^1$H-NMR (MeOD, 400 MHz) δ 7.26 (s, 1H), 7.23-7.06 (m, 2H), 6.99 (s, 1H), 6.97 (m, 1H), 6.87 (m, 1H), 6.46 (d, 1H), 6.02 (s, 2H), 4.61 (m, 2H), 3.70 (m, 2H)

Example 21. 2-[(2E)-2-(aminomethyl)-3-fluoroprop-2-en-1-yl]-5-(2,1,3-benzoxadiazol-5-yl)[1,2,4]triazolo[4,3-a]pyridin-3(2H)-one trifluoroacetate 15 mg of the title compound as a white solid (yield: 58.8%) was prepared in the same fashion as Example 2 except that in Step 1, 30 mg of tert-butyl N-[(E)-2-[(5-bromo-3-oxo-[1,2,4]triazolo[4,3-a]pyridin-2-yl)methyl]-3-fluoro-allyl]carbamate prepared in Reference Example 7 was used instead of tert-butyl N-[(E)-2-[(6-bromo-3-oxo-[1,2,4]triazolo[4,3-a]pyridin-2-yl)methyl]-3-fluoro-allyl]carbamate and 47 mg of benzo[c][1,2,5]oxadiazole-5-boronic acid pinacol ester was used instead of 4-acetamidobenzeneboronicacid. $^1$H-NMR (MeOD, 400 MHz) δ 8.07 (s, 1H), 7.88-7.67 (m, 1H), 7.29 (s, 1H), 7.23-7.03 (m, 2H), 6.71 (m, 1H), 4.61 (m, 2H), 3.66 (m, 2H)

Example 22. 2-[(2E)-2-(aminomethyl)-3-fluoroprop-2-en-1-yl]-7-[3-(methyl sulfonyl)phenyl][1,2,4]triazolo[4,3-a]pyridin-3(2H)-one hydrochloride 9 mg of the title compound as a brown solid (yield: 35.2%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 19 mg of 3-(methanesulfonyl)phenylboronic acid was used instead of 3-[4-(4,4,5,5-tetramethyl-1,3,2-dioxaborolan-2-yl)phenyl]isoxazol. $^1$H-NMR (DMSO-d$_6$, 400 MHz) δ 8.32 (s, 1H), 8.15 (d, 1H), 8.03 (d, 1H), 8.00 (d, 1H), 7.79 (t, 1H), 7.74 (s, 1H), 7.25 (d, 1H), 7.12 (dd, 1H), 4.68 (s, 2H), 3.53 (s, 2H), 3.32 (s, 3H)

Example 23. 2-[(2E)-2-(aminomethyl)-3-fluoroprop-2-en-1-yl]-7-2-[(dimethylamino)methyl]phenyl[1,2,4]triazolo[4,3-a]pyridin-3(2H)-one hydrochloride 10 mg of the title compound as a yellow solid (yield: 41.2%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 17 mg of 2-(N,N-dimethylaminomethyl)phenylboronic acid was used instead of 3-[4-(4,4,5,5-tetramethyl-1,3,2-dioxaborolan-2-yl)phenyl]isoxazol. $^1$H-NMR (DMSO-d$_6$, 400 MHz) δ 7.97 (d, 2H), 7.56 (p, 2H), 7.37 (dd, 2H), 7.25 (s, 1H), 7.20 (d, 1H), 6.61 (d, 1H), 4.68 (s, 2H), 4.28 (s, 2H), 3.52 (s, 2H), 2.55 (s, 6H)

Example 24. 2-[(2E)-2-(aminomethyl)-3-fluoroprop-2-en-1-yl]-7-[4-(morpholin-4-ylcarbonyl)phenyl][1,2,4]triazolo[4,3-a]pyridin-3(2H)-one hydrochloride 8 mg of the title compound as a colorless solid (yield: 28.8%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 29 mg of 4-(morpholine-4-carbonyl)phenylboronic acid pinacol ester was used instead of 3-[4-(4,4,5,5-tetramethyl-1,3,2-dioxaborolan-2-yl)phenyl]isoxazol. $^1$H-NMR (DMSO-d$_6$, 400 MHz) δ 7.98 (d, 1H), 7.86 (d, 2H), 7.61 (s, 1H), 7.54 (d, 2H), 7.24 (d, 1H), 7.05 (d, 1H), 4.66 (s, 2H), 3.62-3.56 (m, 8H), 3.52 (s, 2H)

Example 25. 2-[(2E)-2-(aminomethyl)-3-fluoroprop-2-en-1-yl]-7-[4-(1,2-oxazol-3-yl)phenyl][1,2,4]triazolo[4,3-a]pyridin-3(2H)-one hydrochloride 13 mg of the title compound as a colorless solid (yield: 43.1%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate. $^1$H-NMR (DMSO-d$_6$, 400 MHz) δ 9.05 (s, 1H), 8.03 (d, 2H), 7.97 (t, 3H), 7.67 (s, 1H), 7.26 (s, 1H), 7.25 (d, 1H), 7.09 (d, 1H), 4.67 (s, 2H), 3.53 (s, 2H)

Example 26. 2-[(2E)-2-(aminomethyl)-3-fluoroprop-2-en-1-yl]-7-[3-(1H-pyrazol-3-yl)phenyl][1,2,4]triazolo[4,3-a]pyridin-3(2H)-one hydrochloride 8 mg of the title compound as a colorless solid (yield: 32.2%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 17 mg of (3-(1H-pyrazol-3-yl)phenyl)boronic acid was used instead of 3-[4-(4,4,5,5-tetramethyl-1,3,2-dioxaborolan-2-yl)phenyl]isoxazol. $^1$H-NMR (DMSO-d$_6$, 400 MHz) δ 8.19 (s, 1H), 7.98 (d, 1H), 7.90 (d, 1H), 7.76 (d, 1H), 7.72 (d, 1H), 7.64 (s, 1H), 7.55 (t, 1H), 7.26 (d, 1H), 7.11 (d, 1H), 6.89 (s, 1H), 4.68 (s, 2H), 3.55 (t, 2H)

Example 27. 2-[(2E)-2-(aminomethyl)-3-fluoroprop-2-en-1-yl]-7-[4-(1,2,5-oxadiazol-3-yl)phenyl][1,2,4]triazolo[4,3-a]pyridin-3(2H)-one hydrochloride 14 mg of the title compound as a colorless solid (yield: 46.3%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 31 mg of 3-[4-(4,4,5,5-tetramethyl-1,3,2-dioxaborolan-2-yl)phenyl]-1,2,5-oxadiazole was used instead of 3-[4-(4,4,5,5-tetramethyl-1,3,2-dioxaborolan-2-yl)phenyl]isoxazol. MS (ESI) m/z=367.2 (M+H)+

Example 28. 2-[(2E)-2-(aminomethyl)-3-fluoroprop-2-en-1-yl]-7-[3-(5-cyclopropyl-1,2,4-oxadiazol-3-yl)phenyl][1,2,4]triazolo[4,3-a]pyridin-3(2H)-one hydrochloride 13 mg of the title compound as a brown solid (yield: 47.3%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 29 mg of 5-cyclopropyl-3-[3-(4,4,5,5-tetramethyl-1,3,2-dioxaborolan-2-yl)phenyl]-1,2,4-oxadiazole was used instead of 3-[4-(4,4,5,5-tetramethyl-1,3,2-dioxaborolan-2-yl)phenyl]isoxazol. $^1$H-NMR (DMSO-d$_6$, 400 MHz) δ 8.24 (s, 1H), 8.04 (d, 1H), 7.99 (d, 2H), 7.70 (t, 1H), 7.63 (s, 1H), 7.25 (d, 1H), 7.05 (dd, 1H), 4.67 (s, 2H), 3.53 (s, 2H), 2.46-2.42 (m, 1H), 1.32-1.29 (m, 2H), 1.23-1.21 (m, 2H)

Example 29. 2-[(2E)-2-(aminomethyl)-3-fluoroprop-2-en-1-yl]-7-[4-(5-cyclopropyl-1,2,4-oxadiazol-3-yl)phenyl][1,2,4]triazolo[4,3-a]pyridin-3(2H)-one hydrochloride 14 mg of the title compound as a brown solid (yield: 51.0%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 29 mg of 5-cyclopropyl-3-[4-(4,4,5,5-tetramethyl-1,3,2-dioxaborolan-2-yl)phenyl]-1,2,4-oxadiazole was used instead of 3-[4-(4,4,5,5-tetramethyl-1,3,2-dioxaborolan-2-yl)phenyl]isoxazol. $^1$H-NMR (DMSO-d$_6$, 400 MHz) δ 8.08 (d, 2H), 7.99 (t, 3H), 7.67 (s, 1H), 7.25 (d, 1H), 7.07 (d, 1H), 4.68 (s, 2H), 3.54 (s, 2H), 2.43 (p, 1H), 1.31 (q, 2H), 1.22 (q, 2H)

Example 30. 2-[(2E)-2-(aminomethyl)-3-fluoroprop-2-en-1-yl]-7-[6-(trifluoromethyl)pyridin-3-yl][1,2,4]triazolo[4,3-a]pyridin-3(2H)-one hydrochloride 15 mg of the title compound as a colorless solid (yield: 49.5%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 21 mg of 2-(trifluoromethyl)pyridine-5-boronic acid was used instead of 3-[4-(4,4,5,5-tetramethyl-1,3,2-dioxaborolan-2-yl)phenyl]isoxazol. $^1$H-NMR (DMSO-d$_6$, 400 MHz) δ 7.95 (d, 1H), 7.35 (d, 2H), 7.23 (s, 1H), 7.22 (d, 1H), 7.06 (d, 1H), 6.86 (d, 1H), 4.64 (s, 2H), 3.52 (d, 2H)

Example 31. 2-[(2E)-2-(aminomethyl)-3-fluoroprop-2-en-1-yl]-7-(6-methoxypyridin-3-yl)[1,2,4]triazolo[4,3-a]pyridin-3(2H)-one hydrochloride 11 mg of the title compound as a colorless solid (yield: 48.5%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 14 mg of 2-methoxy-5-pyridinylboronicacid was used instead of 3-[4-(4,4,5,5-tetramethyl-1,3,2-dioxaborolan-2-yl)phenyl]isoxazol. $^1$H-NMR (DMSO-$d_6$, 400 MHz) δ 8.65 (s, 1H), 8.16 (dd, 1H), 7.96 (t, 1H), 7.58 (s, 1H), 7.24 (d, 1H), 7.05 (dd, 1H), 6.95 (d, 1H), 4.66 (s, 2H), 3.91 (s, 3H), 3.52 (d, 2H)

Example 32. 2-[(2E)-2-(aminomethyl)-3-fluoroprop-2-en-1-yl]-7-[6-(dimethylamino)pyridin-3-yl][1,2,4]triazolo[4,3-a]pyridin-3(2H)-one hydrochloride 9 mg of the title compound as a yellow solid (yield: 38.3%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 23 mg of 6-(dimethylamino)pyridine-3-boronic acid pinacol ester was used instead of 3-[4-(4,4,5,5-tetramethyl-1,3,2-dioxaborolan-2-yl)phenyl]isoxazol. $^1$H-NMR (DMSO-$d_6$, 400 MHz) δ 8.47 (s, 1H), 8.20 (s, 1H), 7.93 (d, 1H), 7.57 (s, 1H), 7.23 (d, 1H), 7.05 (d, 2H), 4.65 (s, 2H), 3.70 (s, 2H), 3.18 (s, 6H)

Example 33. 2-[(2E)-2-(aminomethyl)-3-fluoroprop-2-en-1-yl]-7-[6-(morpholin-4-yl)pyridin-3-yl][1,2,4]triazolo[4,3-a]pyridin-3(2H)-one hydrochloride 15 mg of the title compound as a colorless solid (yield: 47.5%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 33 mg of 6-(morpholin-4-yl)pyridine-3-boronic acid pinacol ester was used instead of 3-[4-(4,4,5,5-tetramethyl-1,3,2-dioxaborolan-2-yl)phenyl]isoxazol. $^1$H-NMR (DMSO-$d_6$, 400 MHz) δ 7.98 (d, 1H), 7.41 (d, 2H), 7.33 (s, 1H), 7.23 (d, 1H), 7.17 (s, 1H), 6.88 (t, 1H), 5.34 (s, 2H), 4.66 (s, 2H), 3.56-3.52 (m, 8H)

Example 34. 2-[(2E)-2-(aminomethyl)-3-fluoroprop-2-en-1-yl]-7-(1,2,3,6-tetrahydropyridin-4-yl)[1,2,4]triazolo[4,3-a]pyridin-3(2H)-one dihydrochloride 7 mg of the title compound as a yellow solid (yield: 24.8%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 35 mg of 1-(tert-butoxycarbonyl)-4-(4,4,5,5-tetramethyl-1,3,2-dioxaborolan-2-yl)-1,2,5,6-tetrahydropyridine was used instead of 3-[4-(4,4,5,5-tetramethyl-1,3,2-dioxaborolan-2-yl)phenyl]isoxazol. $^1$H-NMR (MeOD, 400 MHz) δ 7.82 (d, 1H), 7.21 (s, 1H), 7.20 (d, 1H), 6.94 (d, 1H), 6.49 (s, 1H), 4.66 (s, 2H), 3.92 (s, 2H), 3.72 (s, 2H), 3.48 (t, 2H), 2.79 (s, 2H)

Example 35. 2-[(2E)-2-(aminomethyl)-3-fluoroprop-2-en-1-yl]-7-(1H-pyrrolo[2,3-b]pyridin-3-yl)[1,2,4]triazolo[4,3-a]pyridin-3(2H)-one hydrochloride 10 mg of the title compound as a brown solid (yield: 43.0%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 23 mg of 7-azaindole-3-boronic acid pinacol ester was used instead of 3-[4-(4,4,5,5-tetramethyl-1,3,2-dioxaborolan-2-yl)phenyl]isoxazol. $^1$H-NMR (DMSO-$d_6$, 400 MHz) δ 8.21 (s, 1H), 7.97 (d, 1H), 7.90-7.88 (m, 2H), 7.61 (s, 1H), 7.51 (d, 1H), 7.26 (d, 1H), 7.11 (d, 1H), 4.67 (s, 2H), 3.54 (s, 2H)

Example 36. 2-[(2E)-2-(aminomethyl)-3-fluoroprop-2-en-1-yl]-7-(1,3-benzodioxol-5-yl)[1,2,4]triazolo[4,3-a]pyridin-3(2H)-one hydrochloride 16 mg of the title compound as a colorless solid (yield: 56.3%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 19 mg of 3,4-(methylenedioxy)phenylboronic acid was used instead of 3-[4-(4,4,5,5-tetramethyl-1,3,2-dioxaborolan-2-yl)phenyl]isoxazol. $^1$H-NMR (DMSO-$d_6$, 400 MHz) δ 7.90 (d, 1H), 7.45 (d, 2H), 7.32 (s, 1H), 7.21 (d, 1H), 7.02 (dd, 2H), 6.10 (s, 2H), 4.63 (s, 2H), 3.50 (s, 2H)

Example 37. 2-[(2E)-2-(aminomethyl)-3-fluoroprop-2-en-1-yl]-7-(1H-indazol-6-yl)[1,2,4]triazolo[4,a]pyridin-3(2H)-one hydrochloride 7 mg of the title compound as a brown solid (yield: 30.1%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 15 mg of 1H-indazole-6-boronic acid was used instead of 3-[4-(4,4,5,5-tetramethyl-1,3,2-dioxaborolan-2-yl)phenyl]isoxazol. $^1$H-NMR (DMSO-$d_6$, 400 MHz) δ 8.44 (d, 1H), 8.33 (d, 1H), 8.26 (s, 1H), 7.90 (d, 1H), 7.47 (s, 1H), 7.25 (d, 1H), 7.23 (dd, 1H), 7.15 (d, 1H), 4.64 (s, 2H), 3.54 (s, 2H)

Example 38. 2-[(2E)-2-(aminomethyl)-3-fluoroprop-2-en-1-yl]-7-(2,1,3-benzoxadiazol-5-yl)[1,2,4]triazolo[4,3-a]pyridin-3(2H)-one hydrochloride 16 mg of the title compound as a yellow solid (yield: 56.6%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 28 mg of benzo[c][1,2,5]oxadiazole-5-boronic acid pinacol ester was used instead of 3-[4-(4,4,5,5-tetramethyl-1,3,2-dioxaborolan-2-yl)phenyl]isoxazol. $^1$H-NMR (DMSO-$d_6$, 400 MHz) δ 8.54 (s, 1H), 8.20 (d, 1H), 8.09 (d, 1H), 8.03 (d, 1H), 7.87 (s, 1H), 7.25 (d, 1H), 7.20 (d, 1H), 4.68 (s, 2H), 3.52 (s, 2H)

Example 39. 2-[(2E)-2-(aminomethyl)-3-fluoroprop-2-en-1-yl]-7-(1H-benzotriazol-6-yl)[1,2,4]triazolo[4,3-a]pyridin-3(2H)-one hydrochloride 9 mg of the title compound as a yellow solid (yield: 38.6%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 23 mg of 1H-benzo[d][1,2,3]triazol-5-ylboronicacid pinacol ester was used instead of 3-[4-(4,4,5,5-tetramethyl-1,3,2-dioxaborolan-2-yl)phenyl]isoxazol. $^1$H-NMR (DMSO-$d_6$, 400 MHz) δ 8.11-8.05 (m, 2H), 7.99 (d, 2H), 7.68 (s, 1H), 7.26 (d, 1H), 7.16 (s, 1H), 4.66 (s, 2H), 3.55 (s, 2H)

Example 40. 2-[(2E)-2-(aminomethyl)-3-fluoroprop-2-en-1-yl]-7-(1H-pyrrolo[2,3-b]pyridin-4-yl)[1,2,4]triazolo[4,3-a]pyridin-3(2H)-one hydrochloride 10 mg of the title compound as a yellow solid (yield: 43.0%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 23 mg of 4-(tetramethyl-1,3,2-dioxaborolan-2-yl)-1H-pyrrolo[2,3-b]pyridine was used instead of 3-[4-(4,4,5,5-tetramethyl-1,3,2-dioxaborolan-2-yl)phenyl]isoxazol. $^1$H-NMR (DMSO-$d_6$, 400 MHz) δ 8.36 (d, 1H), 8.02 (d, 1H), 7.64 (d, 1H), 7.59 (s, 1H), 7.30 (d, 1H), 7.27 (d, 1H), 7.05 (dd, 1H), 6.61 (s, 1H), 4.69 (s, 2H), 3.62 (s, 2H)

Example 41. 7-[2-[(2E)-2-(aminomethyl)-3-fluoroprop-2-en-1-yl]-3-oxo-2,3-dihydro[1,2,4]triazolo[4,3-a]pyridin-7-yl]-1,4-dihydro-2H-3,1-benzoxazin-2-one hydrochloride 13 mg of the title compound as a brown solid (yield: 42.7%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 31 mg of 2-oxo-2,4-dihydrobenzo[d][1,3]oxazine-7-boronic acid pinacol ester was used instead of 3-[4-(4,4,5,5-tetramethyl-1,3,2-dioxaborolan-2-yl)phenyl]isoxazol. $^1$H-NMR (MeOD, 400 MHz) δ 7.94 (t, 1H), 7.61 (dd, 1H), 7.53 (d, 1H), 7.41 (s, 1H), 7.33 (d, 1H), 7.15 (d, 1H), 7.02 (t, 1H), 5.38 (s, 2H), 4.69 (s, 2H), 3.74 (s, 2H)

Example 42. 6-[2-[(2E)-2-(aminomethyl)-3-fluoroprop-2-en-1-yl]-3-oxo-2,3-dihydro[1,2,4]triazolo[4,3-a]pyridin-7-yl]-2H-1,4-benzoxazine-3 (4H)-one hydrochloride 12 mg of the title compound as a colorless solid (yield: 39.4%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 31 mg of 6-(4,4,5,5-tetramethyl-1,3,2-dioxaborolan-2-yl)-2H-benzo[b][1,4]oxazine-3(4H)-one was used instead of 3-[4-(4,4,5,5-tetramethyl-1,3,2-dioxaborolan-2-yl)phenyl]isoxazol. $^1$H-NMR (DMSO-$d_6$, 400 MHz) δ 10.89 (s, 1H), 7.95 (d, 1H), 7.35 (d, 2H), 7.23 (s, 1H), 7.22 (d, 1H), 7.06 (d, 1H), 6.86 (d, 1H), 4.64 (s, 4H), 3.52 (d, 2H)

Example 43. 6-[2-[(2E)-2-(aminomethyl)-3-fluoroprop-2-en-1-yl]-3-oxo-2,3-dihydro[1,2,4]triazolo[4,3-a]pyridin-7-yl]-8-methyl-3,4-dihydroquinolin-2 (1H)-one hydrochloride 16 mg of the title compound as a brown solid (yield: 51.0%) was prepared in the same fashion as Example 7 except that in Step 1, 30 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 32 mg of 8-methyl-2-oxo-1,2,3,4-tetrahydroquinoline-6-boronic acid pinacol ester was used instead of 3-[4-(4,4,5,5-tetramethyl-1,3,2-dioxaborolan-2-yl)phenyl]isoxazol. $^1$H-NMR (DMSO-$d_6$, 400 MHz) δ 9.63 (s, 1H), 7.92 (d, 1H), 7.50 (d, 2H), 7.46 (s, 1H), 7.24 (d, 1H), 7.02 (d, 1H), 4.64 (s, 2H), 3.53 (s, 2H), 2.94 (t, 2H), 2.49 (t, 2H), 2.28 (s, 3H)

Example 44. 2-[(2E)-2-(aminomethyl)-3-fluoroprop-2-en-1-yl]-7-(4-methyl-3,4-dihydro-2H-1,4-benzoxazin-7-yl)[1,2,4]triazolo[4,3-a]pyridin-3(2H)-one hydrochloride 6 mg of the title compound as a yellow solid (yield: 23.8%) was prepared in the same fashion as Example 7 except that in Step 1, 25 mg of tert-butyl N-[(E)-2-[(7-bromo-3-oxo-[1,2,4]triazolo[4,3-a]pyridin-2-yl)methyl]-3-fluoro-allyl]carbamate prepared in Reference Example 8 was used instead of tert-butyl N-[(E)-2-[(6-bromo-3-oxo-[1,2,4]triazolo[4,3-a]pyridin-2-yl)methyl]-3-fluoro-allyl]carbamate and 26 mg of 4-methyl-7-(4,4,5,5-tetramethyl-1,3,2-dioxaborolan-2-yl)-3,4-dihydro-2H-1,4-benzoxazine was used instead of 3-[4-(4,4,5,5-tetramethyl-1,3,2-dioxaborolan-2-yl)phenyl]isoxazol. $^1$H-NMR (DMSO-$d_6$, 400 MHz) δ 7.84 (d, 1H), 7.35 (s, 1H), 7.27 (dd, 1H), 7.24 (d, 1H), 7.15 (s, 1H), 6.98 (d, 1H), 6.77 (d, 1H), 4.62 (s, 2H), 4.25 (t, 2H), 3.55-3.36 (m, 2H), 3.34 (s, 2H), 2.91 (s, 3H)

Example 45. 2-[2-(aminomethyl)-3,3-difluoro-allyl]-5-bromo-[1,2,4]triazolo[4,3-a]pyridin-3-one trifluoroacetate 50 mg of tert-butyl N-[2-[(5-bromo-3-oxo-[1,2,4]triazolo[4,3-a]pyridin-2-yl)methyl]-3,3-difluoro-allyl]carbamate prepared in Reference Example 9 was dissolved in 2.0 mL of dichloromethane, followed by the addition of 0.2 mL of trifluoroacetic acid. The resulting solution was stirred at room temperature for 3 hours. The reaction mixture thus obtained was concentrated, followed by the addition of dichloromethane. The solution was concentrated under reduced pressure and then dried in vacuo to obtain a yellow liquid residue. The residue was purified with silica gel column chromatography (developing solvent: dichloromethane/methanol=10/1) to give 29 mg of the title compound as a white solid (yield: 74.8%). $^1$H-NMR (MeOD, 400 MHz) δ 7.15 (d, 1H), 7.04 (t, 1H), 6.81 (d, 1H), 4.75 (s, 2H), 3.72 (s, 2H)

Example 46. 2-[2-(aminomethyl)-3,3-difluoro-allyl]-6-bromo-[1,2,4]triazolo[4,3-a]pyridin-3-one trifluoroacetate 20 mg of the title compound as a white solid (yield: 48.7%) was prepared in the same fashion as Example 45 except that 50 mg of tert-butyl N-[2-[(6-bromo-3-oxo-[1,2,4]triazolo[4,3-a]pyridin-2-yl)methyl]-3,3-difluoro-allyl]carbamate prepared in Reference Example 10 was used instead of tert-butyl N-[2-[(5-bromo-3-oxo-[1,2,4]triazolo[4,3-a]pyridin-2-yl)methyl]-3,3-difluoro-allyl]carbamate.
$^1$H-NMR (MeOD, 400 MHz) δ 8.08 (s, 1H), 7.34 (d, 1H), 7.19 (d, 1H), 4.78 (s, 2H), 3.72 (s, 2H)

Example 47. 2-[2-(aminomethyl)-3,3-difluoro-allyl]-7-bromo-[1,2,4]triazolo[4,3-a]pyridin-3-one trifluoroacetate 36 mg of the title compound as a white solid (yield: 92.2%) was prepared in the same fashion as Example 45 except that 50 mg of tert-butyl N-[2-[(7-bromo-3-oxo-[1,2,4]triazolo[4,3-a]pyridin-2-yl)methyl]-3,3-difluoro-allyl]carbamate prepared in Reference Example 11 was used instead of tert-butyl N-[2-[(5-bromo-3-oxo-[1,2,4]triazolo[4,3-a]pyridin-2-yl)methyl]-3,3-difluoro-allyl]carbamate.
$^1$H-NMR (MeOD, 400 MHz) δ 7.78 (d, 1H), 7.52 (s, 1H), 6.80 (d, 1H), 4.76 (s, 2H), 3.73 (s, 2H)

Example 48. 2-[2-(aminomethyl)-3,3-difluoro-allyl]-7-(4-methylsulfonylphenyl)-[1,2,4]triazolo[4,3-a]pyridin-3-one trifluoroacetate Step 1: tert-butyl N-[3,3-difluoro-2-[[7-(4-methylsulfonylphenyl)-3-oxo-[1,2,4]triazolo[4,3-a]pyridin-2-yl]methyl]allyl]carbamate 50 mg of tert-butyl N-[2-[(7-bromo-3-oxo-[1,2,4]triazolo[4,3-a]pyridin-2-yl)methyl]-3,3-difluoro-allyl]carbamate prepared in Reference Example 11 and 29 mg of 4-(methanesulfonyl)phenylboronic acid were dissolved in 1.0 mL of 1,4-dioxane, followed by the addition of 358 uL of 1 M potassium carbonate and 3 mg of palladiumdi[1,1'-bis(diphenylphospino)ferrocene]dichloride (PdCl$_2$(dppf)). The resulting solution was stirred overnight at 90° C. The resulting reaction mixture was filtered through a celite pad and concentrated under reduced pressure to give a residue. The residue thus obtained was dissolved in ethylacetate, washed with distilled water, dried over anhydrous magnesium sulfate, and concentrated under reduced pressure to give a yellow liquid residue. The residue was purified with silica gel column chromatography (developing solvent: n-hexane/ethyl acetate=1/2) to give 57 mg of the title compound (yield: 96.1%). MS (ESI) m/z=395.1 (M+H)+

Step 2: 2-[2-(aminomethyl)-3,3-difluoro-allyl]-4-[3-(4-methylsulfonylphenyl)phenyl]-1,2,4-triazol-3-one trifluoroacetate 57 mg of tert-butyl N-[3,3-difluoro-2-[[7-(4-methylsulfonylphenyl)-3-oxo-[1,2,4]triazolo[4,3-a]pyridin-2-yl]methyl]allyl]carbamate prepared in Step 1 was dissolved in 2.0 mL of dichloromethane, followed by the addition of 0.2 mL of trifluoroacetic acid. The resulting solution was stirred at room temperature for 1.5 hours. The reaction mixture thus obtained was concentrated, followed by the addition of dichloromethane. The solution was concentrated under reduced pressure and then dried in vacuo to obtain a yellow liquid residue. The residue was purified with silica gel column chromatography (developing solvent: dichloromethane/methanol=10/1) to give 35 mg of the title compound (yield: 74.0%). $^1$H-NMR (MeOD, 400 MHz) δ 8.05 (d, 2H), 7.95 (d, 3H), 7.54 (s, 1H), 7.06 (d, 1H), 4.82 (s, 2H), 3.77 (s, 2H), 3.17 (s, 3H)

Example 49. 2-[2-(aminomethyl)-3,3-difluoro-allyl]-7-(4-piperazin-1-ylphenyl)-[1,2,4]triazolo[4,3-a]pyridin-3-one ditrifluoroacetate 32 mg of the title compound (yield: 66.6%) was prepared in the same fashion as Example 48 except that in Step 1, 56 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 7.86 (d, 1H), 7.68 (d, 2H), 7.35 (s, 1H), 7.13 (d, 2H), 7.05 (d, 1H), 4.79 (s, 2H), 3.75 (s, 2H), 3.53 (s, 4H), 3.40 (s, 4H)

Example 50. 2-[2-(aminomethyl)-3,3-difluoro-allyl]-7-[6-(trifluoromethyl)-3-pyridyl]-[1,2,4]triazolo[4,3-a]pyridin-3-one trifluoroacetate 29 mg of the title compound (yield: 62.7%) was prepared in the same fashion as Example 48 except that in Step 1, 27 mg of 2-(trifluoromethyl)pyridine-5-boronic acid was used instead of 4-(methanesulfonyl)phenylboronic acid. $^1$H-NMR (MeOD, 400 MHz) δ 9.08 (s, 1H), 8.38 (d, 1H), 8.00 (d, 1H), 7.95 (d, 1H), 7.66 (s, 1H), 7.10 (d, 1H), 4.83 (s, 2H), 3.77 (s, 2H)

Example 51. 2-[2-(aminomethyl)-3,3-difluoro-allyl]-7-[6-(dimethylamino)-3-pyridyl]-[1,2,4]triazolo[4,3-a]pyridin-3-one trifluoroacetate 31 mg of the title compound (yield: 71.7%) was prepared in the same fashion as Example 48 except that in Step 1, 36 mg of 6-(dimethylamino)pyridine-3-boronic acid pinacol ester was used instead of 4-(methanesulfonyl)phenylboronic acid. $^1$H-NMR (MeOD, 400 MHz) δ 8.36 (s, 1H), 8.22 (d, 1H), 7.90 (d, 1H), 7.46 (s, 1H), 7.18 (d, 1H), 7.02 (d, 1H), 4.80 (s, 2H), 3.76 (s, 2H), 3.30 (s, 6H)

Example 52. 2-[2-(aminomethyl)-3,3-difluoro-allyl]-7-(1,3-benzodioxol-5-yl)-[1,2,4]triazolo[4,3-a]pyridin-3-one trifluoroacetate 29 mg of the title compound (yield: 67.1%) was prepared in the same fashion as Example 48 except that in Step 1, 24 mg of 3,4-(methylenedioxy)phenylboronic acid was used instead of 4-(methanesulfonyl)phenylboronic acid.

$^1$H-NMR (MeOD, 400 MHz) δ 7.88 (d, 1H), 7.35 (s, 1H), 7.25 (d, 2H), 7.02 (d, 1H), 6.95 (d, 1H), 6.05 (s, 2H), 4.79 (s, 2H), 3.74 (s, 2H)

Example 53. 6-[2-[2-(aminomethyl)-3,3-difluoro-allyl]-3-oxo-[1,2,4]triazolo[4,3-a]pyridin-7-yl]-8-methyl-3,4-dihydro-1H-quinolin-2-one trifluoroacetate 33 mg of the title compound (yield: 68.8%) was prepared in the same fashion as Example 48 except that in Step 1, 41 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 7.87 (d, 1H), 7.43 (s, 2H), 7.38 (s, 1H), 7.05 (d, 1H), 4.80 (s, 2H), 3.75 (s, 2H), 3.02 (t, 2H), 2.60 (t, 2H), 2.33 (s, 2H)

Example 54. 6-[2-[2-(aminomethyl)-3,3-difluoro-allyl]-3-oxo-[1,2,4]triazolo[4,3-a]pyridin-7-yl]-1-methyl-3,4-dihydroquinolin-2-one trifluoroacetate 35 mg of the title compound (yield: 73.0%) was prepared in the same fashion as Example 48 except that in Step 1, 41 mg of (1-methyl-2-oxo-1,2,3,4-tetrahydroquinolin-6-yl)boronic acid pinacol ester was used instead of 4-(methanesulfonyl)phenylboronic acid. $^1$H-NMR (MeOD, 400 MHz) δ 7.92 (d, 1H), 7.68 (d, 1H), 7.64 (s, 1H), 7.44 (s, 1H), 7.25 (d, 1H), 7.09 (d, 1H), 4.80 (s, 2H), 3.75 (s, 2H), 3.40 (s, 3H), 3.02 (t, 2H), 2.68 (t, 2H)

Example 55. 2-[2-(aminomethyl)-3,3-difluoro-allyl]-7-(1-ethylpyrazol-4-yl)-[1,2,4]triazolo[4,3-a]pyridin-3-one trifluoroacetate 35 mg of the title compound (yield: 87.2%) was prepared in the same fashion as Example 48 except that in Step 1, 32 mg of 1-ethyl-4-(4,4,5,5-tetramethyl-1,3,2-dioxaborolan-2-yl)-1H-pyrazole was used instead of 4-(methanesulfonyl)phenylboronic acid. $^1$H-NMR (MeOD, 400 MHz) δ 8.21 (s, 1H), 7.96 (s, 1H), 7.80 (d, 1H), 7.32 (s, 1H), 6.96 (d, 1H), 4.76 (s, 2H), 4.23 (d, 2H), 3.75 (s, 2H), 1.50 (t, 3H)

Example 56. 2-[2-(aminomethyl)-3,3-difluoro-allyl]-7-[2-(1-methylpyrazol-4-yl)ethynyl]-[1,2,4]triazolo[4,3-a]pyridin-3-one trifluoroacetate Step 1: tert-butyl N-[3,3-difluoro-2-[[7-[2-(1-methylpyrazol-4-yl)ethynyl]-3-oxo-[1,2,4]triazolo[4,3-a]pyridin-2-yl]methyl]allyl]carbamate 30.0 mg of tert-butyl N-[2-[(7-bromo-3-oxo-[1,2,4]triazolo[4,3-a]pyridin-2-yl)methyl]-3,3-difluoro-allyl]carbamate prepared in Reference Example 11, 19.0 mg of 4-ethynyl-1-methyl-1H-pyrazole, 4.1 mg of tetrakis(triphenylphosphine) palladium (Pd(PPh$_3$)$_4$), and 1.4 mg of copper (I) iodide (CuI) were dissolved in 0.7 mL of N,N-dimethylformamide. To the resulting solution, 30.0 uL of triethylamine was added and then the solution was stirred overnight at 90° C. The resulting reaction mixture was filtered through a celite pad and concentrated under reduced pressure to give a residue. The residue thus obtained was dissolved in ethyl acetate, washed with distilled water, dried over anhydrous magnesium sulfate, and concentrated under reduced pressure to give a yellow liquid residue. The residue was purified with silica gel column chromatography (developing solvent: n-hexane/ethyl acetate=1/2) to give 20.4 mg of the title compound as a liquid (yield: 64.1%). MS (ESI) m/z=345.1 (M+H)+

Step 2: 2-[2-(aminomethyl)-3,3-difluoro-allyl]-7-[2-(1-methylpyrazol-4-yl)ethynyl]-[1,2,4]triazolo[4,3-a]pyridin-3-one trifluoroacetate 20.4 mg of tert-butyl N-[3,3-difluoro-2-[[7-[2-(1-methylpyrazol-4-yl)ethynyl]-3-oxo-[1,2,4]triazolo[4,3-a]pyridin-2-yl]methyl]allyl]carbamate prepared in Step 1 was dissolved in 1.0 mL of dichloromethane, and 0.1 mL of trifluoroacetic acid was added thereto. The solution was stirred at room temperature for 2 hours. The residue obtained by concentration under reduced pressure was dissolved in dichloromethane, and the solution thus obtained was concentrated under reduced pressure and then dried in vacuo to obtain a yellow liquid residue. The residue was purified with silica gel column chromatography (developing solvent: dichloromethane/methanol=10/1) to give 14.4 mg of the title compound as a solid. $^1$H-NMR (MeOD, 400 MHz) δ 7.93 (s, 1H), 7.82 (d, 1H), 7.69 (s, 1H), 7.30 (s, 1H), 6.67 (d, 1H), 4.79 (s, 2H), 3.93 (s, 3H), 3.74 (s, 2H)

Example 57. 2-[2-(aminomethyl)-3,3-difluoro-allyl]-7-[2-[6-(dimethylamino)-3-pyridyl]ethynyl]-[1,2,4]triazolo[4,3-a]pyridin-3-one trifluoroacetate The title compound (13.7 mg) was prepared in the same fashion as Example 56 except that in Step 1, 26.2 mg of 5-ethynyl-N,N-dimethylpyridin-2-amine was used instead of 4-ethynyl-1-methyl-1H-pyrazole. 1H-NMR (MeOD, 400 MHz) δ 8.26 (d, 1H), 7.81 (d, 1H), 7.65 (dd, 1H), 7.30 (s, 1H), 6.70 (d, 1H), 6.68 (d, 1H), 4.79 (s, 2H), 3.74 (s, 2H), 3.15 (s, 6H)

Example 58. 2-[2-(aminomethyl)-3,3-difluoro-allyl]-7-[2-(6-morpholino-3-pyridyl)ethynyl]-[1,2,4]triazolo[4,3-a]pyridin-3-one trifluoroacetate The title compound (23.1 mg) was prepared in the same fashion as Example 56 except that in Step 1, 33.7 mg of 4-(5-ethynylpyridin-2-yl)morpholine was used instead of 4-ethynyl-1-methyl-1H-pyrazole. 1H-NMR (MeOD, 400 MHz) δ 8.31 (s, 1H), 7.81 (dd, 1H), 7.67 (dd, 1H), 7.32 (s, 1H), 6.82 (d, 1H), 6.68 (dd, 1H), 4.79 (s, 2H), 3.79 (t, 4H), 3.74 (s, 2H), 3.59 (t, 4H)

Example 59. 2-[2-(aminomethyl)-3,3-difluoro-allyl]-7-[2-(3,4-dihydro-2H-1,4-benzoxazin-6-yl)ethynyl]-[1,2,4]triazolo[4,3-a]pyridin-3-one ditrifluoroacetate The title compound (11.4 mg) was prepared in the same fashion as Example 56 except that in Step 1, 46.4 mg of tert-butyl 6-ethynyl-2H-benzo[b][1,4]oxazine-4(3H)-carboxylate was used instead of 4-ethynyl-1-methyl-1H-pyrazole. $^1$H-NMR (MeOD, 400 MHz) δ 7.81 (d, 1H), 7.29 (s, 1H), 6.77 (d, 1H), 6.74 (d, 1H), 6.70-6.65 (m, 3H), 4.78 (s, 2H), 4.23 (t, 2H), 3.72 (s, 2H), 3.37 (d, 2H)

Example 60. 2-[2-(aminomethyl)-3,3-difluoro-allyl]-7-[2-(2,3-dihydro-1H-pyrido[2,3-b][1,4]oxazin-7-yl)ethynyl]-[1,2,4]triazolo[4,3-a]pyridin-3-one ditrifluoroacetate The title compound (15.1 mg) was prepared in the same fashion as Example 56 except that in Step 1, 28.6 mg of 7-ethynyl-2,3-dihydro-1H-pyrido[2,3-b][1,4]oxazine was used instead of 4-ethynyl-1-methyl-1H-pyrazole. $^1$H-NMR (MeOD, 400 MHz) δ 7.83 (d, 1H), 7.60 (s, 1H), 7.37 (s, 1H), 7.08 (s, 1H), 6.70 (d, 1H), 4.79 (s, 2H), 4.42 (t, 2H), 3.74 (s, 2H), 3.40 (t, 2H)

Example 61. 2-[2-(aminomethyl)-3,3-difluoro-allyl]-7-[2-(3,4-dihydro-2H-pyrido[3,2-b][1,4]oxazin-7-yl)ethynyl]-[1,2,4]triazolo[4,3-a]pyridin-3-one ditrifluoroacetate The title compound (10.7 mg) was prepared in the same fashion as Example 56 except that in Step 1, 28.6 mg of 7-ethynyl-2H,3H,4H-pyrido[3,2-b][1,4]oxazine was used instead of 4-ethynyl-1-methyl-1H-pyrazole. $^1$H-NMR (MeOD, 400 MHz) δ 7.80 (t, 2H), 7.32 (s, 1H), 7.10 (s, 1H), 6.68 (dd, 1H), 4.79 (s, 2H), 4.20 (t, 2H), 3.74 (s, 2H), 3.57 (t, 2H)

Example 62. 6-[2-[2-[2-(aminomethyl)-3,3-difluoro-allyl]-3-oxo-[1,2,4]triazolo[4,3-a]pyridin-7-yl]ethynyl]-3,4-dihydro-1H-quinolin-2-one trifluoroacetate The title compound (16.7 mg) was prepared in the same fashion as Example 56 except that in Step 1, 30.6 mg of 6-ethynyl-1,2,3,4-tetrahydroquinolin-2-one was used instead of 4-ethynyl-1-methyl-1H-pyrazole. $^1$H-NMR (MeOD, 400 MHz) δ 7.84 (d, 1H), 7.41 (t, 2H), 7.36 (s, 1H), 6.91 (d, 1H), 6.71 (d, 1H), 4.79 (s, 2H), 3.74 (s, 2H), 3.00 (t, 2H), 2.61 (t, 2H)

Example 63. 2-[2-(aminomethyl)-3,3-difluoro-allyl]-7-[2-(4-methyl-2,3-dihydro-1,4-benzoxazin-7-yl)ethynyl]-[1,2,4]triazolo[4,3-a]pyridin-3-one trifluoroacetate The title compound (17.5 mg) was prepared in the same fashion as Example 56 except that in Step 1, 31.0 mg of 7-ethynyl-4-methyl-2,3-dihydro-1,4-benzoxazine was used instead of 4-ethynyl-1-methyl-1H-pyrazole. $^1$H-NMR (MeOD, 400 MHz) δ 7.77 (d, 1H), 7.62 (dd, 1H), 7.36 (s, 1H), 7.08 (s, 1H), 6.71 (d, 1H), 6.61 (d, 1H), 4.77 (s, 2H), 4.23 (t, 4H), 3.72 (s, 2H), 3.43 (t, 2H), 3.02 (s, 3H)

Compounds from the Examples are shown in Table 1.

TABLE 1

| Ex No | Structure | Chemical Name* |
|---|---|---|
| 1 | 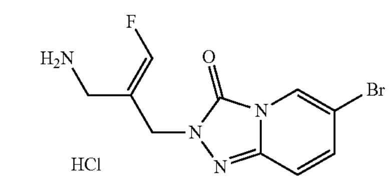 [SMILES: NC/C(=C\F)Cn1nc2ccc(Br)cn2c1=O ; Cl] | 2-[(2E)-2-(aminomethyl)-3-fluoroprop-2-en-1-yl]-6-bromo[1,2,4]triazolo[4,3-a]pyridin-3(2H)-one hydrochloride |
| 2 | 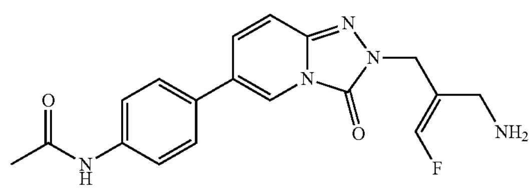 [SMILES: CC(=O)Nc1ccc(-c2ccc3nn(C/C(=C/F)CN)c(=O)n3c2)cc1] | N-(4-{2-[(2E)-2-(aminomethyl)-3-fluoroprop-2-en-1-yl]-3-oxo-2,3-dihydro[1,2,4]triazolo[4,3-a]pyridin-6-yl}phenyl)acetamide |
| 3 | 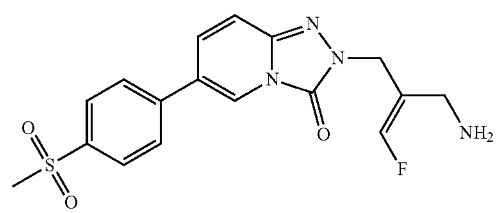 [SMILES: CS(=O)(=O)c1ccc(-c2ccc3nn(C/C(=C/F)CN)c(=O)n3c2)cc1] | 2-[(2E)-2-(aminomethyl)-3-fluoroprop-2-en-1-yl]-6-[4-(methylsulfonyl)phenyl][1,2,4]triazolo[4,3-a]pyridin-3(2H)-one |
| 4 | 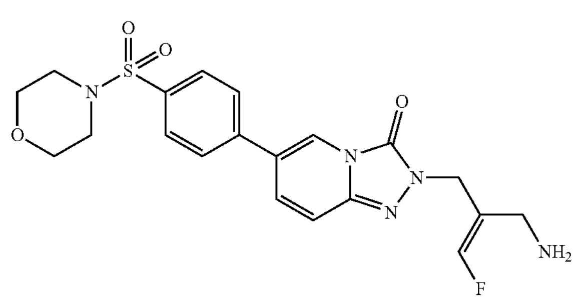 [SMILES: NC/C(=C\F)Cn1nc2ccc(-c3ccc(S(=O)(=O)N4CCOCC4)cc3)cn2c1=O] | 2-[(2E)-2-(aminomethyl)-3-fluoroprop-2-en-1-yl]-6-[4-(morpholin-4-ylsulfonyl)phenyl][1,2,4]triazolo[4,3-a]pyridin-3(2H)-one |

TABLE 1-continued

| Ex No | Structure | Chemical Name* |
|---|---|---|
| 5 | 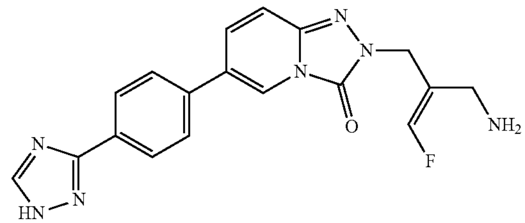 [SMILES: NC/C(=C\F)Cn1nc2ccc(-c3ccc(-c4nc[nH]n4)cc3)cn2c1=O] | 2-[(2E)-2-(aminomethyl)-3-fluoroprop-2-en-1-yl]-6-[4-(1H-1,2,4-triazol-3-yl)phenyl][1,2,4]triazolo[4,3-a]pyridin-3(2H)-one |
| 6 | 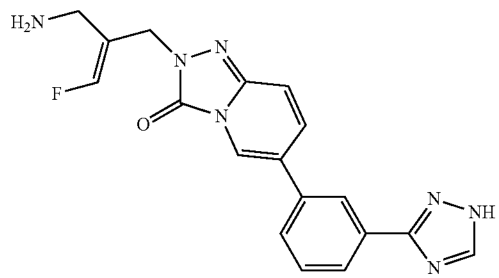 [SMILES: NC/C(=C\F)Cn1nc2ccc(-c3cccc(-c4nc[nH]n4)c3)cn2c1=O] | 2-[(2E)-2-(aminomethyl)-3-fluoroprop-2-en-1-yl]-6-[3-(1H-1,2,4-triazol-3-yl)phenyl][1,2,4]triazolo[4,3-a]pyridin-3(2H)-one |
| 7 | 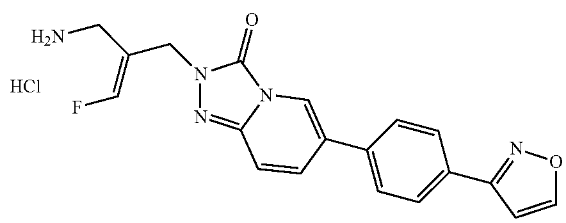 [SMILES: Cl ; NC/C(=C\F)Cn1nc2ccc(-c3ccc(-c4ccon4)cc3)cn2c1=O] | 2-[(2E)-2-(aminomethyl)-3-fluoroprop-2-en-1-yl]-6-[4-(1,2-oxazol-3-yl)phenyl][1,2,4]triazolo[4,3-a]pyridin-3(2H)-one hydrochloride |
| 8 | 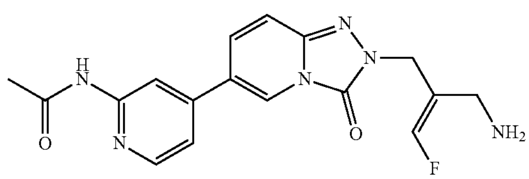 [SMILES: CC(=O)Nc1cc(-c2ccc3nn(C/C(=C/F)CN)c(=O)n3c2)ccn1] | N-(4-{2-[(2E)-2-(aminomethyl)-3-fluoroprop-2-en-1-yl]-3-oxo-2,3-dihydro[1,2,4]triazolo[4,3-a]pyridin-6-yl}pyridin-2-yl)acetamide |
| 9 | 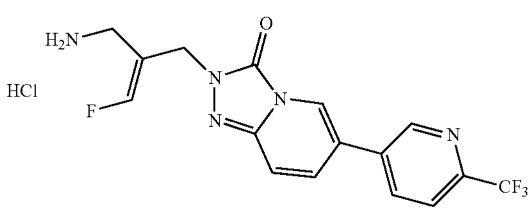 [SMILES: Cl ; NC/C(=C\F)Cn1nc2ccc(-c3ccc(C(F)(F)F)nc3)cn2c1=O] | 2-[(2E)-2-(aminomethyl)-3-fluoroprop-2-en-1-yl]-6-[6-(trifluoromethyl)pyridin-3-yl][1,2,4]triazolo[4,3-a]pyridin-3(2H)-one hydrochloride |
| 10 | 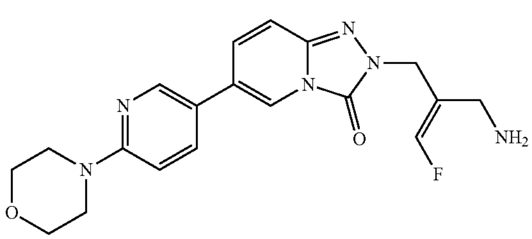 [SMILES: NC/C(=C\F)Cn1nc2ccc(-c3ccc(N4CCOCC4)nc3)cn2c1=O] | 2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one |
| 11 | 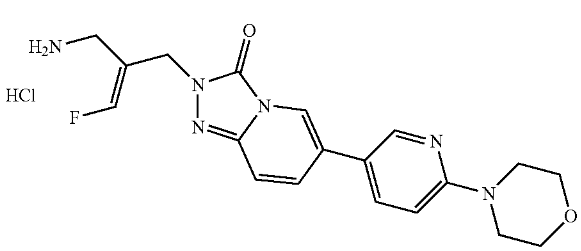 [SMILES: Cl ; NC/C(=C\F)Cn1nc2ccc(-c3ccc(N4CCOCC4)nc3)cn2c1=O] | 2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one hydrochloride |

TABLE 1-continued

| Ex No | Structure | Chemical Name* |
|---|---|---|
| 12 | 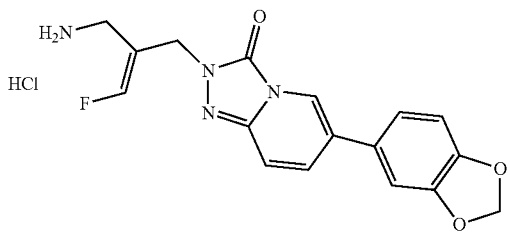 [SMILES: Cl ; NC/C(=C\F)Cn1nc2ccc(-c3ccc4c(c3)OCO4)cn2c1=O] | 2-[(2E)-2-(aminomethyl)-3-fluoroprop-2-en-1-yl]-6-(1,3-benzodioxol-5-yl)[1,2,4]triazolo[4,3-a]pyridin-3(2H)-one hydrochloride |
| 13 | 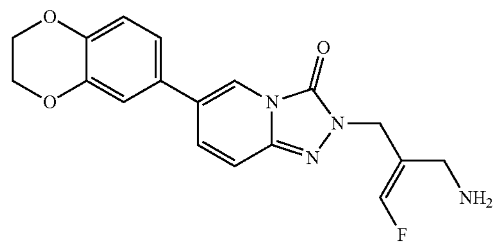 [SMILES: NC/C(=C\F)Cn1nc2ccc(-c3ccc4c(c3)OCCO4)cn2c1=O] | 2-[(2E)-2-(aminomethyl)-3-fluoroprop-2-en-1-yl]-6-(2,3-dihydro-1,4-benzodioxin-6-yl)[1,2,4]triazolo[4,3-a]pyridin-3(2H)-one |
| 14 | 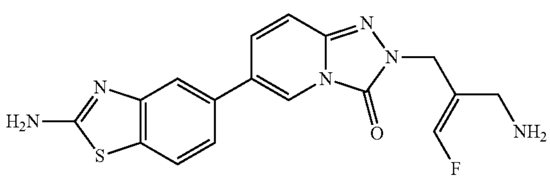 [SMILES: NC/C(=C\F)Cn1nc2ccc(-c3ccc4sc(N)nc4c3)cn2c1=O] | 6-(2-amino-1,3-benzothiazol-5-yl)-2-[(2E)-2-(aminomethyl)-3-fluoroprop-2-en-1-yl][1,2,4]triazolo[4,3-a]pyridin-3(2H)-one |
| 15 | 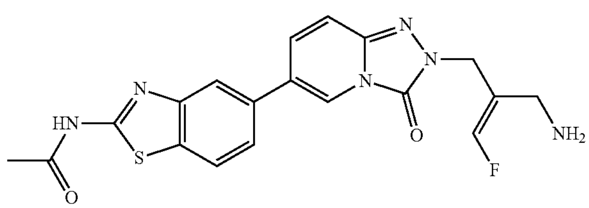 [SMILES: CC(=O)Nc1nc2cc(-c3ccc4nn(C/C(=C/F)CN)c(=O)n4c3)ccc2s1] | N-(5-{2-[(2E)-2-(aminomethyl)-3-fluoroprop-2-en-1-yl]-3-oxo-2,3-dihydro[1,2,4]triazolo[4,3-a]pyridin-6-yl}-1,3-benzothiazol-2-yl)acetamide |
| 16 | 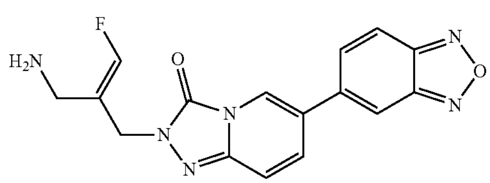 [SMILES: NC/C(=C\F)Cn1nc2ccc(-c3ccc4nonc4c3)cn2c1=O] | 2-[(2E)-2-(aminomethyl)-3-fluoroprop-2-en-1-yl]-6-(2,1,3-benzoxadiazol-5-yl)[1,2,4]triazolo[4,3-a]pyridin-3(2H)-one |
| 17 | 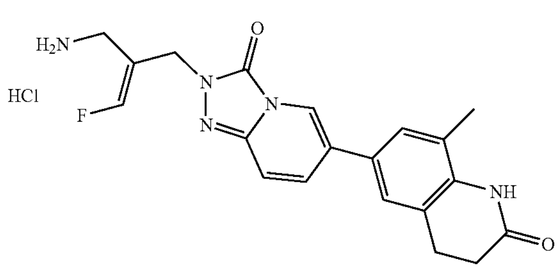 [SMILES: Cl ; Cc1cc(-c2ccc3nn(C/C(=C/F)CN)c(=O)n3c2)cc2c1NC(=O)CC2] | 6-{2-[(2E)-2-(aminomethyl)-3-fluoroprop-2-en-1-yl]-3-oxo-2,3-dihydro[1,2,4]triazolo[4,3-a]pyridin-6-yl}-8-methyl-3,4-dihydroquinolin-2(1H)-one hydrochloride |

TABLE 1-continued

| Ex No | Structure | Chemical Name* |
|---|---|---|
| 18 | 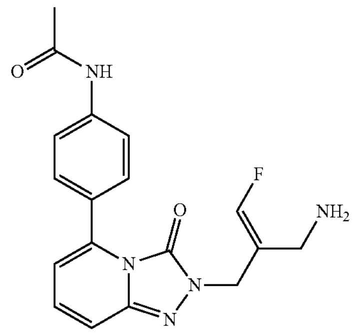 [SMILES: CC(=O)Nc1ccc(-c2cccc3nn(C/C(=C/F)CN)c(=O)n23)cc1] | N-(4-{2-[(2E)-2-(aminomethyl)-3-fluoroprop-2-en-1-yl]-3-oxo-2,3-dihydro[1,2,4]triazolo[4,3-a]pyridin-5-yl}phenyl)acetamide |
| 19 | 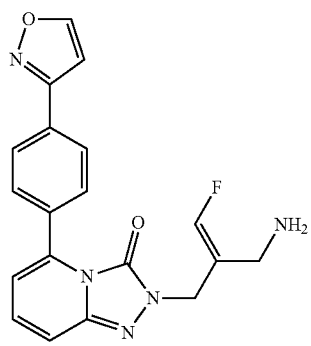 [SMILES: NC/C(=C\F)Cn1nc2cccc(-c3ccc(-c4ccon4)cc3)n2c1=O] | 2-[(2E)-2-(aminomethyl)-3-fluoroprop-2-en-1-yl]-5-[4-(1,2-oxazol-3-yl)phenyl][1,2,4]triazolo[4,3-a]pyridin-3(2H)-one |
| 20 | 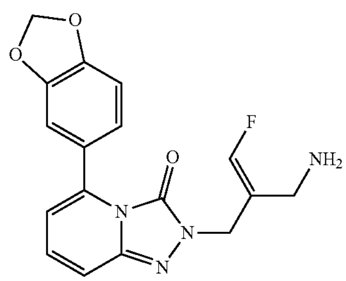 [SMILES: NC/C(=C\F)Cn1nc2cccc(-c3ccc4c(c3)OCO4)n2c1=O] | 2-[(2E)-2-(aminomethyl)-3-fluoroprop-2-en-1-yl]-5-(1,3-benzodioxol-5-yl)[1,2,4]triazolo[4,3-a]pyridin-3(2H)-one |
| 21 | 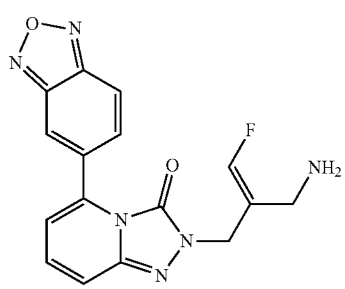 [SMILES: NC/C(=C\F)Cn1nc2cccc(-c3ccc4nonc4c3)n2c1=O] | 2-[(2E)-2-(aminomethyl)-3-fluoroprop-2-en-1-yl]-5-(2,1,3-benzoxadiazol-5-yl)[1,2,4]triazolo[4,3-a]pyridin-3(2H)-one |
| 22 | 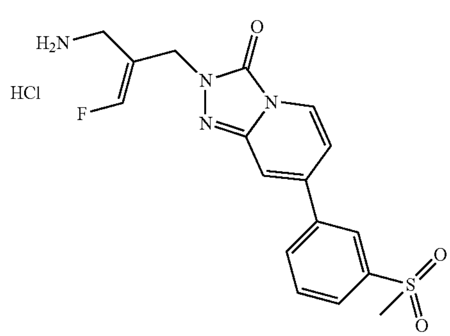 [SMILES: Cl ; CS(=O)(=O)c1cccc(-c2ccn3c(=O)n(C/C(=C/F)CN)nc3c2)c1] | 2-[(2E)-2-(aminomethyl)-3-fluoroprop-2-en-1-yl]-7-[3-(methylsulfonyl)phenyl][1,2,4]triazolo[4,3-a]pyridin-3(2H)-one hydrochloride |

TABLE 1-continued

| Ex No | Structure | Chemical Name* |
|---|---|---|
| 23 | 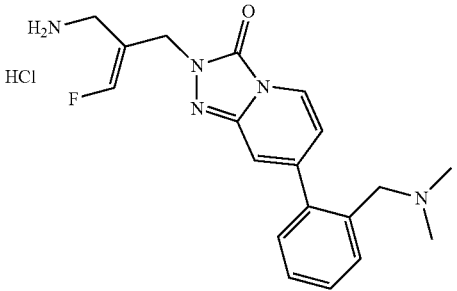 [SMILES: Cl ; CN(C)Cc1ccccc1-c1ccn2c(=O)n(C/C(=C/F)CN)nc2c1] | 2-[(2E)-2-(aminomethyl)-3-fluoroprop-2-en-1-yl]-7-{2-[(dimethylamino)methyl]phenyl}[1,2,4]triazolo[4,3-a]pyridin-3(2H)-one hydrochloride |
| 24 | 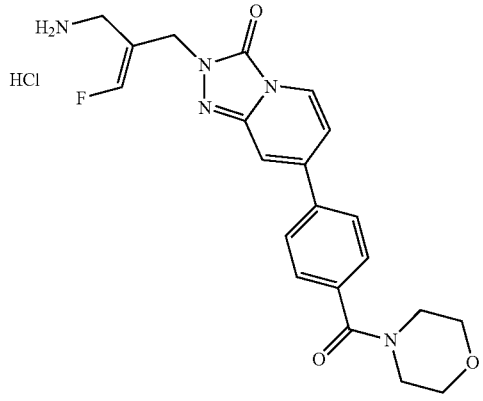 [SMILES: Cl ; NC/C(=C\F)Cn1nc2cc(-c3ccc(C(=O)N4CCOCC4)cc3)ccn2c1=O] | 2-[(2E)-2-(aminomethyl)-3-fluoroprop-2-en-1-yl]-7-[4-(morpholin-4-ylcarbonyl)phenyl][1,2,4]triazolo[4,3-a]pyridin-3(2H)-one hydrochloride |
| 25 | 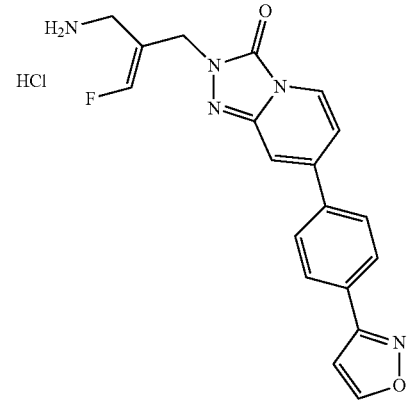 [SMILES: Cl ; NC/C(=C\F)Cn1nc2cc(-c3ccc(-c4ccon4)cc3)ccn2c1=O] | 2-[(2E)-2-(aminomethyl)-3-fluoroprop-2-en-1-yl]-7-[4-(1,2-oxazol-3-yl)phenyl][1,2,4]triazolo[4,3-a]pyridin-3(2H)-one hydrochloride |
| 26 | 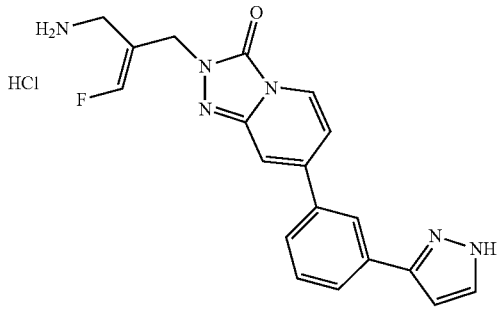 [SMILES: Cl ; NC/C(=C\F)Cn1nc2cc(-c3cccc(-c4cc[nH]n4)c3)ccn2c1=O] | 2-[(2E)-2-(aminomethyl)-3-fluoroprop-2-en-1-yl]-7-[3-(1H-pyrazol-3-yl)phenyl][1,2,4]triazolo[4,3-a]pyridin-3(2H)-one hydrochloride |

TABLE 1-continued
| Ex No | Structure | Chemical Name* |
|---|---|---|
| 27 | 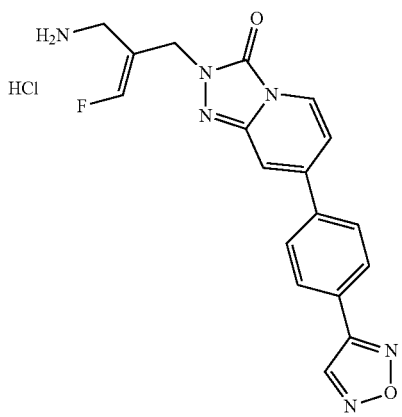 [SMILES: Cl ; NC/C(=C\F)Cn1nc2cc(-c3ccc(-c4cnon4)cc3)ccn2c1=O] | 2-[(2E)-2-(aminomethyl)-3-fluoroprop-2-en-1-yl]-7-[4-(1,2,5-oxadiazol-3-yl)phenyl][1,2,4]triazolo[4,3-a]pyridin-3(2H)-one hydrochloride |
| 28 | 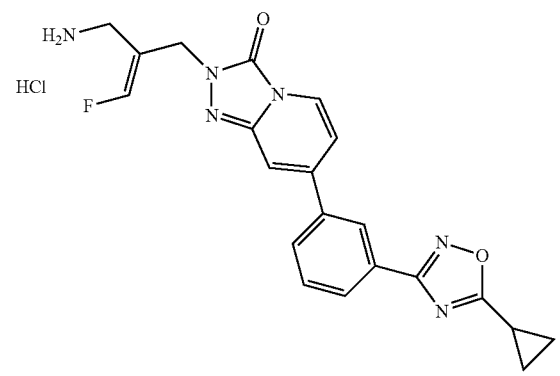 [SMILES: Cl ; NC/C(=C\F)Cn1nc2cc(-c3cccc(-c4noc(C5CC5)n4)c3)ccn2c1=O] | 2-[(2E)-2-(aminomethyl)-3-fluoroprop-2-en-1-yl]-7-[3-(5-cyclopropyl-1,2,4-oxadiazol-3-yl)phenyl][1,2,4]triazolo[4,3-a]pyridin-3(2H)-one hydrochloride |
| 29 | 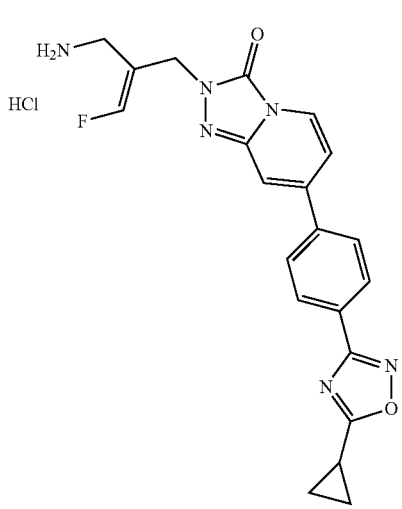 [SMILES: Cl ; NC/C(=C\F)Cn1nc2cc(-c3ccc(-c4noc(C5CC5)n4)cc3)ccn2c1=O] | 2-[(2E)-2-(aminomethyl)-3-fluoroprop-2-en-1-yl]-7-[4-(5-cyclopropyl-1,2,4-oxadiazol-3-yl)phenyl][1,2,4]triazolo[4,3-a]pyridin-3(2H)-one hydrochloride |

TABLE 1-continued

| Ex No | Structure | Chemical Name* |
|---|---|---|
| 30 | 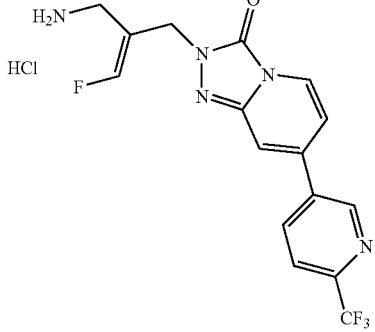 | 2-[(2E)-2-(aminomethyl)-3-fluoroprop-2-en-1-yl]-7-[6-(trifluoromethyl)pyridin-3-yl][1,2,4]triazolo[4,3-a]pyridin-3(2H)-one hydrochloride |
| 31 | 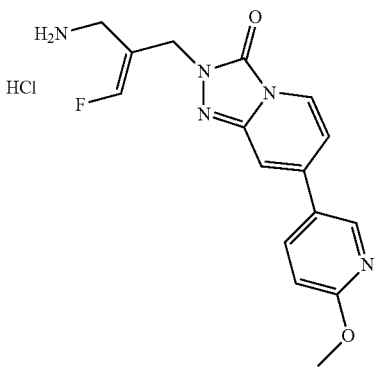 [SMILES: Cl ; COc1ccc(-c2ccn3c(=O)n(C/C(=C/F)CN)nc3c2)cn1] | 2-[(2E)-2-(aminomethyl)-3-fluoroprop-2-en-1-yl]-7-(6-methoxypyridin-3-yl)[1,2,4]triazolo[4,3-a]pyridin-3(2H)-one hydrochloride |
| 32 | 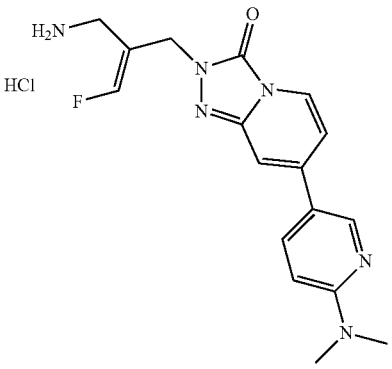 [SMILES: Cl ; CN(C)c1ccc(-c2ccn3c(=O)n(C/C(=C/F)CN)nc3c2)cn1] | 2-[(2E)-2-(aminomethyl)-3-fluoroprop-2-en-1-yl]-7-[6-(dimethylamino)pyridin-3-yl][1,2,4]triazolo[4,3-a]pyridin-3(2H)-one hydrochloride |
| 33 | 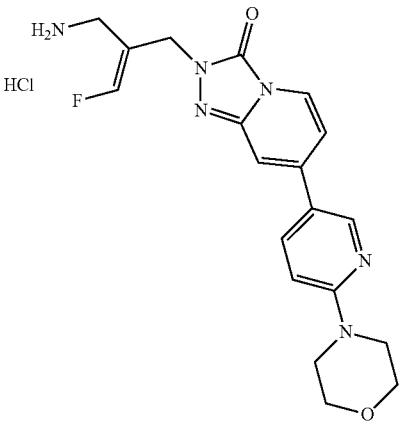 [SMILES: Cl ; NC/C(=C\F)Cn1nc2cc(-c3ccc(N4CCOCC4)nc3)ccn2c1=O] | 2-[(2E)-2-(aminomethyl)-3-fluoroprop-2-en-1-yl]-7-[6-(morpholin-4-yl)pyridin-3-yl][1,2,4]triazolo[4,3-a]pyridin-3(2H)-one hydrochloride |

TABLE 1-continued

| Ex No | Structure | Chemical Name* |
|---|---|---|
| 34 | 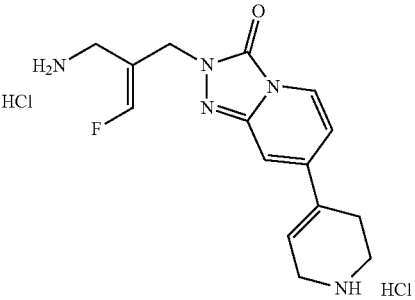 [SMILES: Cl ; NC/C(=C\F)Cn1nc2cc(C3=CCNCC3)ccn2c1=O ; Cl] | 2-[(2E)-2-(aminomethyl)-3-fluoroprop-2-en-1-yl]-7-(1,2,3,6-tetrahydropyridin-4-yl)[1,2,4]triazolo[4,3-a]pyridin-3(2H)-one dihydrochloride |
| 35 | 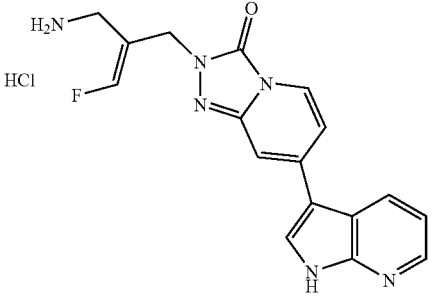 [SMILES: Cl ; NC/C(=C\F)Cn1nc2cc(-c3c[nH]c4ncccc34)ccn2c1=O] | 2-[(2E)-2-(aminomethyl)-3-fluoroprop-2-en-1-yl]-7-(1H-pyrrolo[2,3-b]pyridin-3-yl)[1,2,4]triazolo[4,3-a]pyridin-3(2H)-one hydrochloride |
| 36 | 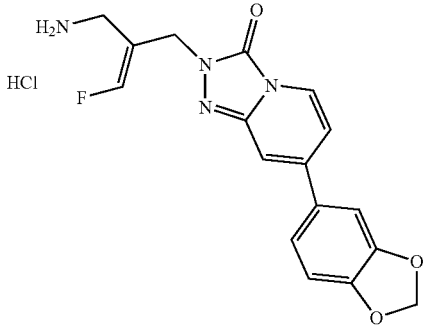 [SMILES: Cl ; NC/C(=C\F)Cn1nc2cc(-c3ccc4c(c3)OCO4)ccn2c1=O] | 2-[(2E)-2-(aminomethyl)-3-fluoroprop-2-en-1-yl]-7-(1,3-benzodioxol-5-yl)[1,2,4]triazolo[4,3-a]pyridin-3(2H)-one hydrochloride |
| 37 | 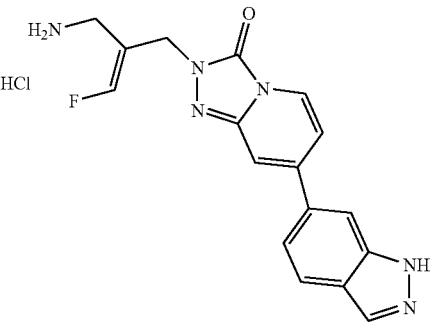 [SMILES: Cl ; NC/C(=C\F)Cn1nc2cc(-c3ccc4cn[nH]c4c3)ccn2c1=O] | 2-[(2E)-2-(aminomethyl)-3-fluoroprop-2-en-1-yl]-7-(1H-indazol-6-yl)[1,2,4]triazolo[4,3-a]pyridin-3(2H)-one hydrochloride |
| 38 | 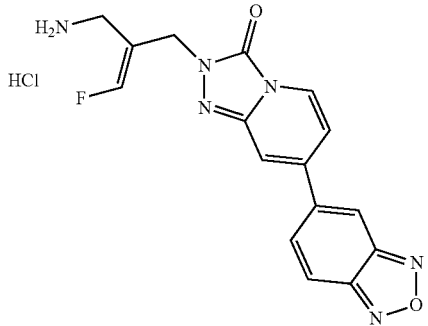 [SMILES: Cl ; NC/C(=C\F)Cn1nc2cc(-c3ccc4nonc4c3)ccn2c1=O] | 2-[(2E)-2-(aminomethyl)-3-fluoroprop-2-en-1-yl]-7-(2,1,3-benzoxadiazol-5-yl)[1,2,4]triazolo[4,3-a]pyridin-3(2H)-one hydrochloride |

TABLE 1-continued

| Ex No | Structure | Chemical Name* |
|---|---|---|
| 39 | 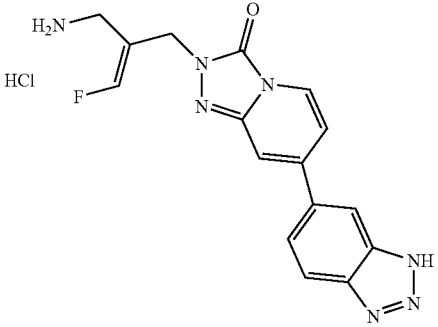 [SMILES: Cl ; NC/C(=C\F)Cn1nc2cc(-c3ccc4nn[nH]c4c3)ccn2c1=O] | 2-[(2E)-2-(aminomethyl)-3-fluoroprop-2-en-1-yl]-7-(1H-benzotriazol-6-yl)[1,2,4]triazolo[4,3-a]pyridin-3(2H)-one hydrochloride |
| 40 | 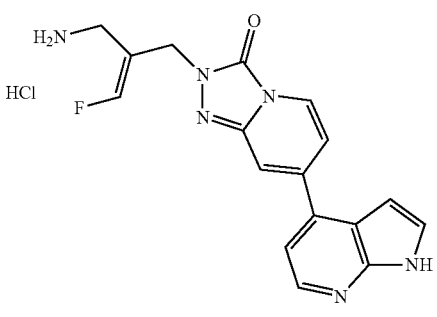 [SMILES: Cl ; NC/C(=C\F)Cn1nc2cc(-c3ccnc4[nH]ccc34)ccn2c1=O] | 2-[(2E)-2-(aminomethyl)-3-fluoroprop-2-en-1-yl]-7-(1H-pyrrolo[2,3-b]pyridin-4-yl)[1,2,4]triazolo[4,3-a]pyridin-3(2H)-one hydrochloride |
| 41 | 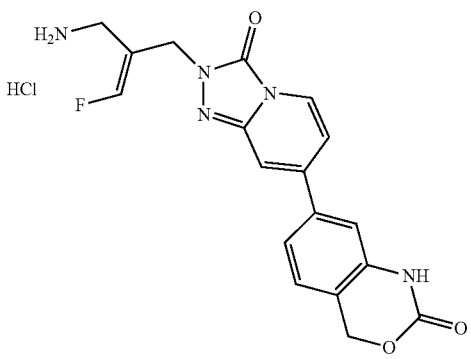 [SMILES: Cl ; NC/C(=C\F)Cn1nc2cc(-c3ccc4c(c3)NC(=O)OC4)ccn2c1=O] | 7-{2-[(2E)-2-(aminomethyl)-3-fluoroprop-2-en-1-yl]-3-oxo-2,3-dihydro[1,2,4]triazolo[4,3-a]pyridin-7-yl}-1,4-dihydro-2H-3,1-benzoxazin-2-one hydrochloride |
| 42 | 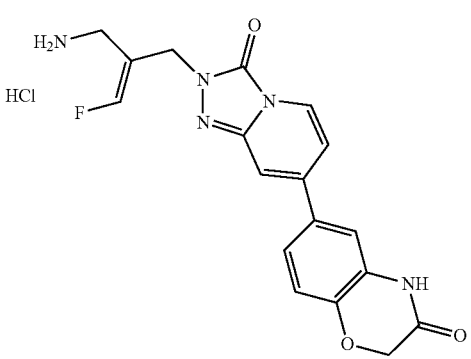 [SMILES: Cl ; NC/C(=C\F)Cn1nc2cc(-c3ccc4c(c3)NC(=O)CO4)ccn2c1=O] | 6-{2-[(2E)-2-(aminomethyl)-3-fluoroprop-2-en-1-yl]-3-oxo-2,3-dihydro[1,2,4]triazolo[4,3-a]pyridin-7-yl}-2H-1,4-benzoxazin-3(4H)-one hydrochloride |

TABLE 1-continued

| Ex No | Structure | Chemical Name* |
|---|---|---|
| 43 | 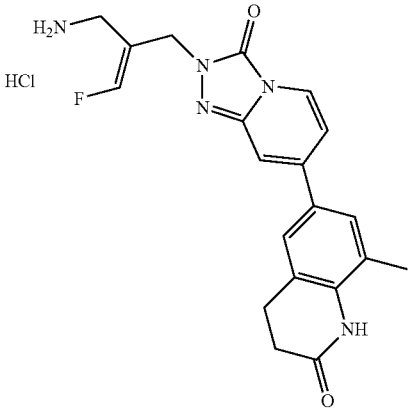 [SMILES: Cl ; Cc1cc(-c2ccn3c(=O)n(C/C(=C/F)CN)nc3c2)cc2c1NC(=O)CC2] | 6-{2-[(2E)-2-(aminomethyl)-3-fluoroprop-2-en-1-yl]-3-oxo-2,3-dihydro[1,2,4]triazolo[4,3-a]pyridin-7-yl}-8-methyl-3,4-dihydroquinolin-2(1H)-one hydrochloride |
| 44 | 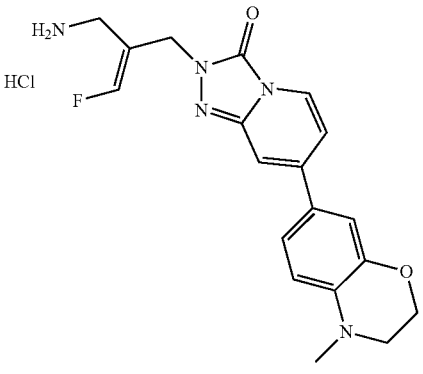 [SMILES: Cl ; CN1CCOc2cc(-c3ccn4c(=O)n(C/C(=C/F)CN)nc4c3)ccc21] | 2-[(2E)-2-(aminomethyl)-3-fluoroprop-2-en-1-yl]-7-(4-methyl-3,4-dihydro-2H-1,4-benzoxazin-7-yl)[1,2,4]triazolo[4,3-a]pyridin-3(2H)-one hydrochloride |
| 45 | 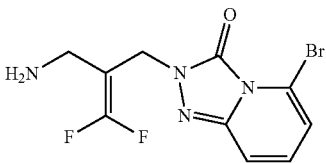 | 2-[2-(aminomethyl)-3,3-difluoro-allyl]-5-bromo-[1,2,4]triazolo[4,3-a]pyridin-3-one |
| 46 | 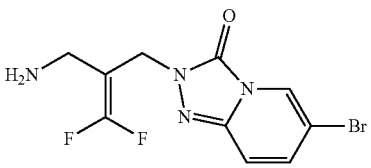 [SMILES: NCC(Cn1nc2ccc(Br)cn2c1=O)=C(F)F] | 2-[2-(aminomethyl)-3,3-difluoro-allyl]-6-bromo-[1,2,4]triazolo[4,3-a]pyridin-3-one |
| 47 | 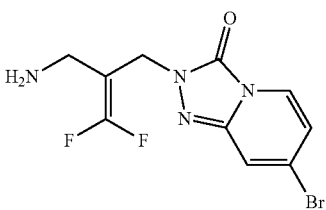 [SMILES: NCC(Cn1nc2cc(Br)ccn2c1=O)=C(F)F] | 2-[2-(aminomethyl)-3,3-difluoro-allyl]-7-bromo-[1,2,4]triazolo[4,3-a]pyridin-3-one |

TABLE 1-continued

| Ex No | Structure | Chemical Name* |
|---|---|---|
| 48 | 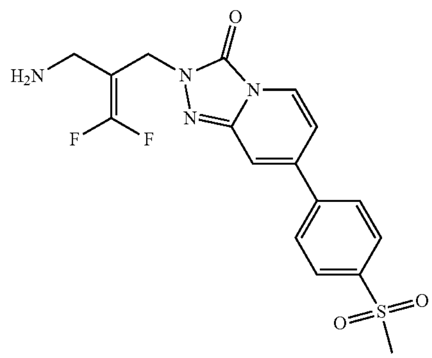 [SMILES: CS(=O)(=O)c1ccc(-c2ccn3c(=O)n(CC(CN)=C(F)F)nc3c2)cc1] | 2-[2-(aminomethyl)-3,3-difluoro-allyl]-7-(4-methylsulfonylphenyl)-[1,2,4]triazolo[4,3-a]pyridin-3-one |
| 49 | 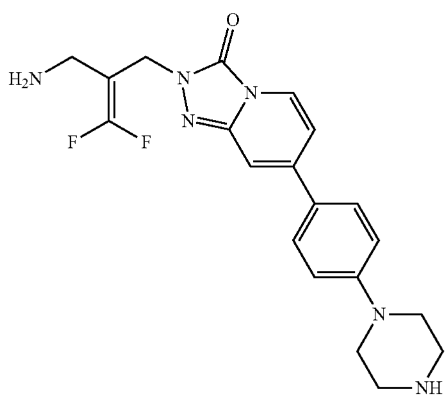 [SMILES: NCC(Cn1nc2cc(-c3ccc(N4CCNCC4)cc3)ccn2c1=O)=C(F)F] | 2-[2-(aminomethyl)-3,3-difluoro-allyl]-7-(4-piperazin-1-ylphenyl)-[1,2,4]triazolo[4,3-a]pyridin-3-one |
| 50 | 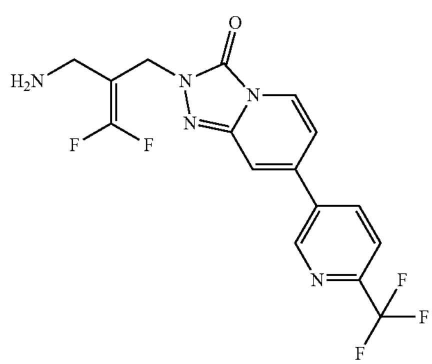 [SMILES: NCC(Cn1nc2cc(-c3ccc(C(F)(F)F)nc3)ccn2c1=O)=C(F)F] | 2-[2-(aminomethyl)-3,3-difluoro-allyl]-7-[6-(trifluoromethyl)-3-pyridyl]-[1,2,4]triazolo[4,3-a]pyridin-3-one |
| 51 | 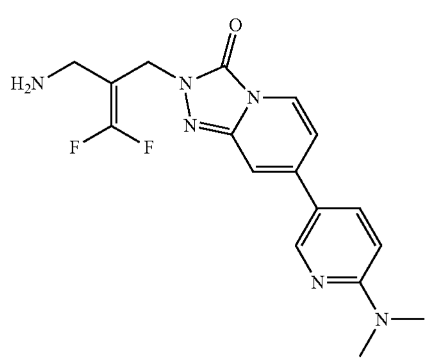 [SMILES: CN(C)c1ccc(-c2ccn3c(=O)n(CC(CN)=C(F)F)nc3c2)cn1] | 2-[2-(aminomethyl)-3,3-difluoro-allyl]-7-[6-(dimethylamino)-3-pyridyl]-[1,2,4]triazolo[4,3-a]pyridin-3-one |

TABLE 1-continued

| Ex No | Structure | Chemical Name* |
|---|---|---|
| 52 | 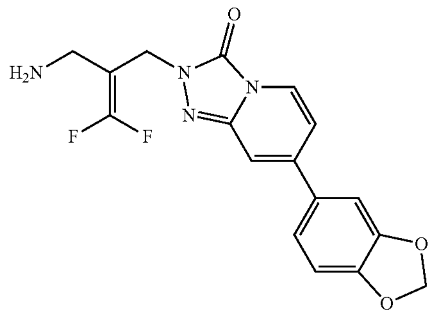 [SMILES: NCC(Cn1nc2cc(-c3ccc4c(c3)OCO4)ccn2c1=O)=C(F)F] | 2-[2-(aminomethyl)-3,3-difluoro-allyl]-7-(1,3-benzodioxol-5-yl)-[1,2,4]triazolo[4,3-a]pyridin-3-one |
| 53 | 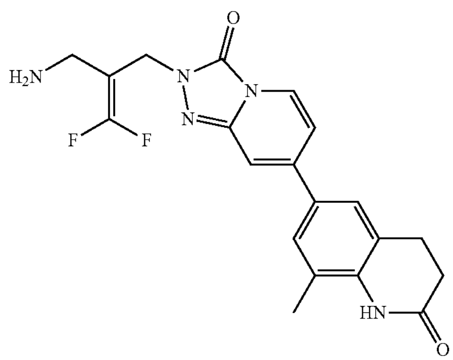 [SMILES: Cc1cc(-c2ccn3c(=O)n(CC(CN)=C(F)F)nc3c2)cc2c1NC(=O)CC2] | 6-[2-[2-(aminomethyl)-3,3-difluoro-allyl]-3-oxo-[1,2,4]triazolo[4,3-a]pyridin-7-yl]-8-methyl-3,4-dihydro-1H-quinolin-2-one |
| 54 | 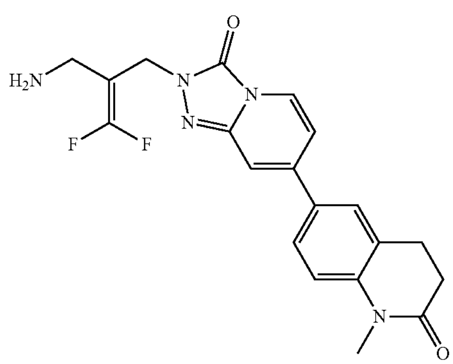 [SMILES: CN1C(=O)CCc2cc(-c3ccn4c(=O)n(CC(CN)=C(F)F)nc4c3)ccc21] | 6-[2-[2-(aminomethyl)-3,3-difluoro-allyl]-3-oxo-[1,2,4]triazolo[4,3-a]pyridin-7-yl]-1-methyl-3,4-dihydroquinolin-2-one |
| 55 | 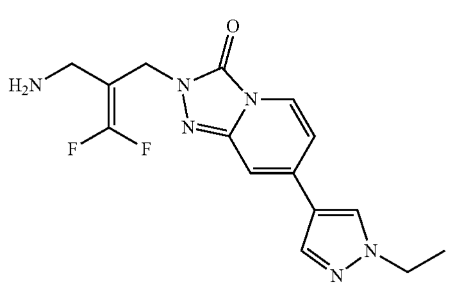 [SMILES: CCn1cc(-c2ccn3c(=O)n(CC(CN)=C(F)F)nc3c2)cn1] | 2-[2-(aminomethyl)-3,3-difluoro-allyl]-7-(1-ethyl-pyrazol-4-yl)-[1,2,4]triazolo[4,3-a]pyridin-3-one |

TABLE 1-continued

| Ex No | Structure | Chemical Name* |
|---|---|---|
| 56 | 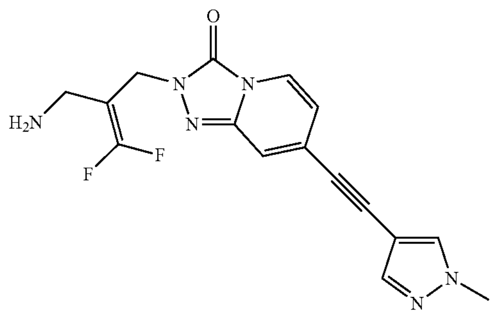 [SMILES: Cn1cc(C#Cc2ccn3c(=O)n(CC(CN)=C(F)F)nc3c2)cn1] | 2-[2-(aminomethyl)-3,3-difluoro-allyl]-7-[2-(1-methylpyrazol-4-yl)ethynyl]-[1,2,4]triazolo[4,3-a]pyridin-3-one |
| 57 | 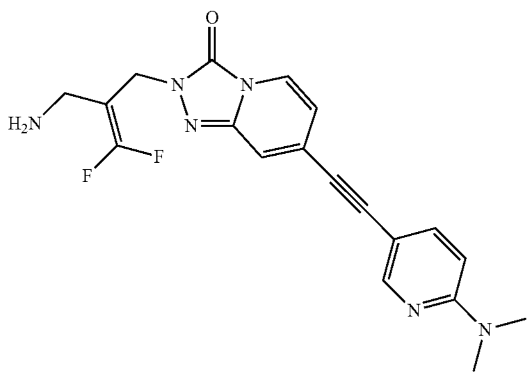 [SMILES: CN(C)c1ccc(C#Cc2ccn3c(=O)n(CC(CN)=C(F)F)nc3c2)cn1] | 2-[2-(aminomethyl)-3,3-difluoro-allyl]-7-[2-[6-(dimethylamino)-3-pyridyl]ethynyl]-[1,2,4]triazolo[4,3-a]pyridin-3-one |
| 58 | 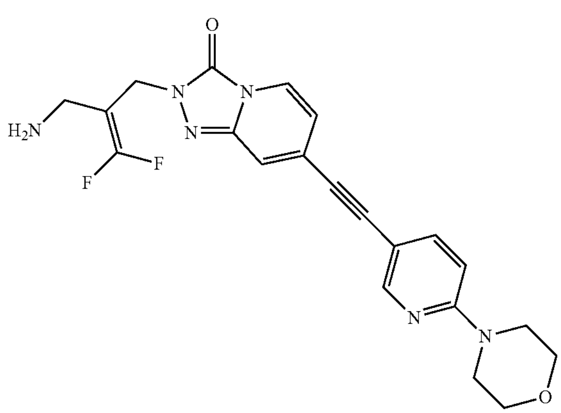 [SMILES: NCC(Cn1nc2cc(C#Cc3ccc(N4CCOCC4)nc3)ccn2c1=O)=C(F)F] | 2-[2-(aminomethyl)-3,3-difluoro-allyl]-7-[2-(6-morpholino-3-pyridyl)ethynyl]-[1,2,4]triazolo[4,3-a]pyridin-3-one |
| 59 | 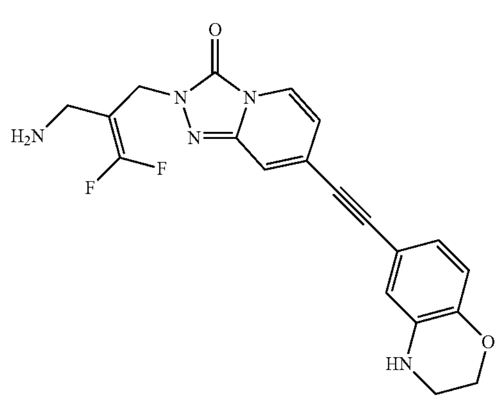 [SMILES: NCC(Cn1nc2cc(C#Cc3ccc4c(c3)NCCO4)ccn2c1=O)=C(F)F] | 2-[2-(aminomethyl)-3,3-difluoro-allyl]-7-[2-(3,4-dihydro-2H-1,4-benz-oxazin-6-yl)ethynyl]-[1,2,4]triazolo[4,3-a]pyridin-3-one |

TABLE 1-continued

| Ex No | Structure | Chemical Name* |
|---|---|---|
| 60 | 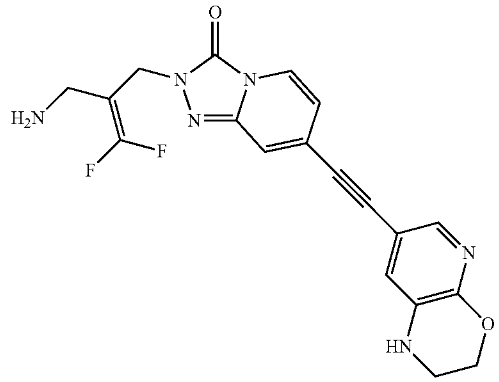 [SMILES: NCC(Cn1nc2cc(C#Cc3cnc4c(c3)NCCO4)ccn2c1=O)=C(F)F] | 2-[2-(aminomethyl)-3,3-difluoro-allyl]-7-[2-(2,3-dihydro-1H-pyrido[2,3-b][1,4]oxazin-7-yl)ethynyl]-[1,2,4]triazolo[4,3-a]pyridin-3-one |
| 61 | 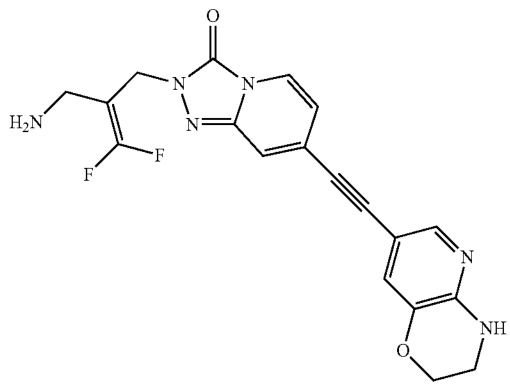 [SMILES: NCC(Cn1nc2cc(C#Cc3cnc4c(c3)OCCN4)ccn2c1=O)=C(F)F] | 2-[2-(aminomethyl)-3,3-difluoro-allyl]-7-[2-(3,4-dihydro-2H-pyrido[3,2-b][1,4]oxazin-7-yl)ethynyl]-[1,2,4]triazolo[4,3-a]pyridin-3-one |
| 62 | 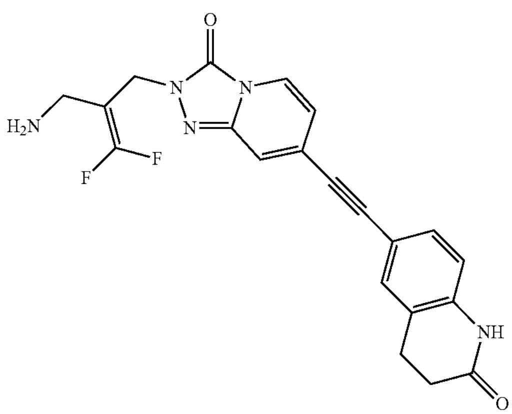 [SMILES: NCC(Cn1nc2cc(C#Cc3ccc4c(c3)CCC(=O)N4)ccn2c1=O)=C(F)F] | 6-[2-[2-[2-(aminomethyl)-3,3-difluoro-allyl]-3-oxo-[1,2,4]triazolo[4,3-a]pyridin-7-yl]ethynyl]-3,4-dihydro-1H-quinolin-2-one |
| 63 | 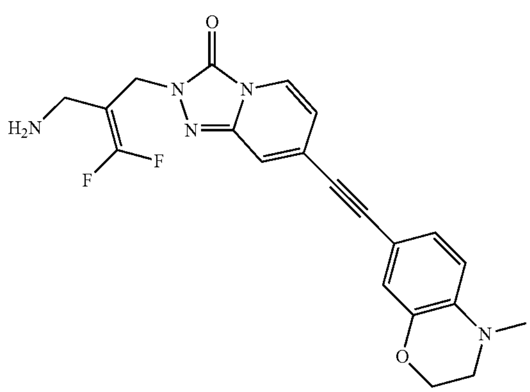 [SMILES: CN1CCOc2cc(C#Cc3ccn4c(=O)n(CC(CN)=C(F)F)nc4c3)ccc21] | 2-[2-(aminomethyl)-3,3-difluoro-allyl]-7-[2-(4-methyl-2,3-dihydro-1,4-benzoxazin-7-yl)ethynyl]-[1,2,4]triazolo[4,3-a]pyridin-3-one |

*Compounds were isolated as either free bases or salts as described in Examples 1-63.

Experimental Example 1: Activity Evaluation with Respect to Amine Oxidases

The compounds according to the present technology were evaluated in terms of activity on recombinant human VAP-1 (R&D systems) by measuring the level of hydrogen peroxide in horseradish peroxidase (HRP)-coupled reaction using Amplex Red Hydrogen Peroxide Assay Kit (Molecular Probes, Invitrogen, USA). The experiment was carried out at room temperature using benzylamine as a substrate. In the HRP-coupled reaction, hydrogen peroxide oxidation of 10-acetyl-3,7-dihydroxyphenoxazine (Amplex Red reagent) produces resorufin, which is a highly fluorescent compound. Briefly, the test compound was dissolved in dimethyl sulfoxide (DMSO) at a concentration of 20 mM. The dose-response assessment was made by 1:3 serial dilution in DMSO, thereby creating a 8 point curve. The concentration of the upper part was controlled according to the efficacy of the compounds, followed by dilution with a reaction buffer solution to obtain a final DMSO concentration of less than 1%. To each well of a 96 black well plate, human VAP-1 purified in 50 mM sodium phosphate buffer solution (pH7.4) was added. The test compounds dissolved in DMSO were incubated with the human VAP-1 enzymes at 37° C. for 30 minutes. After 30-minute incubation, each well was added with a reaction mixture containing 200 uM Amplex Red reagent prepared from 50 mM sodium phosphate buffer solution (pH 7.4), 1 mM benzylamine, and 1 U/mL HRP. Fluorescence intensity was measured at several time points during 1-2 hours using a microplate reader (Flexstation3, Molecular Devices) under the wavelength condition exciting at 544 nm and reading the emission at 590 nm. The inhibitory effect of the compounds was measured as a decrease (%) in the signal rate as compared to the control group without any inhibitor (only diluted DMSO). Data was fixed to a logistic model with four variables and $IC_{50}$ value was calculated using GraphPad Prism program.

In addition, the compounds according to the present technology were evaluated in terms of activity on a recombinant human MAO-A (monoamine oxidase-A, Sigma-Aldrich) and a recombinant human MAO-B (monoamine oxidase-B, Sigma-Aldrich) by using as substrates, 0.5 mM tyramine and 1 mM benzylamine, respectively, with a method similar to the activity evaluation method for recombinant human VAP-1. The compounds according to the present technology were also evaluated in terms of activity on a recombinant human DAO (diamine oxidase, R&D systems) by using as a substrate 1 mM putrescine with a method similar to the activity evaluation method for recombinant human VAP-1.

The results obtained by evaluating the activity against the enzymes as above are shown in Table 2 below.

TABLE 2

| | Inhibitory Activity ($IC_{50}$, nM) | | | |
|---|---|---|---|---|
| Example | human VAP-1 | MAO-A | MAO-B | DAO |
| 1 | 87 | | | 100 |
| 2 | 6.2 | 68,400 | 1,780 | <100 |
| 3 | 3.6 | >100,000 | 231 | <100 |
| 4 | 6.2 | >100,000 | >10,000 | <100 |
| 5 | 2.0 | >100,000 | 1,450 | <100 |
| 6 | 2.1 | >100,000 | 73 | <100 |
| 7 | 2.3 | >100,000 | 25 | 0.2 |
| 8 | 14 | | | <100 |
| 9 | 12 | >100,000 | 37 | 0.2 |
| 10 | 6.6 | >100,000 | 64 | <100 |

TABLE 2-continued

| | Inhibitory Activity ($IC_{50}$, nM) | | | |
|---|---|---|---|---|
| Example | human VAP-1 | MAO-A | MAO-B | DAO |
| 11 | 3.7 | >100,000 | 39 | 0.2 |
| 12 | 3.4 | 14,000 | <10 | 1.1 |
| 13 | 4.8 | >100,000 | 15 | <100 |
| 14 | 6.2 | >100,000 | 69 | <100 |
| 15 | 9.3 | >100,000 | 597 | <100 |
| 16 | 4.5 | 10,200 | 52 | <100 |
| 17 | 0.6 | >100,000 | 290 | 0.3 |
| 18 | 90 | | | NA |
| 19 | 38 | | | NA |
| 20 | >100 | | | NA |
| 21 | 150 | | | NA |
| 22 | 0.7 | >100,000 | 180 | 12 |
| 23 | 7.0 | >10,000 | >10,000 | 37 |
| 24 | 0.6 | >100,000 | >10,000 | 14 |
| 25 | 0.2 | 18,000 | 220 | 9.1 |
| 26 | 0.2 | >100,000 | <10 | 1.9 |
| 27 | 0.6 | 1,450 | 67 | 1.8 |
| 28 | 0.5 | >100,000 | 290 | 5 |
| 29 | 0.4 | 44,000 | 380 | 4 |
| 30 | 0.3 | 68,000 | 8.4 | 1.1 |
| 31 | 0.3 | >100,000 | 61 | 5 |
| 32 | 0.4 | >100,000 | 19 | 24 |
| 33 | 0.4 | | 130 | 5.8 |
| 34 | 2 | >100,000 | >100,000 | 1 |
| 35 | 0.2 | >100,000 | 24 | 0.5 |
| 36 | 0.3 | 66,000 | 3.8 | 20 |
| 37 | 0.1 | 26,000 | 190 | 0.3 |
| 38 | 0.2 | 3,500 | <10 | 0.4 |
| 39 | 0.1 | 96,000 | 1,100 | 0.2 |
| 40 | 0.3 | >100,000 | 760 | 9.4 |
| 41 | 0.3 | 6,800 | 730 | 1.3 |
| 42 | 0.3 | 5,400 | 1,400 | 1 |
| 43 | 0.5 | >100,000 | 140 | 9.6 |
| 44 | 1 | >100,000 | <10 | 400 |
| 45 | 24 | >100,000 | >100,000 | 11,000 |
| 46 | 36 | >100,000 | >100,000 | 26,000 |
| 47 | 7.0 | >100,000 | >100,000 | 42,000 |
| 48 | 0.1 | >100,000 | 800 | 100 |
| 49 | 1.6 | >100,000 | 53,000 | 390 |
| 50 | 0.2 | >100,000 | 100 | 3 |
| 51 | 0.4 | >100,000 | 150 | 17 |
| 52 | 0.3 | >100,000 | 37 | 160 |
| 53 | 0.2 | >100,000 | 320 | 12 |
| 54 | 0.1 | >100,000 | 170 | 22 |
| 55 | 0.4 | >100,000 | 5,100 | 1,800 |
| 56 | 1 | >100,000 | 2500 | 6300 |
| 57 | 0.3 | >100,000 | 6,200 | 120 |
| 58 | 0.3 | >100,000 | 5300 | 34 |
| 59 | 1.8 | >100,000 | 2700 | 9000 |
| 60 | 0.4 | >100,000 | >100,000 | 220 |
| 61 | 0.6 | >100,000 | 37000 | 220 |
| 62 | 0.2 | >100,000 | 14000 | 150 |
| 63 | 2.2 | >100,000 | >100,000 | 320 |

From the results of Table 2 above, it can be seen that the compounds according to the present technology have excellent inhibitory activity on VAP-1 among various amine oxidases.

Para. A. A compound of Formula X

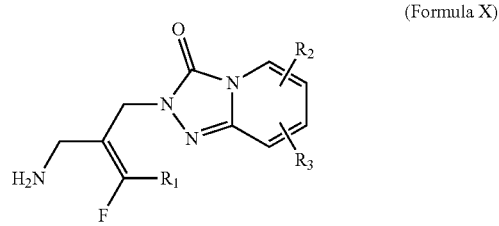

(Formula X)

or a stereoisomer thereof or a pharmaceutically acceptable salt thereof;

wherein $R_1$ is hydrogen or fluoro; and $R_2$ and $R_3$, each independently, are selected from the group consisting of hydrogen, halogen, $C_{1-6}$ alkyl, —R, and —C≡C—R;

wherein said R is substituted or unsubstituted cyclic ring, optionally containing 1 to 5 heteroatom ring members chosen from O, N, or S, and the cyclic ring is aromatic or non-aromatic.

Para. B. The compound or a stereoisomer thereof or a pharmaceutically acceptable salt thereof of Para. A, wherein R is substituted or unsubstituted aryl.

Para. C. The compound or a stereoisomer thereof or a pharmaceutically acceptable salt thereof of Para. A, wherein R is substituted or unsubstituted phenyl.

Para. D. The compound or a stereoisomer thereof or a pharmaceutically acceptable salt thereof of Para. A, wherein R is substituted or unsubstituted heteroaryl.

Para. E. The compound or a stereoisomer thereof or a pharmaceutically acceptable salt thereof of Para. A, wherein R is substituted or unsubstituted non-aromatic heterocyclic.

Para. F. The compound or a stereoisomer thereof or a pharmaceutically acceptable salt thereof of Para. A, wherein the substituted or unsubstituted cyclic ring is selected from the group consisting of substituted or unsubstituted benzene, substituted or unsubstituted pyridine, substituted or unsubstituted tetrahydropyridine, substituted or unsubstituted pyrazole, substituted or unsubstituted benzodioxole, substituted or unsubstituted 2,3-dihydro benzodioxine, substituted or unsubstituted benzothiazole, substituted or unsubstituted benzoxadiazole, substituted or unsubstituted benzotriazole, substituted or unsubstituted indazole, substituted or unsubstituted pyrrolo[2,3-b]pyridine, substituted or unsubstituted 3,4-dihydroquinolin-2-one, substituted or unsubstituted 3,4-dihydro-1,4-benzoxazine, substituted or unsubstituted 1,4-benzoxazin-3-one, substituted or unsubstituted 1,3-dihydro-3,1-benzoxazin-2-one, substituted or unsubstituted 2,3-dihydro-pyrido[2,3-b][1,4]oxazine, substituted or unsubstituted pyrido[2,3-b][1,4]oxazin-2-one, substituted or unsubstituted 3,4-dihydro-pyrido[3,2-b][1,4]oxazine, and substituted or unsubstituted pyrido[3,2-b][1,4]oxazin-3-one.

Para. G. A compound of Formula 1

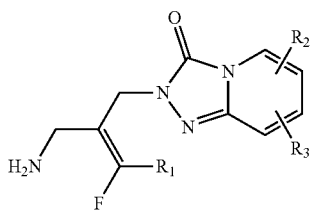

(Formula 1)

or a stereoisomer thereof or a pharmaceutically acceptable salt thereof;

wherein $R_1$ is hydrogen or fluoro, and $R_2$ and $R_3$, each independently, are selected from the group consisting of hydrogen, halogen, $C_{1-6}$ alkyl, —R, and —C≡C—R, wherein $R_2$ and $R_3$ cannot be simultaneously hydrogen, halogen, $C_{1-6}$ alkyl, —R, or —C≡C—R, wherein said R is a cyclic ring selected from the group consisting of benzene, pyridine, tetrahydropyridine, pyrazole, benzodioxole, 2,3-dihydrobenzodioxine, benzothiazole, benzoxadiazole, benzotriazole, indazole, pyrrolo[2,3-b]pyridine, 3,4-dihydroquinolin-2-one, 3,4-dihydro-1,4-benzoxazine, 1,4-benzoxazin-3-one, 1,3-dihydro-3,1-benzoxazin-2-one, 2,3-dihydro-pyrido[2,3-b][1,4]oxazine, pyrido[2,3-b][1,4]oxazin-2-one, 3,4-dihydro-pyrido[3,2-b][1,4]oxazine, and pyrido[3,2-b][1,4]oxazin-3-one, wherein said cyclic ring is optionally substituted with a substituent selected from the group consisting of $C_{1-6}$ alkyl, trifluoromethyl, $C_{1-6}$ alkoxy, amino, mono- or di-$C_{1-6}$ alkylamino, di-$C_{1-6}$ alkylaminomethyl, $C_{1-6}$ alkylcarbonylamino, $C_{1-6}$ alkylsulfonyl, morpholinylsulfonyl, morpholinylcarbonyl, piperazinyl, morpholinyl, triazolyl, pyrazolyl, oxazolyl, oxadiazolyl, and cyclopropyl-oxadiazolyl.

Para. H. The compound or a stereoisomer thereof or a pharmaceutically acceptable salt thereof of any one of Paras. A-G, wherein said $R_1$ is fluoro.

Para. I. The compound or a stereoisomer thereof or a pharmaceutically acceptable salt thereof of any one of Paras. A-G, wherein said $R_1$ is hydrogen.

Para. J. The compound or a stereoisomer thereof or a pharmaceutically acceptable salt thereof of any one of Paras. A-I, wherein said $R_2$ is hydrogen and $R_3$ is halogen, —R, or —C≡C—R.

Para. K. The compound or a pharmaceutically acceptable salt thereof of any one of Paras. A-I, wherein said $R_2$ is hydrogen and $R_3$ is halogen or —R.

Para. L. The compound or a stereoisomer thereof or a pharmaceutically acceptable salt thereof of any one of Paras. A-I, wherein said $R_2$ is hydrogen and $R_3$ is halogen or —C≡C—R.

Para. M. The compound or a stereoisomer thereof or a pharmaceutically acceptable salt thereof of any one of Paras. A-I, wherein said $R_2$ is hydrogen and $R_3$ is —R.

Para. N. The compound or a stereoisomer thereof or a pharmaceutically acceptable salt thereof of any one of Paras. A-I, wherein said $R_2$ is hydrogen and $R_3$ is —C≡C—R.

Para. O. The compound or a stereoisomer thereof or a pharmaceutically acceptable salt thereof, of Para. A or Para. G, wherein said R is a cyclic ring selected from the group consisting of benzene and pyrazole.

Para. P. The compound or a stereoisomer thereof or a pharmaceutically acceptable salt thereof of Para. O, wherein said cyclic ring is substituted with a substituent selected from the group consisting of $C_{1-6}$ alkyl, $C_{1-6}$ alkylsulfonyl, and piperazinyl.

Para. Q. The compound or a stereoisomer thereof or a pharmaceutically acceptable salt thereof of Para. A or Para. G, wherein $R_1$ is fluoro, $R_2$ is hydrogen, $R_3$ is halogen or —R, wherein said R is a cyclic ring selected from the group consisting of benzene and pyrazole, wherein said cyclic ring is substituted with a substituent selected from the group consisting of $C_{1-6}$ alkyl, $C_{1-6}$ alkylsulfonyl, and piperazinyl.

Para. R. A compound of Formula 11

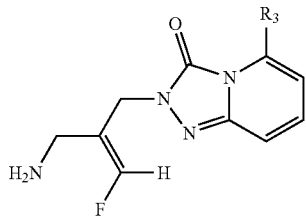

(Formula 11)

or a stereoisomer thereof or a pharmaceutically acceptable salt thereof;

wherein $R_3$ is substituted or unsubstituted aryl, or substituted or unsubstituted heteroaryl.

Para. S. The compound or a stereoisomer thereof or a pharmaceutically acceptable salt thereof of Para. R, wherein $R_3$ is substituted aryl.

Para. T. The compound or a stereoisomer thereof or a pharmaceutically acceptable salt thereof of Para. S, wherein $R_3$ is substituted phenyl.

Para. U. The compound or a stereoisomer thereof or a pharmaceutically acceptable salt thereof of Para. S, wherein $R_3$ is substituted or unsubstituted benzodioxole, substituted or unsubstituted benzoxadiazole, or phenyl, wherein the phenyl is substituted with $C_{1-6}$ alkylcarbonylamino or oxazolyl.

Para. V. A compound of Formula 12

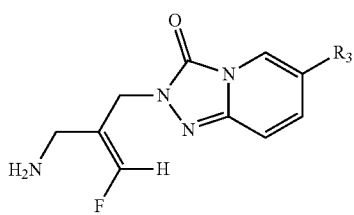

(Formula 12)

or a stereoisomer thereof or a pharmaceutically acceptable salt thereof;

wherein $R_3$ is substituted or unsubstituted aryl, or substituted or unsubstituted heteroaryl.

Para. W. The compound or a stereoisomer thereof or a pharmaceutically acceptable salt thereof of Para. V, wherein $R_3$ is substituted or unsubstituted benzodioxole, substituted or unsubstituted 2,3-dihydrobenzodioxine, substituted or unsubstituted 3,4-dihydroquinolin-2-one, substituted or unsubstituted benzothiazole, substituted or unsubstituted benzoxadiazole, substituted benzene, or substituted pyridine.

Para. X. The compound or a stereoisomer thereof or a pharmaceutically acceptable salt thereof of Para. W, wherein the benzene or the pyridine is substituted with trifluoromethyl, amino, $C_{1-6}$ alkylcarbonylamino, $C_{1-6}$ alkylsulfonyl, morpholinylsulfonyl, morpholinyl, triazolyl, and oxazolyl.

Para. Y A compound of Formula 13

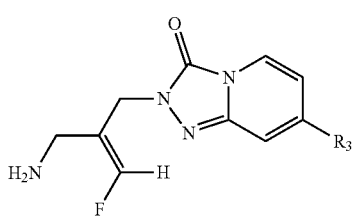

(Formula 13)

or a stereoisomer thereof or a pharmaceutically acceptable salt thereof;

wherein $R_3$ is substituted or unsubstituted aryl, or a substituted or unsubstituted cyclic ring.

Para. Z. The compound or a stereoisomer thereof or a pharmaceutically acceptable salt thereof of Para. Y, wherein $R_3$ is substituted or unsubstituted aryl.

Para. AA. The compound or a stereoisomer thereof or a pharmaceutically acceptable salt thereof of Para. Z, wherein $R_3$ is substituted or unsubstituted benzoxadiazole, substituted or unsubstituted 3,4-dihydroquinolin-2-one, substituted or unsubstituted benzodioxole, substituted or unsubstituted indazole, substituted or unsubstituted pyrazole, substituted or unsubstituted benzotriazole, substituted or unsubstituted 1,3-dihydro-3,1-benzoxazin-2-one, substituted or unsubstituted 1,4-benzoxazin-3-one, substituted or unsubstituted 3,4-dihydro-1,4-benzoxazine, or substituted phenyl.

Para. AB. The compound or a stereoisomer thereof or a pharmaceutically acceptable salt thereof of Para. AA, wherein $R_3$ is phenyl substituted with di-$C_{1-6}$ alkylaminomethyl, $C_{1-6}$ alkylsulfonyl, morpholinylcarbonyl, pyrazolyl, oxazolyl, oxadiazolyl, piperazinyl, and cyclopropyl-oxadiazolyl Para. AC. The compound or a stereoisomer thereof or a pharmaceutically acceptable salt thereof of Para. Y, wherein $R_3$ is a substituted or unsubstituted heterocyclic group.

Para. AD. The compound or a stereoisomer thereof or a pharmaceutically acceptable salt thereof of Para. AC, wherein $R_3$ is tetrahydropyridine.

Para. AE. The compound or a stereoisomer thereof or a pharmaceutically acceptable salt thereof of Para. AC, wherein $R_3$ is substituted or unsubstituted heteroaryl.

Para. AF. The compound or a stereoisomer thereof or a pharmaceutically acceptable salt thereof of Para. AE, wherein $R_3$ is pyrrolo[2,3-b]pyridine or substituted pyridine.

Para. AG. The compound or a stereoisomer thereof or a pharmaceutically acceptable salt thereof of Para. AF, wherein $R_3$ is a pyridine substituted with trifluoromethyl, $C_{1-6}$ alkoxy, mono- or di-$C_{1-6}$ alkylamino, or morpholinyl.

Para. AH. The compound or a stereoisomer thereof or a pharmaceutically acceptable salt thereof of Para. Y, wherein $R_3$ is a cyclic ring selected from the group consisting of benzene, pyridine, benzoxadiazole, 3,4-dihydroquinolin-2-one, benzodioxole, indazole, benzotriazole, 1,3-dihydro-3,1-benzoxazin-2-one, 1,4-benzoxazin-3-one, 3,4-dihydro-1,4-benzoxazine, or pyrrolo[2,3-b]pyridine;

wherein said cyclic ring is optionally substituted with a substituent selected from the group consisting of $C_{1-6}$ alkyl, trifluoromethyl, $C_{1-6}$ alkoxy, mono- or di-$C_{1-6}$ alkylamino, di-$C_{1-6}$ alkylaminomethyl, $C_{1-6}$ alkylsulfonyl, morpholinylcarbonyl, morpholinyl, pyrazolyl, oxazolyl, oxadiazolyl, and cyclopropyl-oxadiazolyl.

Para. AI. A compound of Formula 14

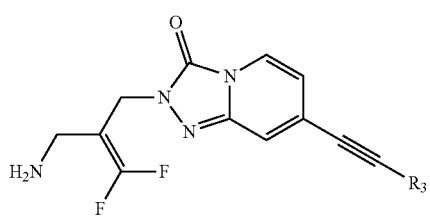

(Formula 14)

or a stereoisomer thereof or a pharmaceutically acceptable salt thereof;
wherein
$R_3$ is substituted or unsubstituted aryl, or substituted or unsubstituted heteroaryl.

Para. AJ. The compound or a stereoisomer thereof or a pharmaceutically acceptable salt thereof of Para. AI, wherein $R_3$ is substituted aryl.

Para. AK. The compound or a stereoisomer thereof or a pharmaceutically acceptable salt thereof of Para. AJ, wherein $R_3$ is substituted or unsubstituted 3,4-dihydroquinolin-2-one, or substituted or unsubstituted 3,4-dihydro-1,4-benzoxazine.

Para. AL. The compound or a stereoisomer thereof or a pharmaceutically acceptable salt thereof of Para. AI, wherein $R_3$ is substituted or unsubstituted heteroaryl.

Para. AM. The compound or a stereoisomer thereof or a pharmaceutically acceptable salt thereof of Para. AL, wherein $R_3$ is substituted pyrazole, substituted pyridine, substituted or unsubstituted 2,3-dihydro-pyrido[2,3-b][1,4]oxazine, or substituted or unsubstituted 3,4-dihydro-pyrido[3,2-b][1,4]oxazine.

Para. AN. The compound or a stereoisomer thereof or a pharmaceutically acceptable salt thereof of Para. AM, wherein $R_3$ is pyridine substituted with mono- or di-$C_{1-6}$ alkylamino or morpholinyl.

Para. AO. The compound or a stereoisomer thereof or a pharmaceutically acceptable salt thereof of Para. A or Para. G, which is selected from the group consisting of:

2-[(2E)-2-(aminomethyl)-3-fluoroprop-2-en-1-yl]-6-bromo[1,2,4]triazolo[4,3-a]pyridin-3(2H)-one;
N-[4-[2-[(2E)-2-(aminomethyl)-3-fluoroprop-2-en-1-yl]-3-oxo-2,3-dihydro[1,2,4]triazolo[4,3-a]pyridin-6-yl]phenyl]acetamide;
2-[(2E)-2-(aminomethyl)-3-fluoroprop-2-en-1-yl]-6-[4-(methylsulfonyl)phenyl][1,2,4]triazolo[4,3-a]pyridin-3(2H)-one;
2-[(2E)-2-(aminomethyl)-3-fluoroprop-2-en-1-yl]-6-[4-(morpholin-4-ylsulfonyl)phenyl][1,2,4]triazolo[4,3-a]pyridin-3(2H)-one;
2-[(2E)-2-(aminomethyl)-3-fluoroprop-2-en-1-yl]-6-[4-(1H-1,2,4-triazol-3-yl)phenyl][1,2,4]triazolo[4,3-a]pyridin-3(2H)-one;
2-[(2E)-2-(aminomethyl)-3-fluoroprop-2-en-1-yl]-6-[3-(1H-1,2,4-triazol-3-yl)phenyl][1,2,4]triazolo[4,3-a]pyridin-3(2H)-one;
2-[(2E)-2-(aminomethyl)-3-fluoroprop-2-en-1-yl]-6-[4-(1,2-oxazol-3-yl)phenyl][1,2,4]triazolo[4,3-a]pyridin-3(2H)-one;
N-[4-[2-[(2E)-2-(aminomethyl)-3-fluoroprop-2-en-1-yl]-3-oxo-2,3-dihydro[1,2,4]triazolo[4,3-a]pyridin-6-yl]pyridin-2-yl]acetamide;
2-[(2E)-2-(aminomethyl)-3-fluoroprop-2-en-1-yl]-6-[6-(trifluoromethyl)pyridin-3-yl][1,2,4]triazolo[4,3-a]pyridin-3(2H)-one;
2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one;
2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one;
2-[(2E)-2-(aminomethyl)-3-fluoroprop-2-en-1-yl]-6-(1,3-benzodioxol-5-yl)[1,2,4]triazolo[4,3-a]pyridin-3(2H)-one;
2-[(2E)-2-(aminomethyl)-3-fluoroprop-2-en-1-yl]-6-(2,3-dihydro-1,4-benzodioxin-6-yl)[1,2,4]triazolo[4,3-a]pyridin-3(2H)-one;
6-(2-amino-1,3-benzothiazol-5-yl)-2-[(2E)-2-(aminomethyl)-3-fluoroprop-2-en-1-yl][1,2,4]triazolo[4,3-a]pyridin-3(2H)-one;
N-[5-[2-[(2E)-2-(aminomethyl)-3-fluoroprop-2-en-1-yl]-3-oxo-2,3-dihydro[1,2,4]triazolo[4,3-a]pyridin-6-yl]-1,3-benzothiazol-2-yl]acetamide;
2-[(2E)-2-(aminomethyl)-3-fluoroprop-2-en-1-yl]-6-(2,1,3-benzoxadiazol-5-yl)[1,2,4]triazolo[4,3-a]pyridin-3(2H)-one;
6-[2-[(2E)-2-(aminomethyl)-3-fluoroprop-2-en-1-yl]-3-oxo-2,3-dihydro[1,2,4]triazolo[4,3-a]pyridin-6-yl]-8-methyl-3,4-dihydroquinolin-2(1H)-one;
N-[4-[2-[(2E)-2-(aminomethyl)-3-fluoroprop-2-en-1-yl]-3-oxo-2,3-dihydro[1,2,4]triazolo[4,3-a]pyridin-5-yl]phenyl]acetamide;
2-[(2E)-2-(aminomethyl)-3-fluoroprop-2-en-1-yl]-5-[4-(1,2-oxazol-3-yl)phenyl][1,2,4]triazolo[4,3-a]pyridin-3(2H)-one;
2-[(2E)-2-(aminomethyl)-3-fluoroprop-2-en-1-yl]-5-(1,3-benzodioxol-5-yl)[1,2,4]triazolo[4,3-a]pyridin-3(2H)-one;
2-[(2E)-2-(aminomethyl)-3-fluoroprop-2-en-1-yl]-5-(2,1,3-benzoxadiazol-5-yl)[1,2,4]triazolo[4,3-a]pyridin-3(2H)-one;
2-[(2E)-2-(aminomethyl)-3-fluoroprop-2-en-1-yl]-7-[3-(methylsulfonyl)phenyl][1,2,4]triazolo[4,3-a]pyridin-3(2H)-one;
2-[(2E)-2-(aminomethyl)-3-fluoroprop-2-en-1-yl]-7-2-[(dimethylamino)methyl]phenyl[1,2,4]triazolo[4,3-a]pyridin-3(2H)-one;
2-[(2E)-2-(aminomethyl)-3-fluoroprop-2-en-1-yl]-7-[4-(morpholin-4-ylcarbonyl)phenyl][1,2,4]triazolo[4,3-a]pyridin-3(2H)-one;
2-[(2E)-2-(aminomethyl)-3-fluoroprop-2-en-1-yl]-7-[4-(1,2-oxazol-3-yl)phenyl][1,2,4]triazolo[4,3-a]pyridin-3(2H)-one;
2-[(2E)-2-(aminomethyl)-3-fluoroprop-2-en-1-yl]-7-[3-(1H-pyrazol-3-yl)phenyl][1,2,4]triazolo[4,3-a]pyridin-3(2H)-one;
2-[(2E)-2-(aminomethyl)-3-fluoroprop-2-en-1-yl]-7-[4-(1,2,5-oxadiazol-3-yl)phenyl][1,2,4]triazolo[4,3-a]pyridin-3(2H)-one;
2-[(2E)-2-(aminomethyl)-3-fluoroprop-2-en-1-yl]-7-[3-(5-cyclopropyl-1,2,4-oxadiazol-3-yl)phenyl][1,2,4]triazolo[4,3-a]pyridin-3(2H)-one;
2-[(2E)-2-(aminomethyl)-3-fluoroprop-2-en-1-yl]-7-[4-(5-cyclopropyl-1,2,4-oxadiazol-3-yl)phenyl][1,2,4]triazolo[4,3-a]pyridin-3(2H)-one;
2-[(2E)-2-(aminomethyl)-3-fluoroprop-2-en-1-yl]-7-[6-(trifluoromethyl)pyridin-3-yl][1,2,4]triazolo[4,3-a]pyridin-3(2H)-one;

2-[(2E)-2-(aminomethyl)-3-fluoroprop-2-en-1-yl]-7-(6-methoxypyridin-3-yl)[1,2,4]triazolo[4,3-a]pyridin-3(2H)-one;
2-[(2E)-2-(aminomethyl)-3-fluoroprop-2-en-1-yl]-7-[6-(dimethylamino)pyridin-3-yl][1,2,4]triazolo[4,3-a]pyridin-3(2H)-one;
2-[(2E)-2-(aminomethyl)-3-fluoroprop-2-en-1-yl]-7-[6-(morpholin-4-yl)pyridin-3-yl][1,2,4]triazolo[4,3-a]pyridin-3(2H)-one;
2-[(2E)-2-(aminomethyl)-3-fluoroprop-2-en-1-yl]-7-(1,2,3,6-tetrahydropyridin-4-yl)[1,2,4]triazolo[4,3-a]pyridin-3(2H)-one;
2-[(2E)-2-(aminomethyl)-3-fluoroprop-2-en-1-yl]-7-(1H-pyrrolo[2,3-b]pyridin-3-yl)[1,2,4]triazolo[4,3-a]pyridin-3(2H)-one;
2-[(2E)-2-(aminomethyl)-3-fluoroprop-2-en-1-yl]-7-(1,3-benzodioxol-5-yl)[1,2,4]triazolo[4,3-a]pyridin-3(2H)-one;
2-[(2E)-2-(aminomethyl)-3-fluoroprop-2-en-1-yl]-7-(1H-indazol-6-yl)[1,2,4]triazolo[4,3a]pyridin-3(2H)-one;
2-[(2E)-2-(aminomethyl)-3-fluoroprop-2-en-1-yl]-7-(2,1,3-benzoxadiazol-5-yl)[1,2,4]triazolo[4,3-a]pyridin-3(2H)-one;
2-[(2E)-2-(aminomethyl)-3-fluoroprop-2-en-1-yl]-7-(1H-benzotriazol-6-yl)[1,2,4]triazolo[4,3-a]pyridin-3(2H)-one;
2-[(2E)-2-(aminomethyl)-3-fluoroprop-2-en-1-yl]-7-(1H-pyrrolo[2,3-b]pyridin-4-yl)[1,2,4]triazolo[4,3-a]pyridin-3(2H)-one;
7-[2-[(2E)-2-(aminomethyl)-3-fluoroprop-2-en-1-yl]-3-oxo-2,3-dihydro[1,2,4]triazolo[4,3-a]pyridin-7-yl]-1,4-dihydro-2H-3,1-benzoxazin-2-one;
6-[2-[(2E)-2-(aminomethyl)-3-fluoroprop-2-en-1-yl]-3-oxo-2,3-dihydro[1,2,4]triazolo[4,3-a]pyridin-7-yl]-2H-1,4-benzoxazine-3(4H)-one;
6-[2-[(2E)-2-(aminomethyl)-3-fluoroprop-2-en-1-yl]-3-oxo-2,3-dihydro[1,2,4]triazolo[4,3-a]pyridin-7-yl]-8-methyl-3,4-dihydroquinolin-2(1H)-one;
2-[(2E)-2-(aminomethyl)-3-fluoroprop-2-en-1-yl]-7-(4-methyl-3,4-dihydro-2H-1,4-benzoxazin-7-yl)[1,2,4]triazolo[4,3-a]pyridin-3(2H)-one;
2-[2-(aminomethyl)-3,3-difluoro-allyl]-5-bromo-[1,2,4]triazolo[4,3-a]pyridin-3-one;
2-[2-(aminomethyl)-3,3-difluoro-allyl]-6-bromo-[1,2,4]triazolo[4,3-a]pyridin-3-one;
2-[2-(aminomethyl)-3,3-difluoro-allyl]-7-bromo-[1,2,4]triazolo[4,3-a]pyridin-3-one;
2-[2-(aminomethyl)-3,3-difluoro-allyl]-7-(4-methylsulfonylphenyl)-[1,2,4]triazolo[4,3-a]pyridin-3-one;
2-[2-(aminomethyl)-3,3-difluoro-allyl]-7-(4-piperazin-1-ylphenyl)-[1,2,4]triazolo[4,3-a]pyridin-3-one;
2-[2-(aminomethyl)-3,3-difluoro-allyl]-7-[6-(trifluoromethyl)-3-pyridyl]-[1,2,4]triazolo[4,3-a]pyridin-3-one;
2-[2-(aminomethyl)-3,3-difluoro-allyl]-7-[6-(dimethylamino)-3-pyridyl]-[1,2,4]triazolo[4,3-a]pyridin-3-one;
2-[2-(aminomethyl)-3,3-difluoro-allyl]-7-(1,3-benzodioxol-5-yl)-[1,2,4]triazolo[4,3-a]pyridin-3-one;
6-[2-[2-(aminomethyl)-3,3-difluoro-allyl]-3-oxo-[1,2,4]triazolo[4,3-a]pyridin-7-yl]-8-methyl-3,4-dihydro-1H-quinolin-2-one;
6-[2-[2-(aminomethyl)-3,3-difluoro-allyl]-3-oxo-[1,2,4]triazolo[4,3-a]pyridin-7-yl]-1-methyl-3,4-dihydroquinolin-2-one;
2-[2-(aminomethyl)-3,3-difluoro-allyl]-7-(1-ethylpyrazol-4-yl)-[1,2,4]triazolo[4,3-a]pyridin-3-one;
2-[2-(aminomethyl)-3,3-difluoro-allyl]-7-[2-(1-methylpyrazol-4-yl)ethynyl]-[1,2,4]triazolo[4,3-a]pyridin-3-one;
2-[2-(aminomethyl)-3,3-difluoro-allyl]-7-[2-[6-(dimethylamino)-3-pyridyl]ethynyl]-[1,2,4]triazolo[4,3-a]pyridin-3-one;
2-[2-(aminomethyl)-3,3-difluoro-allyl]-7-[2-(6-morpholino-3-pyridyl)ethynyl]-[1,2,4]triazolo[4,3-a]pyridin-3-one;
2-[2-(aminomethyl)-3,3-difluoro-allyl]-7-[2-(3,4-dihydro-2H-1,4-benzoxazin-6-yl)ethynyl]-[1,2,4]triazolo[4,3-a]pyridin-3-one;
2-[2-(aminomethyl)-3,3-difluoro-allyl]-7-[2-(2,3-dihydro-1H-pyrido[2,3-b][1,4]oxazin-7-yl)ethynyl]-[1,2,4]triazolo[4,3-a]pyridin-3-one;
2-[2-(aminomethyl)-3,3-difluoro-allyl]-7-[2-(3,4-dihydro-2H-pyrido[3,2-b][1,4]oxazin-7-yl)ethynyl]-[1,2,4]triazolo[4,3-a]pyridin-3-one;
6-[2-[2-[2-(aminomethyl)-3,3-difluoro-allyl]-3-oxo-[1,2,4]triazolo[4,3-a]pyridin-7-yl]ethynyl]-3,4-dihydro-1H-quinolin-2-one; and
2-[2-(aminomethyl)-3,3-difluoro-allyl]-7-[2-(4-methyl-2,3-dihydro-1,4-benzoxazin-7-yl)ethynyl]-[1,2,4]triazolo[4,3-a]pyridin-3-one;
or a stereoisomer thereof, or a pharmaceutically acceptable salt thereof.

Para. AP. A pharmaceutical composition comprising the compound according to any one of Paras. A-AO, or a stereoisomer thereof, or a pharmaceutically acceptable salt thereof, and at least one pharmaceutically acceptable excipient.

Para. AQ. A method of inhibiting vascular adhesion protein (VAP-1), comprising administering to a mammal a therapeutically effective amount of the compound or a pharmaceutically acceptable salt thereof according to any one of Paras. A-AO.

Para. AR. A method of treating NASH in a subject in need thereof, the method comprising administering to the subject a therapeutically effective amount of the compound according to any one of Paras. A-AO, or a stereoisomer thereof, or a pharmaceutically acceptable salt thereof, or a therapeutically effective amount of the pharmaceutical composition according to Para. AP.

Para. AS. Use of the compound according to any one of Paras. A-AO, or a stereoisomer thereof, or a pharmaceutically acceptable salt thereof, for the manufacture of a medicament for the treatment of NASH.

Para. AT. A compound according to any one of Paras. A-AO, or a stereoisomer thereof, or a pharmaceutically acceptable salt thereof, for use in treating NASH.

Para. AU. A composition according to Para. AP for use in treating NASH.

Para. AV. A compound according to any one of Paras. A-AO, or a stereoisomer thereof, or a pharmaceutically acceptable salt thereof, for use in inhibiting VAP-1.

Para. AW. A composition according to Para. AP for use in inhibiting VAP-1.

Para. AX. A method of treating a disease mediated by VAP-1 in a subject in need thereof, the method comprising administering to the subject a therapeutically effective amount of the compound according to any one of Paras. A-AO, or a stereoisomer thereof, or a pharmaceutically acceptable salt thereof, or a therapeutically effective amount of the pharmaceutical composition according to Para. AP.

Para. AY. The method of Para. AX, wherein the disease mediated by VAP-1 is selected from the group consisting of lipid and lipoprotein disorders, conditions and diseases which result from chronic fatty and fibrotic degeneration of organs due to accumulated lipid and specifically triglyceride accumulation and subsequent activation of profibrotic pathways, Type I or Type II Diabetes and clinical complications of Type I and Type II Diabetes, chronic intrahepatic or some forms of extrahepatic cholestatic conditions, liver fibrosis, acute intraheptic cholestatic conditions, obstructive or chronic inflammatory disorders that arise out of improper bile composition, gastrointestinal conditions with a reduced uptake of dietary fat and fat-soluble dietary vitamins, inflammatory bowel diseases, obesity and metabolic syndrome (combined conditions of dyslipidemia, diabetes and abnormally high body-mass index), persistent infections by intracellular bacteria or parasitic protozoae, non-malignant hyperproliferative disorders, malignant hyperproliferative disorders, colon adenocarcinoma and hepatocellular carcinoma in particular, liver steatosis and associated syndromes, Hepatitis B infection, Hepatitis C infection and/or of cholestatic and fibrotic effects that are associated with alcohol-induced cirrhosis or with viral-borne forms of hepatitis, liver failure or liver malfunction as an outcome of chronic liver diseases or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

Para. AZ. A method of preparing a compound of Formula 1a, or a stereoisomer thereof, or a pharmaceutically acceptable salt thereof,

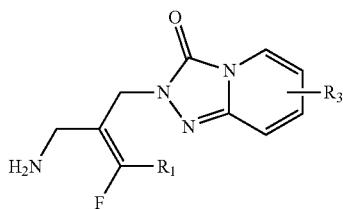
(Formula 1a)

the method comprising (a) reacting a compound of Formula 2 with a compound of Formula 3a or a compound of Formula 3b to obtain a compound of Formula 1aa:

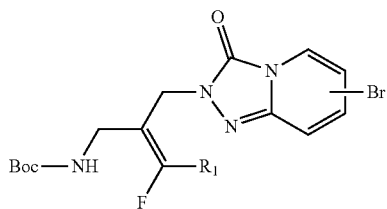
(Formula 2)

Z—R$_3$ (Formula 3a)

HC≡CR (Formula 3b)

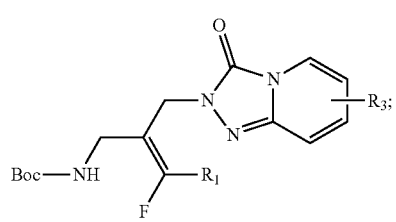
(Formula 1aa)

wherein

Boc is an amine protecting group;

R$_1$ is hydrogen or fluoro;

R$_3$ is selected from the group consisting of C$_{1-6}$ alkyl, —R, and —C≡C—R;

R is substituted or unsubstituted cyclic ring, optionally containing 1 to 5 heteroatom ring members chosen from O, N, or S, and the cyclic ring is aromatic or non-aromatic; and Z is is boronic acid (B(OH)$_2$) or boronic acid pinacol ester; and (b) removing Boc from the compound of Formula 1aa under reaction conditions to obtain the compound of Formula 1a, or the stereoisomer thereof, or the pharmaceutically acceptable salt thereof.

Para. BA. The method of Para. AZ, wherein the compound of Formula 2 is obtained by (a) reacting a compound of Formula 4 with hydrazine to obtain a compound of Formula 5:

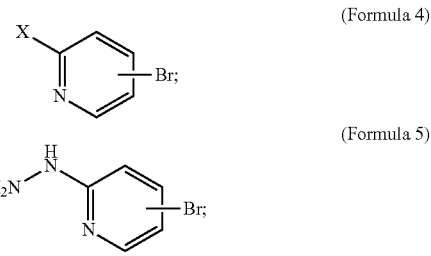
(Formula 4)

(Formula 5)

wherein X is F or Cl;

(b) reacting the compound of Formula 5 under cyclization conditions to obtain a compound of Formula 6:
and

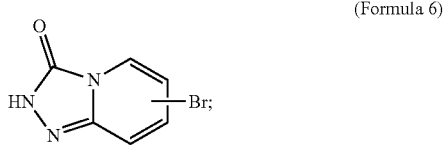
(Formula 6)

(c) reacting the compound of Formula 6 with a compound of Formula 8 to obtain the compound of Formula 2:

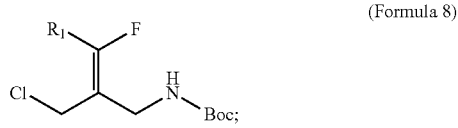
(Formula 8)

wherein R$_1$ is hydrogen or fluoro.

Para. BB. The method of Para. BA, wherein the cyclization conditions comprise reacting the compound of Formula 5 with carbonyldiimidazole (CDI) in a polar solvent at a temperature ranging from room temperature to 90° C.

Para. BC. The method of any one of Paras. AZ-BB, wherein R is a cyclic ring selected from the group consisting of benzene, pyridine, tetrahydropyridine, pyrazole, benzodioxole, 2,3-dihydrobenzodioxine, benzothiazole, benzoxadiazole, benzotriazole, indazole, pyrrolo[2,3-b]pyridine, 3,4-dihydroquinolin-2-one, 3,4-dihydro-1,4-benzoxazine, 1,4-benzoxazin-3-one, 1,3-dihydro-3,1-benzoxazin-2-one, 2,3-dihydro-pyrido[2,3-b][1,4]oxazine, pyrido[2,3-b][1,4]oxazin-2-one, 3,4-dihydro-pyrido[3,2-b][1,4]oxazine, and pyrido[3,2-b][1,4]oxazin-3-one, wherein said cyclic ring is optionally substituted with a substituent selected from the group consisting of $C_{1-6}$ alkyl, trifluoromethyl, $C_{1-6}$ alkoxy, amino, mono- or di-$C_{1-6}$ alkylamino, di-$C_{1-6}$ alkylaminomethyl, $C_{1-6}$ alkylcarbonylamino, $C_{1-6}$ alkylsulfonyl, morpholinylsulfonyl, morpholinylcarbonyl, piperazinyl, morpholinyl, triazolyl, pyrazolyl, oxazolyl, oxadiazolyl, and cyclopropyl-oxadiazolyl.

The invention claimed is:
1. A compound of Formula X

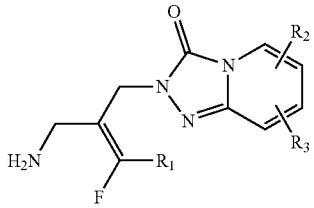

(Formula X)

or a stereoisomer thereof or a pharmaceutically acceptable salt thereof;
wherein
$R_1$ is hydrogen or fluoro; and
$R_2$ and $R_3$, each independently, are selected from the group consisting of hydrogen, halogen, $C_{1-6}$ alkyl, —R, and —C≡C—R;
wherein said R is substituted or unsubstituted cyclic ring, optionally containing 1 to 5 heteroatom ring members chosen from O, N, or S, and the cyclic ring is aromatic or non-aromatic.

2. The compound, or a stereoisomer thereof or a pharmaceutically acceptable salt thereof, of claim 1, wherein R is substituted or unsubstituted aryl.

3. The compound, or a stereoisomer thereof or a pharmaceutically acceptable salt thereof, of claim 1, wherein R is substituted or unsubstituted phenyl.

4. The compound, or a stereoisomer thereof or a pharmaceutically acceptable salt thereof, of claim 1, wherein R is substituted or unsubstituted heteroaryl.

5. The compound, or a stereoisomer thereof or a pharmaceutically acceptable salt thereof, of claim 1, wherein R is substituted or unsubstituted non-aromatic heterocyclic ring.

6. The compound, or a stereoisomer thereof or a pharmaceutically acceptable salt thereof, of claim 1, wherein the substituted or unsubstituted cyclic ring is selected from the group consisting of substituted or unsubstituted phenyl, substituted or unsubstituted pyridinyl, substituted or unsubstituted tetrahydropyridinyl, substituted or unsubstituted pyrazolyl, substituted or unsubstituted benzodioxolyl, substituted or unsubstituted 2,3-dihydro-benzodioxinyl, substituted or unsubstituted benzothiazolyl, substituted or unsubstituted benzoxadiazolyl, substituted or unsubstituted benzotriazolyl, substituted or unsubstituted indazolyl, substituted or unsubstituted pyrrolo[2,3-b]pyridinyl, substituted or unsubstituted 3,4-dihydroquinolin-2-onyl, substituted or unsubstituted 3,4-dihydro-1,4-benzoxazinyl, substituted or unsubstituted 1,4-benzoxazin-3-onyl, substituted or unsubstituted 1,3-dihydro-3,1-benzoxazin-2-onyl, substituted or unsubstituted 2,3-dihydro-pyrido[2,3-b][1,4]oxazinyl, substituted or unsubstituted pyrido[2,3-b][1,4]oxazin-2-onyl, substituted or unsubstituted 3,4-dihydro-pyrido[3,2-b][1,4]oxazinyl, and substituted or unsubstituted pyrido[3,2-b][1,4]oxazin-3-onyl.

7. The compound, or a stereoisomer thereof or a pharmaceutically acceptable salt thereof, of claim 1, wherein said $R_1$ is fluoro.

8. The compound, or a stereoisomer thereof or a pharmaceutically acceptable salt thereof, of claim 1, wherein said $R_1$ is hydrogen.

9. The compound, or a stereoisomer thereof or a pharmaceutically acceptable salt thereof, of claim 1, wherein said $R_2$ is hydrogen and $R_3$ is halogen, —R, or —C≡C—R.

10. The compound, or a stereoisomer thereof or a pharmaceutically acceptable salt thereof, of claim 1, wherein
$R_1$ is fluoro,
$R_2$ is hydrogen,
$R_3$ is halogen or —R,
wherein said R is a cyclic ring selected from the group consisting of phenyl and pyrazolyl,
wherein said cyclic ring is substituted with a substituent selected from the group consisting of $C_{1-6}$ alkyl, $C_{1-6}$ alkylsulfonyl, and piperazinyl.

11. The compound of claim 1 of Formula 11

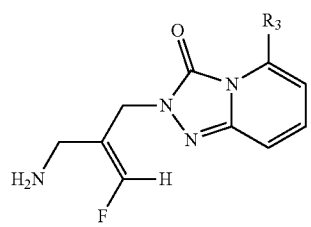

(Formula 11)

or a stereoisomer thereof or a pharmaceutically acceptable salt thereof;
wherein
$R_3$ is substituted or unsubstituted aryl, substituted or unsubstituted heteroaryl, or substituted or unsubstituted benzodioxolyl.

12. The compound, or a stereoisomer thereof or a pharmaceutically acceptable salt thereof, of claim 11, wherein $R_3$ is substituted aryl.

13. The compound, or a stereoisomer thereof or a pharmaceutically acceptable salt thereof, of claim 11, wherein $R_3$ is substituted or unsubstituted benzodioxolyl, substituted or unsubstituted benzoxadiazolyl, or phenyl, wherein the phenyl is substituted with $C_{1-6}$ alkylcarbonylamino or oxazolyl.

14. The compound of claim 1 of Formula 12

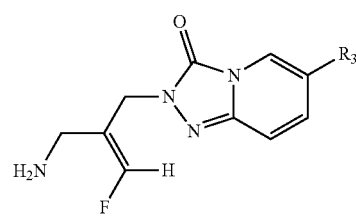

(Formula 12)

or a stereoisomer thereof or a pharmaceutically acceptable salt thereof;

wherein

R₃ is substituted or unsubstituted aryl, substituted or unsubstituted heteroaryl, or substituted or unsubstituted heterocyclic ring.

15. The compound, or a stereoisomer thereof or a pharmaceutically acceptable salt thereof, of claim 14, wherein R₃ is substituted or unsubstituted benzodioxolyl, substituted or unsubstituted 2,3-dihydrobenzodioxinyl, substituted or unsubstituted 3,4-dihydroquinolin-2-onyl, substituted or unsubstituted benzothiazolyl, substituted or unsubstituted benzoxadiazolyl, substituted phenyl, or substituted pyridinyl.

16. The compound of claim 1 of Formula 13

(Formula 13)

or a stereoisomer thereof or a pharmaceutically acceptable salt thereof;

wherein

R₃ is substituted or unsubstituted aryl or a substituted or unsubstituted cyclic ring.

17. The compound, or a stereoisomer thereof or a pharmaceutically acceptable salt thereof, of claim 16, wherein R₃ is substituted or unsubstituted aryl.

18. The compound, or a stereoisomer thereof or a pharmaceutically acceptable salt thereof, of claim 16, wherein R₃ is substituted or unsubstituted benzoxadiazolyl, substituted or unsubstituted 3,4-dihydroquinolin-2-onyl, substituted or unsubstituted benzodioxolyl, substituted or unsubstituted indazolyl, substituted or unsubstituted pyrazolyl, substituted or unsubstituted benzotriazoyl, substituted or unsubstituted 1,3-dihydro-3,1-benzoxazin-2-onyl, substituted or unsubstituted 1,4-benzoxazin-3-onyl, substituted or unsubstituted 3,4-dihydro-1,4-benzoxazinyl, or substituted phenyl.

19. The compound, or a stereoisomer thereof or a pharmaceutically acceptable salt thereof, of claim 16, wherein R₃ is a substituted or unsubstituted heterocyclic group.

20. The compound, or a stereoisomer thereof or a pharmaceutically acceptable salt thereof, of claim 16, wherein R₃ is substituted or unsubstituted heteroaryl.

21. The compound, or a stereoisomer thereof or a pharmaceutically acceptable salt thereof, of claim 16, wherein R₃ is a cyclic ring selected from the group consisting of phenyl, pyridinyl, benzoxadiazolyl, 3,4-dihydroquinolin-2-onyl, benzodioxolyl, indazolyl, benzotriazolyl, 1,3-dihydro-3,1-benzoxazin-2-onyl, 1,4-benzoxazin-3-onyl, 3,4-dihydro-1,4-benzoxazinyl, or pyrrolo[2,3-b]pyridinyl;

wherein said cyclic ring is optionally substituted with a substituent selected from the group consisting of $C_{1-6}$ alkyl, trifluoromethyl, $C_{1-6}$ alkoxy, mono- or di-$C_{1-6}$ alkylamino, di-$C_{1-6}$alkylaminomethyl, $C_{1-6}$ alkyl sulfonyl, morpholinylcarbonyl, morpholinyl, pyrazolyl, oxazolyl, oxadiazolyl, and cyclopropyl-oxadiazolyl.

22. The compound of claim 1 of Formula 14

(Formula 14)

or a stereoisomer thereof or a pharmaceutically acceptable salt thereof;

wherein

R is substituted or unsubstituted aryl, substituted or unsubstituted heteroaryl, or substituted or unsubstituted heterocyclic ring.

23. The compound, or a stereoisomer thereof or a pharmaceutically acceptable salt thereof, of claim 22, wherein R is substituted aryl.

24. The compound, or a stereoisomer thereof or a pharmaceutically acceptable salt thereof, of claim 22, wherein R is substituted or unsubstituted heteroaryl.

25. The compound, or a stereoisomer thereof or a pharmaceutically acceptable salt thereof, of claim 22, wherein R is substituted pyrazol, substituted pyridinyl, substituted or unsubstituted 2,3-dihydro-pyrido[2,3-b][1,4]oxazinyl, or substituted or unsubstituted 3,4-dihydro-pyrido[3,2-b][1,4]oxazinyl.

26. A compound selected from the group consisting of:
2-[(2E)-2-(aminomethyl)-3-fluoroprop-2-en-1-yl]-6-bromo[1,2,4]triazolo[4,3-a]pyridin-3(2H)-one;
N-[4-[2-[(2E)-2-(aminomethyl)-3-fluoroprop-2-en-1-yl]-3-oxo-2,3-dihydro[1,2,4]triazolo[4,3-a]pyridin-6-yl]phenyl]acetamide;
2-[(2E)-2-(aminomethyl)-3-fluoroprop-2-en-1-yl]-6-[4-(methylsulfonyl)phenyl][1,2,4]triazolo[4,3-a]pyridin-3(2H)-one;
2-[(2E)-2-(aminomethyl)-3-fluoroprop-2-en-1-yl]-6-[4-(morpholin-4-ylsulfonyl)phenyl][1,2,4]triazolo[4,3-a]pyridin-3(2H)-one;
2-[(2E)-2-(aminomethyl)-3-fluoroprop-2-en-1-yl]-6-[4-(1H-1,2,4-triazol-3-yl)phenyl][1,2,4]triazolo[4,3-a]pyridin-3(2H)-one;
2-[(2E)-2-(aminomethyl)-3-fluoroprop-2-en-1-yl]-6-[3-(1H-1,2,4-triazol-3-yl)phenyl][1,2,4]triazolo[4,3-a]pyridin-3(2H)-one;
2-[(2E)-2-(aminomethyl)-3-fluoroprop-2-en-1-yl]-6-[4-(1,2-oxazol-3-yl)phenyl][1,2,4]triazolo[4,3-a]pyridin-3(2H)-one;
N-[4-[2-[(2E)-2-(aminomethyl)-3-fluoroprop-2-en-1-yl]-3-oxo-2,3-dihydro[1,2,4]triazolo[4,3-a]pyridin-6-yl]pyridin-2-yl]acetamide;
2-[(2E)-2-(aminomethyl)-3-fluoroprop-2-en-1-yl]-6-[6-(trifluoromethyl)pyridin-3-yl][1,2,4]triazolo[4,3-a]pyridin-3(2H)-one;
2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one;
2-[(2E)-2-(aminomethyl)-3-fluoroprop-2-en-1-yl]-6-[6-(morpholin-4-yl)pyridin-3-yl][1,2,4]triazolo[4,3-a]pyridin-3(2H)-one;
2-[(2E)-2-(aminomethyl)-3-fluoroprop-2-en-1-yl]-6-(1,3-benzodioxol-5-yl)[1,2,4]triazolo[4,3-a]pyridin-3(2H)-one;

2-[(2E)-2-(aminomethyl)-3-fluoroprop-2-en-1-yl]-6-(2,3-dihydro-1,4-benzodioxin-6-yl)[1,2,4]triazolo[4,3-a]pyridin-3(2H)-one;
6-(2-amino-1,3-benzothiazol-5-yl)-2-[(2E)-2-(aminomethyl)-3-fluoroprop-2-en-1-yl][1,2,4]triazolo[4,3-a]pyridin-3(2H)-one;
N-5-[2-[(2E)-2-(aminomethyl)-3-fluoroprop-2-en-1-yl]-3-oxo-2,3-dihydro[1,2,4]triazolo[4,3-a]pyridin-6-yl]-1,3-benzothiazol-2-yl]acetamide;
2-[(2E)-2-(aminomethyl)-3-fluoroprop-2-en-1-yl]-6-(2,1,3-benzoxadiazol-5-yl)[1,2,4]triazolo[4,3-a]pyridin-3(2H)-one;
6-[2-[(2E)-2-(aminomethyl)-3-fluoroprop-2-en-1-yl]-3-oxo-2,3-dihydro[1,2,4]triazolo[4,3-a]pyridin-6-yl]-8-methyl-3,4-dihydroquinolin-2(1H)-one;
N-[4-[2-[(2E)-2-(aminomethyl)-3-fluoroprop-2-en-1-yl]-3-oxo-2,3-dihydro[1,2,4]triazolo[4,3-a]pyridin-5-yl]phenyl]acetamide;
2-[(2E)-2-(aminomethyl)-3-fluoroprop-2-en-1-yl]-5-[4-(1,2-oxazol-3-yl)phenyl][1,2,4]triazolo[4,3-a]pyridin-3(2H)-one;
2-[(2E)-2-(aminomethyl)-3-fluoroprop-2-en-1-yl]-5-(1,3-benzodioxol-5-yl)[1,2,4]triazolo[4,3-a]pyridin-3(2H)-one;
2-[(2E)-2-(aminomethyl)-3-fluoroprop-2-en-1-yl]-5-(2,1,3-benzoxadiazol-5-yl)[1,2,4]triazolo[4,3-a]pyridin-3(2H)-one;
2-[(2E)-2-(aminomethyl)-3-fluoroprop-2-en-1-yl]-7-[3-(methyl sulfonyl)phenyl][1,2,4]triazolo[4,3-a]pyridin-3(2H)-one;
2-[(2E)-2-(aminomethyl)-3-fluoroprop-2-en-1-yl]-7-2-[(dimethylamino)methyl]phenyl[1,2,4]triazolo[4,3-a]pyridin-3(2H)-one;
2-[(2E)-2-(aminomethyl)-3-fluoroprop-2-en-1-yl]-7-[4-(morpholin-4-ylcarbonyl)phenyl][1,2,4]triazolo[4,3-a]pyridin-3(2H)-one;
2-[(2E)-2-(aminomethyl)-3-fluoroprop-2-en-1-yl]-7-[4-(1,2-oxazol-3-yl)phenyl][1,2,4]triazolo[4,3-a]pyridin-3(2H)-one;
2-[(2E)-2-(aminomethyl)-3-fluoroprop-2-en-1-yl]-7-[3-(1H-pyrazol-3-yl)phenyl][1,2,4]triazolo[4,3-a]pyridin-3(2H)-one;
2-[(2E)-2-(aminomethyl)-3-fluoroprop-2-en-1-yl]-7-[4-(1,2,5-oxadiazol-3-yl)phenyl][1,2,4]triazolo[4,3-a]pyridin-3(2H)-one;
2-[(2E)-2-(aminomethyl)-3-fluoroprop-2-en-1-yl]-7-[3-(5-cyclopropyl-1,2,4-oxadiazol-3-yl)phenyl][1,2,4]triazolo[4,3-a]pyridin-3(2H)-one;
2-[(2E)-2-(aminomethyl)-3-fluoroprop-2-en-1-yl]-7-[4-(5-cyclopropyl-1,2,4-oxadiazol-3-yl)phenyl][1,2,4]triazolo[4,3-a]pyridin-3(2H)-one;
2-[(2E)-2-(aminomethyl)-3-fluoroprop-2-en-1-yl]-7-[6-(trifluoromethyl)pyridin-3-yl][1,2,4]triazolo[4,3-a]pyridin-3(2H)-one;
2-[(2E)-2-(aminomethyl)-3-fluoroprop-2-en-1-yl]-7-(6-methoxypyridin-3-yl)[1,2,4]triazolo[4,3-a]pyridin-3(2H)-one;
2-[(2E)-2-(aminomethyl)-3-fluoroprop-2-en-1-yl]-7-[6-(dimethylamino)pyridin-3-yl][1,2,4]triazolo[4,3-a]pyridin-3(2H)-one;
2-[(2E)-2-(aminomethyl)-3-fluoroprop-2-en-1-yl]-7-[6-(morpholin-4-yl)pyridin-3-yl][1,2,4]triazolo[4,3-a]pyridin-3(2H)-one;
2-[(2E)-2-(aminomethyl)-3-fluoroprop-2-en-1-yl]-7-(1,2,3,6-tetrahydropyridin-4-yl)[1,2,4]triazolo[4,3-a]pyridin-3(2H)-one;
2-[(2E)-2-(aminomethyl)-3-fluoroprop-2-en-1-yl]-7-(1H-pyrrolo[2,3-b]pyridin-3-yl)[1,2,4]triazolo[4,3-a]pyridin-3(2H)-one;
2-[(2E)-2-(aminomethyl)-3-fluoroprop-2-en-1-yl]-7-(1,3-benzodioxol-5-yl)[1,2,4]triazolo[4,3-a]pyridin-3(2H)-one;
2-[(2E)-2-(aminomethyl)-3-fluoroprop-2-en-1-yl]-7-(1H-indazol-6-yl)[1,2,4]triazolo[4,a]pyridin-3(2H)-one;
2-[(2E)-2-(aminomethyl)-3-fluoroprop-2-en-1-yl]-7-(2,1,3-benzoxadiazol-5-yl)[1,2,4]triazolo[4,3-a]pyridin-3(2H)-one;
2-[(2E)-2-(aminomethyl)-3-fluoroprop-2-en-1-yl]-7-(1H-benzotriazol-6-yl)[1,2,4]triazolo[4,3-a]pyridin-3(2H)-one;
2-[(2E)-2-(aminomethyl)-3-fluoroprop-2-en-1-yl]-7-(1H-pyrrolo[2,3-b]pyridin-4-yl)[1,2,4]triazolo[4,3-a]pyridin-3(2H)-one;
7-[2-[(2E)-2-(aminomethyl)-3-fluoroprop-2-en-1-yl]-3-oxo-2,3-dihydro[1,2,4]triazolo[4,3-a]pyridin-7-yl]-1,4-dihydro-2H-3,1-benzoxazin-2-one;
6-[2-[(2E)-2-(aminomethyl)-3-fluoroprop-2-en-1-yl]-3-oxo-2,3-dihydro[1,2,4]triazolo[4,3-a]pyridin-7-yl]-2H-1,4-benzoxazine-3(4H)-one;
6-[2-[(2E)-2-(aminomethyl)-3-fluoroprop-2-en-1-yl]-3-oxo-2,3-dihydro[1,2,4]triazolo[4,3-a]pyridin-7-yl]-8-methyl-3,4-dihydroquinolin-2(1H)-one;
2-[(2E)-2-(aminomethyl)-3-fluoroprop-2-en-1-yl]-7-(4-methyl-3,4-dihydro-2H-1,4-benzoxazin-7-yl)[1,2,4]triazolo[4,3-a]pyridin-3(2H)-one;
2-[2-(aminomethyl)-3,3-difluoro-allyl]-5-bromo-[1,2,4]triazolo[4,3-a]pyridin-3-one;
2-[2-(aminomethyl)-3,3-difluoro-allyl]-6-bromo-[1,2,4]triazolo[4,3-a]pyridin-3-one;
2-[2-(aminomethyl)-3,3-difluoro-allyl]-7-bromo-[1,2,4]triazolo[4,3-a]pyridin-3-one;
2-[2-(aminomethyl)-3,3-difluoro-allyl]-7-(4-methyl sulfonylphenyl)-[1,2,4]triazolo[4,3-a]pyridin-3-one;
2-[2-(aminomethyl)-3,3-difluoro-allyl]-7-(4-piperazin-1-ylphenyl)-[1,2,4]triazolo[4,3-a]pyridin-3-one;
2-[2-(aminomethyl)-3,3-difluoro-allyl]-7-[6-(trifluoromethyl)-3-pyridyl]-[1,2,4]triazolo[4,3-a]pyridin-3-one;
2-[2-(aminomethyl)-3,3-difluoro-allyl]-7-[6-(dimethylamino)-3-pyridyl]-[1,2,4]triazolo[4,3-a]pyridin-3-one;
2-[2-(aminomethyl)-3,3-difluoro-allyl]-7-(1,3-benzodioxol-5-yl)-[1,2,4]triazolo[4,3-a]pyridin-3-one;
6-[2-[2-(aminomethyl)-3,3-difluoro-allyl]-3-oxo-[1,2,4]triazolo[4,3-a]pyridin-7-yl]-8-methyl-3,4-dihydro-1H-quinolin-2-one;
6-[2-[2-(aminomethyl)-3,3-difluoro-allyl]-3-oxo-[1,2,4]triazolo[4,3-a]pyridin-7-yl]-1-methyl-3,4-dihydroquinolin-2-one;
2-[2-(aminomethyl)-3,3-difluoro-allyl]-7-(1-ethylpyrazol-4-yl)-[1,2,4]triazolo[4,3-a]pyridin-3-one;
2-[2-(aminomethyl)-3,3-difluoro-allyl]-7-[2-(1-methylpyrazol-4-yl)ethynyl]-[1,2,4]triazolo[4,3-a]pyridin-3-one;
2-[2-(aminomethyl)-3,3-difluoro-allyl]-7-[2-[6-(dimethylamino)-3-pyridyl]ethynyl]-[1,2,4]triazolo[4,3-a]pyridin-3-one;
2-[2-(aminomethyl)-3,3-difluoro-allyl]-7-[2-(6-morpholino-3-pyridyl)ethynyl]-[1,2,4]triazolo[4,3-a]pyridin-3-one;
2-[2-(aminomethyl)-3,3-difluoro-allyl]-7-[2-(3,4-dihydro-2H-1,4-benzoxazin-6-yl)ethynyl]-[1,2,4]triazolo[4,3-a]pyridin-3-one;

2-[2-(aminomethyl)-3,3-difluoro-allyl]-7-[2-(2,3-di-hydro-1H-pyrido[2,3-b][1,4]oxazin-7-yl)ethynyl]-[1,2,4]triazolo[4,3-a]pyridin-3-one;

2-[2-(aminomethyl)-3,3-difluoro-allyl]-7-[2-(3,4-di-hydro-2H-pyrido[3,2-b][1,4]oxazin-7-yl)ethynyl]-[1,2,4]triazolo[4,3-a]pyridin-3-one;

6-[2-[2-[2-(aminomethyl)-3,3-difluoro-allyl]-3-oxo-[1,2,4]triazolo[4,3-a]pyridin-7-yl]ethynyl]-3,4-dihydro-1H-quinolin-2-one; and 2-[2-(aminomethyl)-3,3-difluoro-allyl]-7-[2-(4-methyl-2,3-dihydro-1,4-benzoxazin-7-yl)ethynyl]-[1,2,4]triazolo[4,3-a]pyridin-3-one;

or a stereoisomer thereof, or a pharmaceutically acceptable salt thereof.

27. A pharmaceutical composition comprising the compound according to claim 1, or a stereoisomer thereof, or a pharmaceutically acceptable salt thereof, and at least one pharmaceutically acceptable excipient.

28. A method of inhibiting vascular adhesion protein (VAP-1), comprising administering to a mammal a therapeutically effective amount of the compound, or a stereoisomer thereof, or a pharmaceutically acceptable salt thereof according to claim 1.

29. A method of treating nonalcoholic hepatosteatosis (NASH) in a subject in need thereof, the method comprising administering to the subject a therapeutically effective amount of the compound according to claim 1, or a stereoisomer thereof, or a pharmaceutically acceptable salt thereof.

30. A method of treating a disease mediated by VAP-1 in a subject in need thereof, the method comprising administering to the subject a therapeutically effective amount of the compound according to claim 1, or a stereoisomer thereof, or a pharmaceutically acceptable salt thereof.

31. The method of claim 30, wherein the disease mediated by VAP-1 is selected from the group consisting of a lipid disorder, lipoprotein disorder, condition or disease which results from chronic fatty or fibrotic degeneration of organs due to accumulated lipid, triglyceride accumulation and subsequent activation of a profibrotic pathway, Type I Diabetes, Type II Diabetes, complication of Type I or Type II Diabetes, chronic intrahepatic cholestatic condition, extrahepatic cholestatic condition, liver fibrosis, acute intrahepatic cholestatic condition, obstructive or chronic inflammatory disorder that arises out of improper bile composition, gastrointestinal condition with a reduced uptake of dietary fat or fat-soluble dietary vitamin, inflammatory bowel disease, obesity, metabolic syndrome, combined conditions of dyslipidemia, diabetes and abnormally high body-mass index, persistent infection by intracellular bacteria or parasitic protozoae, non-malignant hyperproliferative disorder, malignant hyperproliferative disorder, colon adenocarcinoma, hepatocellular carcinoma, liver steatosis or associated syndrome, Hepatitis B infection, Hepatitis C infection, a cholestatic and fibrotic effect that is associated with alcohol-induced cirrhosis or with viral-borne forms of hepatitis, liver failure or liver malfunction as an outcome of chronic liver disease or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, or a combination thereof.

32. A method of preparing a compound of Formula 1a, or a stereoisomer thereof, or a pharmaceutically acceptable salt thereof,

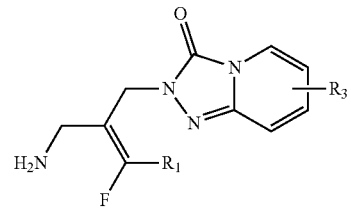

(Formula 1a)

the method comprising (a) reacting a compound of Formula 2 with a compound of Formula 3a or a compound of Formula 3b to obtain a compound of Formula 1aa:

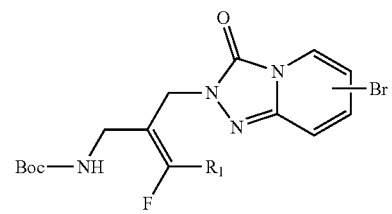

(Formula 2)

Z—$R_3$ (Formula 3a)
HC≡CR (Formula 3b)

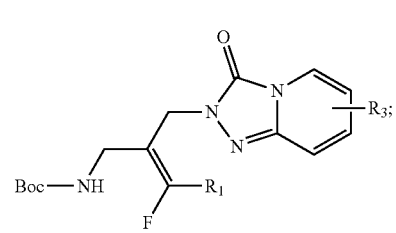

(Formula 1aa)

wherein

Boc is an amine protecting group;

$R_1$ is hydrogen or fluoro;

$R_3$ is selected from the group consisting of $C_{1-6}$ alkyl, —R, and —C≡C—R;

R is substituted or unsubstituted cyclic ring, optionally containing 1 to 5 heteroatom ring members chosen from O, N, or S, and the cyclic ring is aromatic or non-aromatic; and Z is boronic acid (B(OH)$_2$) or boronic acid pinacol ester; and (b) removing Boc from the compound of Formula 1aa under reaction conditions to obtain the compound of Formula 1a, or stereoisomer thereof, or pharmaceutically acceptable salt thereof.

33. The method of claim 32, wherein the compound of Formula 2 is obtained by
(a) reacting a compound of Formula 4 with hydrazine to obtain a compound of Formula 5:

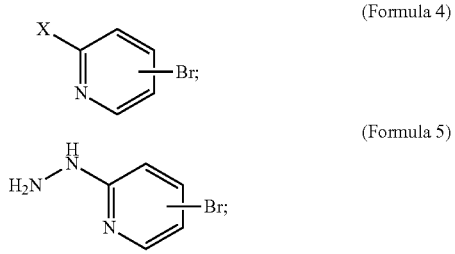

(Formula 4)

(Formula 5)

wherein X is F or Cl;
(b) reacting the compound of Formula 5 under cyclization conditions to obtain a compound of Formula 6:

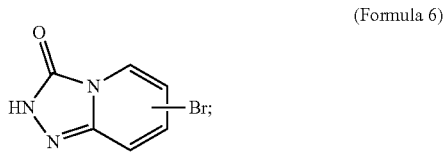

(Formula 6)

and
(c) reacting the compound of Formula 6 with a compound of Formula 8 to obtain the compound of Formula 2:

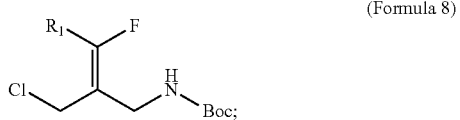

(Formula 8)

wherein $R_1$ is hydrogen or fluoro.

34. The method of claim 33, wherein the cyclization conditions comprise reacting the compound of Formula 5 with carbonyldiimidazole (CDI) in a polar solvent at a temperature ranging from room temperature to 90° C.

35. The method of claim 32, wherein R is a cyclic ring selected from the group consisting of phenyl, pyridinyl, tetrahydropyridinyl, pyrazolyl, benzodioxolyl, 2,3-dihydrobenzodioxinyl, benzothiazolyl, benzoxadiazolyl, benzotriazolyl, indazolyl, pyrrolo[2,3-b]pyridinyl, 3,4-dihydroquinolin-2-onyl, 3,4-dihydro-1,4-benzoxazinyl, 1,4-benzoxazin-3-onyl, 1,3-dihydro-3,1-benzoxazin-2-onyl, 2,3-dihydro-pyrido[2,3-b][1,4]oxazinyl, pyrido[2,3-b][1,4]oxazin-2-onyl, 3,4-dihydro-pyrido[3,2-b][1,4]oxazinyl, and pyrido[3,2-b][1,4]oxazin-3-onyl,
wherein said cyclic ring is optionally substituted with a substituent selected from the group consisting of $C_{1-6}$ alkyl, trifluoromethyl, $C_{1-6}$ alkoxy, amino, mono- or di-$C_{1-6}$ alkylamino, di-$C_{1-6}$ alkylaminomethyl, $C_{1-6}$ alkylcarbonylamino, $C_{1-6}$ alkylsulfonyl, morpholinylsulfonyl, morpholinylcarbonyl, piperazinyl, morpholinyl, triazolyl, pyrazolyl, oxazolyl, oxadiazolyl, and cyclopropyl-oxadiazolyl.

36. A method of treating NASH in a subject in need thereof, the method comprising administering to the subject a therapeutically effective amount of the pharmaceutical composition according to claim 27.

37. A method of treating a disease mediated by VAP-1 in a subject in need thereof, the method comprising administering to the subject a therapeutically effective amount of the pharmaceutical composition according to claim 27.

38. The method of claim 37, wherein the disease mediated by VAP-1 is selected from the group consisting of a lipid disorder, lipoprotein disorder, condition or disease which results from chronic fatty or fibrotic degeneration of organs due to accumulated lipid, triglyceride accumulation and subsequent activation of a profibrotic pathway, Type I Diabetes, Type II Diabetes, complication of Type I or Type II Diabetes, chronic intrahepatic cholestatic condition, extrahepatic cholestatic condition, liver fibrosis, acute intrahepatic cholestatic condition, obstructive or chronic inflammatory disorder that arises out of improper bile composition, gastrointestinal condition with a reduced uptake of dietary fat or fat-soluble dietary vitamin, inflammatory bowel disease, obesity, metabolic syndrome, combined conditions of dyslipidemia, diabetes and abnormally high body-mass index, persistent infection by intracellular bacteria or parasitic protozoae, non-malignant hyperproliferative disorder, malignant hyperproliferative disorder, colon adenocarcinoma, hepatocellular carcinoma, liver steatosis and or associated syndrome, Hepatitis B infection, Hepatitis C infection, a cholestatic and fibrotic effect that is associated with alcohol-induced cirrhosis or with viral-borne forms of hepatitis, liver failure or liver malfunction as an outcome of chronic liver disease or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, or a combination thereof.

* * * * *